United States Patent
Rapecki

(10) Patent No.: US 10,829,566 B2
(45) Date of Patent: Nov. 10, 2020

(54) METHOD EMPLOYING BISPECIFIC ANTIBODIES

(71) Applicant: UCB BIOPHARMA SPRL, Brussels (BE)

(72) Inventor: Stephen Edward Rapecki, Slough (GB)

(73) Assignee: UCB BIOPHARMA SRL, Brussels (BE)

(*) Notice: Subject to any disclaimer, the term of this patent is extended or adjusted under 35 U.S.C. 154(b) by 0 days.

(21) Appl. No.: 15/779,426

(22) PCT Filed: Dec. 1, 2016

(86) PCT No.: PCT/EP2016/079440
§ 371 (c)(1),
(2) Date: May 25, 2018

(87) PCT Pub. No.: WO2017/093408
PCT Pub. Date: Jun. 8, 2017

(65) Prior Publication Data
US 2018/0346604 A1    Dec. 6, 2018

(30) Foreign Application Priority Data
Dec. 3, 2015   (GB) .................................. 1521383.8

(51) Int. Cl.
| | | |
|---|---|---|
| C07K 14/39 | (2006.01) | |
| C07K 16/00 | (2006.01) | |
| G01N 33/68 | (2006.01) | |
| C07K 16/14 | (2006.01) | |
| C07K 16/46 | (2006.01) | |

(52) U.S. Cl.
CPC ............ *C07K 16/468* (2013.01); *C07K 14/39* (2013.01); *C07K 16/00* (2013.01); *C07K 16/14* (2013.01); *G01N 33/6854* (2013.01); *C07K 2319/00* (2013.01)

(58) Field of Classification Search
CPC ...... C07K 16/468; C07K 16/00; C07K 16/14; C07K 14/39; C07K 2319/00; C07K 2317/622; C07K 2317/56; C07K 2317/569; G01N 33/6854; C12N 2502/1107; C12N 2502/1114
See application file for complete search history.

(56) References Cited

U.S. PATENT DOCUMENTS

| | | |
|---|---|---|
| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 6,809,185 B1 | 10/2004 | Schoonjans et al. |
| 6,818,749 B1 | 11/2004 | Kashmiri et al. |
| 7,183,076 B2 | 2/2007 | Arathoon et al. |
| 8,088,378 B2 | 1/2012 | Chen et al. |

(Continued)

FOREIGN PATENT DOCUMENTS

| | | |
|---|---|---|
| EP | 0392745 A2 | 10/1990 |
| EP | 0438474 B1 | 5/1996 |

(Continued)

OTHER PUBLICATIONS

Paul et al., Fundamental Immunology, (textbook), pp. 292-295 (Year: 1993).*
Adair et al., "Therapeutic Antibodies," Drug Design Reviews Online 2(3):209-217 (2005).
Altschul et al., "Basic local alignment search tool," J Mol Biol 215(3):403-410 (1990).
Altschul et al., "Gapped BLAST and PSI-BLAST: a new generation of protein database search programs," Nucleic Acids Res 25(17):3389-3402 (1997).

(Continued)

*Primary Examiner* — Phuong Huynh
(74) *Attorney, Agent, or Firm* — Medler Ferro Woodhouse & Mills PLLC

(57) ABSTRACT

The present invention relates to a method of identifying, separating and characterizing a cell or a population of cells, by capturing at the cell surface, secreted soluble substances (such as an immunoglobulin) that cell or population of cell secrete. This is achieved by combing on a heterodimerically-tethered multispecific protein complex combining a binding specificity for the secreted molecule and a binding specificity for a surface antigen specific for that cell or population of cells. This method may be used in research and experimental purposes, such as patients' stratification in preparation of clinical trials or personalized therapies by identifying cell populations relevant to a pathology and/or prognosis.

17 Claims, 21 Drawing Sheets
Specification includes a Sequence Listing.

(56) References Cited

U.S. PATENT DOCUMENTS

| | | | |
|---|---|---|---|
| 8,409,577 B2 | 4/2013 | Thompson et al. |
| 10,358,493 B2 | 7/2019 | Finney et al. |
| 10,370,447 B2 | 8/2019 | Finney et al. |
| 10,590,197 B2 | 3/2020 | Finney et al. |
| 10,618,957 B2 | 4/2020 | Finney et al. |
| 10,618,979 B2 | 4/2020 | Wright |
| 2003/0027247 A1 | 2/2003 | Wang et al. |
| 2003/0202975 A1 | 10/2003 | Tedder |
| 2005/0033031 A1 | 2/2005 | Cuoto |
| 2005/0048578 A1 | 3/2005 | Zhang |
| 2006/0252130 A1 | 11/2006 | Boehm et al. |
| 2007/0141672 A1 | 6/2007 | Shin |
| 2011/0076270 A1 | 3/2011 | Aversa et al. |
| 2013/0142787 A1 | 6/2013 | Chang et al. |
| 2013/0209463 A1 | 8/2013 | Rotman et al. |
| 2013/0336977 A1 | 12/2013 | Thompson et al. |
| 2014/0099254 A1 | 4/2014 | Chang et al. |
| 2014/0212425 A1 | 7/2014 | Chang et al. |
| 2015/0239974 A1 | 8/2015 | Chang et al. |
| 2017/0081404 A1 | 3/2017 | Finney et al. |
| 2017/0204178 A1 | 7/2017 | Finney et al. |
| 2017/0204183 A1 | 7/2017 | Finney et al. |
| 2018/0201678 A1 | 7/2018 | Finney et al. |
| 2018/0237521 A1 | 8/2018 | Finney et al. |
| 2018/0273620 A1 | 9/2018 | Finney et al. |
| 2018/0334513 A1 | 11/2018 | Wright |
| 2018/0334514 A1 | 11/2018 | Wright |
| 2018/0346603 A1 | 12/2018 | Bhatta et al. |
| 2018/0355063 A1 | 12/2018 | Finney |
| 2019/0322739 A1 | 10/2019 | Finney et al. |

FOREIGN PATENT DOCUMENTS

| | | | |
|---|---|---|---|
| EP | 0463151 B1 | 6/1996 |
| EP | 0546073 B1 | 9/1997 |
| EP | 1242457 B1 | 8/2004 |
| EP | 1570267 B1 | 10/2011 |
| EP | 2706069 A1 | 3/2014 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO93/11162 A1 | 6/1993 |
| WO | WO93/11236 A1 | 6/1993 |
| WO | WO95/15982 A1 | 6/1995 |
| WO | WO95/20401 A1 | 8/1995 |
| WO | WO96/26964 A1 | 9/1996 |
| WO | WO98/20734 A1 | 5/1998 |
| WO | WO02/072832 A2 | 9/2002 |
| WO | WO03/012069 A2 | 2/2003 |
| WO | WO03/031581 A2 | 4/2003 |
| WO | WO03/048327 A2 | 6/2003 |
| WO | WO03/093320 A2 | 11/2003 |
| WO | WO2004/039840 A1 | 5/2004 |
| WO | WO2004/051268 A1 | 6/2004 |
| WO | WO2004/081051 A1 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | 2005/016950 A1 | 2/2005 |
| WO | WO2005/026210 A2 | 3/2005 |
| WO | WO2005/113605 A2 | 12/2005 |
| WO | WO2005/117984 A2 | 12/2005 |
| WO | WO2005/118642 A2 | 12/2005 |
| WO | WO2006/004910 A2 | 1/2006 |
| WO | WO2006/119897 A2 | 11/2006 |
| WO | WO2007/060406 A1 | 5/2007 |
| WO | WO2007/085837 A1 | 8/2007 |
| WO | WO2007/087453 A2 | 8/2007 |
| WO | WO2007/146968 A2 | 12/2007 |
| WO | WO2008/070569 A2 | 6/2008 |
| WO | WO2008/119353 A1 | 10/2008 |
| WO | WO2009/012268 A1 | 1/2009 |
| WO | WO2009/040562 A1 | 4/2009 |
| WO | 2009/099728 A1 | 8/2009 |
| WO | WO2010/035012 A1 | 4/2010 |
| WO | WO2011/025904 A1 | 3/2011 |
| WO | WO2011/061492 A5 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO2012/116453 A1 | 9/2012 |
| WO | WO2012/151199 A1 | 11/2012 |
| WO | WO2012/162561 A2 | 11/2012 |
| WO | WO2013/060867 A2 | 5/2013 |
| WO | WO2013/078455 A2 | 5/2013 |
| WO | WO2013/085893 A1 | 6/2013 |
| WO | WO2014/001326 A1 | 1/2014 |
| WO | WO2014/011518 A1 | 1/2014 |
| WO | WO2014/011519 A1 | 1/2014 |
| WO | WO2014/011520 A1 | 1/2014 |
| WO | WO2014/011521 A1 | 1/2014 |
| WO | 2014/066271 A1 | 5/2014 |
| WO | WO2014/096390 A1 | 6/2014 |
| WO | WO2014/131694 A1 | 9/2014 |
| WO | WO2015/021089 A1 | 2/2015 |
| WO | WO2015/057834 A1 | 4/2015 |
| WO | WO2015/181282 A1 | 12/2015 |
| WO | WO2015/197772 A1 | 12/2015 |
| WO | WO2015/197789 A1 | 12/2015 |
| WO | WO2016/009029 A1 | 1/2016 |
| WO | WO2016/009030 A2 | 1/2016 |
| WO | WO2016/168773 A2 | 10/2016 |
| WO | WO2017/009473 A1 | 1/2017 |
| WO | WO2017/009476 A1 | 1/2017 |
| WO | WO2017/093402 A1 | 6/2017 |
| WO | WO2017/093404 A1 | 6/2017 |
| WO | WO2017/093408 A1 | 6/2017 |
| WO | WO2017/093410 A1 | 6/2017 |

OTHER PUBLICATIONS

Ames et al., "Conversion of murine Fabs isolated from a combinatorial phage display library to full length immunoglobulins," J Immunol Methods 184(2):177-186 (1995).

Angal et al., "A single amino acid substitution abolishes the heterogeneity of chimeric mouse/human (IgG4) antibody," Mol Immunol 30(1):105-108 (1993).

Armour et al., "Recombinant human IgG molecules lacking Fcgamma receptor I binding and monocyte triggering activities," Eur J Immunol 29(8):2613-2624 (1999).

Arndt et al., "Costimulation improves the killing capability of T cells redirected to tumor cells expressing low levels of CD33: description of a novel modular targeting system," Leukemia 28:59-69 (2014).

Babcook et al., "A novel strategy for generating monoclonal antibodies from single, isolated lymphocytes producing antibodies of defined specificities," Proc Natl Acad Sci USA 93(15):7843-7848 (1996).

Bartalena et al., "Thyroid hormone transport proteins," Clin Lab Med 13(3):583-598 (1993).

Berger et al., "Antigen recognition by conformational selection," FEBS Lett 450:149-153 (1999).

Bradshaw et al., "Concurrent detection of secreted products from human lymphocytes by microengraving: cytokines and antigen-reactive antibodies," Clin Immunol 129(1):10-18 (2008).

Bree et al., "Pharmacokinetics of intravenously administered 125I-labelled human alpha 1-acid glycoprotein," Clin Pharmacokinet 11(4):336-342 (1986).

Brinkmann et al., "Phage display of disulfide-stabilized Fv fragments," J Immunol Methods 182(1):41-50 (1995).

(56) References Cited

OTHER PUBLICATIONS

Brosterhus et al., "Enrichment and detection of live antigen-specific CD4(+) and CD8(+) T cells based on cytokine secretion," Eur J Immunol 29(12):4053-4059 (1999).
Bruhns et al., "Specificity and affinity of human Fcgamma receptors and their polymorphic variants for human IgG subclasses," Blood 113(16):3716-3725 (2009).
Burton et al., "Human antibodies from combinatorial libraries," Adv Immunol 57:191-280 (1994).
Caldas et al., "Humanization of the anti-CD18 antibody 6.7: an unexpected effect of a framework residue in binding to antigen," Mol Immunol 39:941-952 (2003).
Campbell et al., "Rapid detection, enrichment and propagation of specific T cell subsets based on cytokine secretion," *Clin Exp Immunol* 163:1-10 (2010).
Carnahan et al., "Epratuzumab, a CD22-targeting recombinant humanized antibody with a different mode of action from rituximab," Molecular Immunology 44(6):1331-1341 (2007).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "Loop-Sequence Features and Stability Determinants in Antibody Variable Domains by High-Throughput Experiments," Structure 22:9-21 (2014).
Chen et al., "Enhancement and destruction of antibody function by somatic mutation: unequal occurrence is controlled by V gene combinatorial associations," *EMBO J* 14(12):2784-2794 (1995).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).
Clargo et al., "The rapid generation of recombinant functional monoclonal antibodies from individual, antigen-specific bone marrow-derived plasma cells isolated using a novel fluorescence-based method," MAbs 6(1):143-159 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2):257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dmitrova et al., "A new LexA-based genetic system for monitoring and analyzing protein heterodimerization in *Escherichia coli*," Mol Gen Genet 257:205-212 (1998).
Doerner et al., "Therapeutic antibody engineering by high efficiency cell screening," *FEBS Lett* 588:278-287 (2014).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig Dis 32:61-66 (2014).

Feldman et al., "Adoptive Cell Therapy—Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161:2791-2797 (1998).
Gish et al., "Identification of protein coding regions by database similarity search," Nat Genet 3(3):266-272 (1993).
Gitlin et al., "The selectivity of the human placenta in the transer of plasma proteins from mother to fetus," J Clin Invest 43:1938-1951 (1964).
Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gold et al., "The B Cell Antigen Receptor Activates the Akt (Protein Kinase B)/Glycogen Synthase Kinase-3 Signaling Pathway via Phosphatidylinositol 3-Kinase," *J Immunol* 163:1894-1905 (1999).
Goldenberg et al., "Multifunctional Antibodies by the Dock-and-Lock Method for Improved Cancer Imaging and Therapy by Pretargeting," *J Nuc Med* 49(1):158-163 (2008).
Gussow et al., "Humanization of Monoclonal Antibodies," Meth Enzymol 203:99-121 (1991).
Hanes et al., "Ribosome display efficiently selects and evolves high-affinity antibodies in vitro from immune libraries," *Proc Natl Acad Sci USA* 95:14130-14135 (1998).
Harris, "Processing of C-terminal lysine and arginine residues of proteins isolated from mammalian cell culture," J Chromatogr A 705(1):129-134 (1995).
Hermiston et al., "CD45: A Critical Regulator of Signaling Thresholds in Immune Cells," Ann Rev Immunol 21:107-137 (2003).
Hinnebusch, "Evidence for translational regulation of the activator of general amino acid control in yeast," Proc Natl Acad Sci USA 81:6442-6446 (1984).
Hinton et al., "Engineered human IgG antibodies with longer serum half-lives in primates," J Biol Chem 279(8):6213-6216 (2004).
Hollinger et al., "Engineered antibody fragments and the rise of single domains," Nat Biotechnol 23(9):1126-1136 (2005).
Holm et al., "Functional mapping and single chain construction of the anti-cytokeratin 8 monoclonal antibody TS11," Mol Immunol 44:1075-1084 (2007).
Holmes, "Buy buy bispecific antibodies," Nat Rev Drug Discov 10(11):798-800 (2011).
Holt et al., "Anti-serum albumin domain antibodies for extending the half-lives of short lived drugs," Protein Eng Des Sel 21(5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).

(56) References Cited

OTHER PUBLICATIONS

Ko et al., "Engineering Antibodies for Dual Specificity and Enhanced Potency," *Biotechnol Bioprocess Eng* 20:201-210 (2015).
Kohler et al., "Continuous cultures of fused cells secreting antibody of predefined specificity," Nature 256:495-497 (1975).
Konterman et al., "Dual targeting strategies with bispecific antibodies," *mAbs*, 4(2):182-197 (2012).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103(11):4005-4010 (2006).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "VI-linker-Vh orientation-dependent expression of single chain Fv-containing an engineered disulfide-stabilized bond in the framework regions," J Biochem 118(4):825-831 (1995).
Luo et al., "Design and Applications of Bispecific Heterodimers: Molecular Imaging and Beyond," *Mol Pharm* 11:1750-1761 (2014).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Pfeifer et al., "Anti-CD22 and anti-CD79B antibody drug conjugates are active in different molecular diffuse large B-cell lymphoma subtypes," *Leukemia* 29:1578-1586 (2015).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rodgers et al., "Switch-mediated activation and retargeting of CAR-T cells for B-cell malignancies," *Proc Natl Acad Sci USA* 113(4):E459-E468 (2016).
Rudikoff et al., "Single amino acid substitution altering antigen-binding specificity," *Proc Natl Acad Sci USA* 79:1979-1983 (1982).
Ryan et al., "Antibody targeting of B-cell maturation antigen on malignant plasma cells," Mol Cancer Ther 6(11):3009-3018 (2007).
Schoonjans et al., "A new model for intermediate molecular weight recombinant bispecific and trispecific antibodies by efficient heterodimerization of single chain variable domains through fusion to a Fab-chain," *Biomol Eng* 17:193-202 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276(9):6591-6604 (2001).
Spang et al., "Heterodimeric Barnase-Barstar Vaccine Molecules: Influence of One versus Two Targeting Units Specific for Antigen Presenting Cells," *PLoS ONE* 7(9):e45393 (2012).
Stavenhagen et al., "Enhancing the potency of therapeutic monoclonal antibodies via Fc optimization," Adv Enzyme Regul 48:152-164 (2008).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Veri et al., "Therapeutic Control of B Cell Activation via a Recruitment of Fcγ Receptor IIb (CD32B) Inhibitory Function with a Novel Bispecific Antibody Scaffold," *Arthritis Rheum* 62(7):1933-1943 (2010).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).
Wang et al., "Antibody Engineering Using Phage Display with a Coiled-Coil Heterodimeric Fv Antibody Fragment," *PLoS ONE* 6(4):e19023 (2011).

(56) References Cited

OTHER PUBLICATIONS

Wienands, "The B-cell antigen receptor: formation of signaling complexes and the function of adaptor proteins," Curr Top Microbiol Immunol 245:53-76 (2000).

Willcox et al., "Production of soluble αβ T-cell receptor heterodimers suitable for biophysical analysis of ligand binding," *Protein Sci* 8:2418-2423 (1999).

Winkler et al., "Changing the Antigen Binding Specificity by Single Point Mutations of an Anti-p24 (HIV-1) Antibody," J Immunol 165:4505-4514 (2000).

Wu et al., "Humanization of a Murine Monoclonal Antibody by Simultaneous Optimization of Framework and CDR Residues," J Mol Biol 294:151-162 (1999).

Yang et al., "CDR walking mutagenesis for the affinity maturation of a potent human anti-HIV-1 antibody into the picomolar range," J Mol Biol 254(3):392-403 (1995).

Young et al., "Thermal stabilization of a single-chain Fv antibody fragment by introduction of a disulphide bond," FEBS Lett 377(2):135-139 (1995).

Yu et al., "Interaction between Bevacizumab and Murine VEGF-A: A Reassessment," *Invest Ophthalmol Vis Sci* 49(2):522-527 (2008).

Yu et al., "Rationalization and Design of the Complementarity Determining Region Sequences in an Antibody-Antigen Recognition Surface," PLOS One 7(3):e33340 (2012).

Zahnd et al., "Directed in Vitro Evolution and Crystallographic Analysis of a Peptide-binding Single Chain Antibody Fragment (scFv) with Low Picomolar Affinity," *J Biol Chem* 279(18):18870-18877 (2004).

Zhang et al., "PowerBLAST: a new network BLAST application for interactive or automated sequence analysis and annotation," Genome Res 7(6):649-656 (1997).

Zhu et al., "Remodeling domain interfaces to enhance heterodimer formation," Protein Sci 6(4):781-788 (1997).

International Search Report issued in PCT/EP2016/079440, dated Feb. 24, 2017.

Non-Final Rejection issued in U.S. Appl. No. 15/311,198, dated Jul. 10, 2018.

Final Rejection issued in U.S. Appl. No. 15/311,198 dated Dec. 21, 2018.

Notice of Allowance issued in U.S. Appl. No. 15/311,198, dated Apr. 10, 2019.

Kussie et al., "A single engineered amino acid substitution changes antibody fine specificity" The Journal of Immunology (1994) 152:146-152.

Ward et al., "Binding activities of a repertoire of single immunoglobulin variable domains secreted from *Escherichia coli*," Nature (1989) 341:544-546.

Hernández-Molina et al., "The meaning of anti-Ro and anti-La antibodies in primary Sjögren's syndrome," Autoimmunity Reviews 10:123-125 (2011).

Lloyd et al., "Modelling the human immune response: performance of a $10^{11}$ human antibody repertoire against a broad panel of therapeutically relevant antigens," Protein Engineering, Design & Selection 22(3):159-168 (2009).

Edwards et al., "The Remarkable Flexibility of the Human Antibody Repertoire; Isolation of Over One Thousand Different Antibodies to a Single Protein, BLyS," J Mol Biol 334:103-118 (2003).

Non-final Office Action dated Nov. 12, 2019, issued in U.S. Appl. No. 15/779,428.

Final Office Action in U.S. Appl. No. 15/779,428, dated Apr. 9, 2020.

Non-final Office Action in U.S. Appl. No. 15/779,424, dated Nov. 25, 2019.

Notice of Allowance in U.S. Appl. No. 15/779,424, dated Apr. 24, 2020.

Non-final Office Action in U.S. Appl. No. 15/779,421, dated Sep. 5, 2019.

Notice of Allowance in U.S. Appl. No. 15/779,421, dated Feb. 11, 2020.

Non-Final Rejection issued in U.S. Appl. No. 15/779,424 dated Nov. 25, 2019.

Non-Final Rejection issued in U.S. Appl. No. 15/779,421 dated Sep. 5, 2019.

Notice of Allowance issued in U.S. Appl. No. 15/779,421 dated Feb. 11, 2020.

Final Office Action issued in U.S. Appl. No. 15/779,428 dated Apr. 9, 2020.

Notice of Allowance issued in issued in U.S. Appl. No. 15/779,424 dated Apr. 24, 2020.

Chang et al., "The Dock and Lock Method: A Novel Platform Technology for Building Multivalent, Multifunctional Structures of Defined Composition with Retained Bioactivity," Clin Cancer Res 13 (18 Suppl): 5586s-5591s (2007).

Kumar et al., "Molecular Cloning and Expression of the Fabs of Human Autoantibodies in *Escherichia coli*," J Biol. Chem. 275(45): 35129-35136 (2000).

Smith-Gill et al., "Contributions of Immunoglobulin Heavy and Light Chains to Antibody Specificity for Lysozyme and Two Haptens," The Journal of Immunology 139(12): 4135-4144 (1987).

Snyder et al., "Overview of Monoclonal Antibodies and Small Molecules Targeting the Epidermal Growth Factor Receptor Pathway in Colorectal Cancer," Clin Colorec Canc 5 (Suppl.2): S71-S80 (2005).

Song et al., "Light Chain of Natural Antibody Plays a Dominant Role in Protein Antigen Binding," Biochem. Biophys Res. Comm. 268: 390-394 (2000).

Non-final Office Action in U.S. Appl. No. 15/779,417, dated Jul. 7, 2020.

Polson et al., "Antibody-drug Conjugates Targeted to CD79 for the Treatment of Non-Hodgkin Lymphoma," Blood 110(2): 616-623 (2007).

Beiboer et al., "Guided Selection of a Pan Carcinoma Specific Antibody Reveals Similar Binding Characteristics Yet Structural Divergence Between the Original Murine Antibody and its Human Equivalent," J. Mol. Biol. 296:833-849 (2000).

Bendig, "Humanization of Rodent Monoclonal Antibodies by CDR Grafting," Methods: A Companion to Methods in Enzymology 8:83-93 (1995).

Klimka et al., "Human anti-CD30 recombinant antibodies by guided phage antibody selection using cell panning," British Journal of Cancer, 83(2):252-260 (2000).

Munodzana et al., "Conformational Dependence of *Anaplasma marginale* Major Surface Protein 5 Surface-Exposed B-Cell Epitopes," Infection and Immunity, American Society for Microbiology 66(6):2619-2624 (1998).

Paul, "Fundamental Immunology: Structure and Function of Immunogloblins", Third Edition, Chapter 9, pp. 292-295, (1993).

Polyak et al., "Blood: Alanine-170 and proline-172 are critical determinants for extra cellular CD20 epitopes; heterogeneity in the fine specificity of CD20 monoclonal antibodies is defined by additional requirements imposed by both amino acid sequence and quaternary structure," Blood Journal 99: 3256-3262 (2002).

Portolano et al., "Lack of Promiscuity in Autoantigen-Specific H and L Chain Combinations as Revealed by Human H and L Chain Roulette", The Journal of Immunology, 150(3):80-887 (1993).

\* cited by examiner

High affinity interaction.

Surface plasmon resonance analysis of Antigen5Fab- scFv (52RS4) binding to GNC4 peptide

| Sample | Biotin-GCN4 Peptide | | | |
|---|---|---|---|---|
| | ka (1/Ms) | kd (1/s) | Affinity (pM) | Immuno-reactivity % |
| Antigen5Fab52RS4scFv | 5.10E+05 | 2.70E-04 | 516 | 105 |

% Immunoreactivity = Rmax/Estimated Rmax x 100

```
                       SEQUENCE LISTING

<160> NUMBER OF SEQ ID NOS: 104

<210> SEQ ID NO 1
<211> LENGTH: 44
<212> TYPE: PRT
<213> ORGANISM: Artificial Sequence
<220> FEATURE:
<223> OTHER INFORMATION: CN4(7P14P) sequence

<400> SEQUENCE: 1

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
        35                  40

<210> SEQ ID NO 2
<211> LENGTH: 132
<212> TYPE: DNA
<213> ORGANISM: Artificial Sequence
<220> FEATURE:
<223> OTHER INFORMATION: DNA encoding

<400> SEQUENCE: 2
gctagcggag gcggaagaat gaaacaactt gaacccaagg ttgaagaatt gcttccgaaa      60
aattatcact ggaaaatga ggttgccaga ttaaagaaat tagttggcga acgccatcac     120
catcaccatc ac                                                         132

<210> SEQ ID NO 3
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 3

Asp Ala Val Val Thr Gln Glu Ser Ala Leu Thr Ser Ser Pro Gly Glu
```

```
  1               5                   10                  15
Thr Val Thr Leu Thr Cys Arg Ser Ser Thr Gly Ala Val Thr Thr Ser
             20                  25                  30
Asn Tyr Ala Ser Trp Val Gln Glu Lys Pro Asp His Leu Phe Thr Gly
             35                  40                  45
Leu Ile Gly Gly Thr Asn Asn Arg Ala Pro Gly Val Pro Ala Arg Phe
             50                  55                  60
Ser Gly Ser Leu Ile Gly Asp Lys Ala Ala Leu Thr Ile Thr Gly Ala
 65                  70                  75                  80
Gln Thr Glu Asp Glu Ala Ile Tyr Phe Cys Val Leu Trp Tyr Ser Asp
             85                  90                  95
His Trp Val Phe Gly Cys Gly Thr Lys Leu Thr Val Leu Gly Gly Gly
            100                 105                 110
Gly Gly Ser Gly Gly Gly Ser Gly Gly Gly Ser Gly Gly Gly
            115                 120                 125
Gly Ser Asp Val Gln Leu Gln Gln Ser Gly Pro Gly Leu Val Ala Pro
130                 135                 140
Ser Gln Ser Leu Ser Ile Thr Cys Thr Val Ser Gly Phe Leu Leu Thr
145                 150                 155                 160
Asp Tyr Gly Val Asn Trp Val Arg Gln Ser Pro Gly Lys Cys Leu Glu
            165                 170                 175
Trp Leu Gly Val Ile Trp Gly Asp Gly Ile Thr Asp Tyr Asn Ser Ala
            180                 185                 190
Leu Lys Ser Arg Leu Ser Val Thr Lys Asp Asn Ser Lys Ser Gln Val
            195                 200                 205
Phe Leu Lys Met Asn Ser Leu Gln Ser Gly Asp Ser Ala Arg Tyr Tyr
            210                 215                 220
Cys Val Thr Gly Leu Phe Asp Tyr Trp Gly Gln Gly Thr Thr Leu Thr
225                 230                 235                 240
Val Ser Ser Ala Ala Ala His His His His His Glu Gln Lys Leu
            245                 250                 255
Ile Ser Glu Glu Asp Leu
            260

<210> SEQ ID NO 4
<211> LENGTH: 792
<212> TYPE: DNA
<213> ORGANISM: Artificial Sequence
<220> FEATURE:
<223> OTHER INFORMATION: DNA encoding

<400> SEQUENCE: 4
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca acaaccgcgc gccgggcgtg     180
ccggcgcgct ttagcggcag cctgattggc gataaagcgg cgctgaccat taccggcgcg     240
cagaccgaag atgaagcgat ttattttttgc gtgctgtggt atagcgacca ttgggtgttt     300
ggctgcggca ccaaactgac cgtgctgggt ggaggcggtg gctcaggcgg aggtggctca     360
ggcggtggcg ggtctggcgg cggcggcagc gatgtgcagc tgcagcagag cggcccgggc     420
ctggtggcgc cgagccagag cctgagcatt acctgcaccg tgagcggctt tctcctgacc     480
gattatggcg tgaactgggt gcgccagagc ccgggcaaat gcctggaatg gctgggcgtg     540
atttggggcg atggcattac cgattataac agcgcgctga aaagccgcct gagcgtgacc     600
```

```
aaagataaca gcaaaagcca ggtgtttctg aaaatgaaca gcctgcagag cggcgatagc      660
gcgcgctatt attgcgtgac cggcctgttt gattattggg gccagggcac caccctgacc      720
gtgagcagcg cggccgccca tcaccatcac catcacgaac agaaactgat tagcgaagaa      780
gatctgtaat ag                                                          792
```

```
<210> SEQ ID NO 5
<211> LENGTH: 8
<212> TYPE: PRT
<213> ORGANISM: Artificial Sequence
<220> FEATURE:
<223> OTHER INFORMATION: FLEXIBLE PEPTIDE LINKER

<400> SEQUENCE: 5

Asp Lys Thr His Thr Cys Ala Ala
1               5

<210> SEQ ID NO 6
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 6

Asp Lys Thr His Thr Cys Pro Pro Cys Pro Ala
1               5                   10

<210> SEQ ID NO 7
<211> LENGTH: 18
<212> TYPE: PRT
<213> ORGANISM: Artificial Sequence
<220> FEATURE:
<223> OTHER INFORMATION: FLEXIBLE PEPTIDE LINKER

<400> SEQUENCE: 7

Asp Lys Thr His Thr Cys Pro Pro Cys Pro Ala Thr Cys Pro Pro Cys
1               5                   10                  15

Pro Ala

<210> SEQ ID NO 8
<211> LENGTH: 25
<212> TYPE: PRT
<213> ORGANISM: Artificial Sequence
<220> FEATURE:
<223> OTHER INFORMATION: FLEXIBLE PEPTIDE LINKER

<400> SEQUENCE: 8

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 9
<211> LENGTH: 30
<212> TYPE: PRT
<213> ORGANISM: Artificial Sequence
<220> FEATURE:
<223> OTHER INFORMATION: FLEXIBLE PEPTIDE LINKER

<400> SEQUENCE: 9

Asp Lys Thr His Thr Cys Pro Pro Cys Pro Ala Gly Lys Pro Thr Leu
1               5                   10                  15
```

Tyr Asn Ser Leu Val Met Ser Asp Thr Ala Gly Thr Cys Tyr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: FLEXIBLE PEPTIDE LINKER

<400> SEQUENCE: 10

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 11
<211> LENGTH: 15
<212> TYPE: PRT
<213> ORGANISM: Artificial Sequence
<220> FEATURE:
<223> OTHER INFORMATION: FLEXIBLE PEPTIDE LINKER

<400> SEQUENCE: 11

Asp Lys Thr His Thr Cys Cys Val Glu Cys Pro Pro Cys Pro Ala
1               5                   10                  15

<210> SEQ ID NO 12
<211> LENGTH: 26
<212> TYPE: PRT
<213> ORGANISM: Artificial Sequence
<220> FEATURE:
<223> OTHER INFORMATION: FLEXIBLE PEPTIDE LINKER

<400> SEQUENCE: 12

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 13
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 13

Asp Lys Thr His Thr Cys Pro Ser Cys Pro Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Glu
1               5

<210> SEQ ID NO 15
<211> LENGTH: 6
<212> TYPE: PRT
<213> ORGANISM: Artificial Sequence

```
<220> FEATURE:
<223> OTHER INFORMATION: Flexible linker

<400> SEQUENCE: 15

Asp Lys Thr His Thr Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Flexible linker

<400> SEQUENCE: 18

Ser Gly Gly Gly Gly Ser Gly Gly Gly Gly Ser Gly Gly Gly Gly Ser
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Flexible linker

<400> SEQUENCE: 19

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 20
<211> LENGTH: 26
<212> TYPE: PRT
<213> ORGANISM: Artificial Sequence
<220> FEATURE:
<223> OTHER INFORMATION: Flexible linker

<400> SEQUENCE: 20

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25
```

```
<210> SEQ ID NO 21
<211> LENGTH: 11
<212> TYPE: PRT
<213> ORGANISM: Artificial Sequence
<220> FEATURE:
<223> OTHER INFORMATION: Flexible linker

<400> SEQUENCE: 21

Ala Ala Ala Gly Ser Gly Gly Ala Ser Ala Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Ala Ala Ala Gly Ser Gly Xaa Gly Gly Gly Ser Gly Ala Ser Ala Ser
1               5                   10                  15

<210> SEQ ID NO 23
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 24
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Ala Ala Ala Gly Ser Gly Xaa Gly Gly Gly Ser Xaa Gly Gly Gly Ser
1               5                   10                  15
```

```
Xaa Gly Gly Gly Ser Gly Ala Ser Ala Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 25

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 26
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 26

Ala Ala Ala Gly Ser Gly Xaa Ser Gly Ala Ser Ala Ser
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Flexible linker

<400> SEQUENCE: 27

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 28
<211> LENGTH: 11
<212> TYPE: PRT
<213> ORGANISM: Artificial Sequence
<220> FEATURE:
<223> OTHER INFORMATION: Flexible linker

<400> SEQUENCE: 28

Ala Thr Thr Thr Gly Ser Ser Pro Gly Pro Thr
```

<210> SEQ ID NO 29
<211> LENGTH: 6
<212> TYPE: PRT
<213> ORGANISM: Artificial Sequence
<220> FEATURE:
<223> OTHER INFORMATION: Flexible linker

<400> SEQUENCE: 29

```
Ala Thr Thr Thr Gly Ser
1               5
```

<210> SEQ ID NO 30
<211> LENGTH: 13
<212> TYPE: PRT
<213> ORGANISM: Artificial Sequence
<220> FEATURE:
<223> OTHER INFORMATION: Flexible linker

<400> SEQUENCE: 30

```
Ala Ala Ala Ala Ala Ala Ala Ala Ala Ala Ala Ala Ala
1               5                   10
```

<210> SEQ ID NO 31
<211> LENGTH: 21
<212> TYPE: PRT
<213> ORGANISM: Artificial Sequence
<220> FEATURE:
<223> OTHER INFORMATION: Flexible linker

<400> SEQUENCE: 31

```
Glu Pro Ser Gly Pro Ile Ser Thr Ile Asn Ser Pro Ser Lys Glu
1               5                   10                  15

Ser His Lys Ser Pro
            20
```

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

```
Gly Thr Val Ala Ala Pro Ser Val Phe Ile Phe Pro Pro Ser Asp
1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

```
Gly Gly Gly Gly Ile Ala Pro Ser Met Val Gly Gly Gly Gly Ser
1               5                   10                  15
```

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Lys Val Glu Gly Ala Gly Gly Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Flexible linker

<400> SEQUENCE: 35

Gly Gly Gly Gly Ser Met Lys Ser His Asp Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Flexible linker

<400> SEQUENCE: 36

Gly Gly Gly Gly Asn Leu Ile Thr Ile Val Gly Gly Gly Gly Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Flexible linker

<400> SEQUENCE: 37

Gly Gly Gly Gly Val Val Pro Ser Leu Pro Gly Gly Gly Gly Ser
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Flexible linker

<400> SEQUENCE: 38

Gly Gly Glu Lys Ser Ile Pro Gly Gly Gly Gly Ser
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Leu Ser Tyr Arg Pro Pro Phe Pro Phe Gly Phe Pro Ser Val
1               5                   10                  15

Arg Pro

<210> SEQ ID NO 40
<211> LENGTH: 18
<212> TYPE: PRT
<213> ORGANISM: Artificial Sequence
<220> FEATURE:
<223> OTHER INFORMATION: Flexible linker

```
<400> SEQUENCE: 40

Tyr Pro Arg Ser Ile Tyr Ile Arg Arg His Pro Ser Pro Ser Leu
1               5                   10                  15

Thr Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Thr Pro Ser His Leu Ser His Ile Leu Pro Ser Phe Gly Leu Pro Thr
1               5                   10                  15

Phe Asn

<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Arg Pro Val Ser Pro Phe Thr Phe Pro Arg Leu Ser Asn Ser Trp Leu
1               5                   10                  15

Pro Ala

<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Ser Pro Ala Ala His Phe Pro Arg Ser Ile Pro Arg Pro Gly Pro Ile
1               5                   10                  15

Arg Thr

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ala Pro Gly Pro Ser Ala Pro Ser His Arg Ser Leu Pro Ser Arg Ala
1               5                   10                  15

Phe Gly

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Pro Arg Asn Ser Ile His Phe Leu His Pro Leu Leu Val Ala Pro Leu
1               5                   10                  15
```

Gly Ala

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Met Pro Ser Leu Ser Gly Val Leu Gln Val Arg Tyr Leu Ser Pro Pro
1               5                   10                  15

Asp Leu

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Ser Pro Gln Tyr Pro Ser Pro Leu Thr Leu Thr Leu Pro Pro His Pro
1               5                   10                  15

Ser Leu

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Asn Pro Ser Leu Asn Pro Pro Ser Tyr Leu His Arg Ala Pro Ser Arg
1               5                   10                  15

Ile Ser

<210> SEQ ID NO 49
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Pro Trp Arg Thr Ser Leu Leu Pro Ser Leu Pro Leu Arg Arg Arg
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Pro Leu Phe Ala Lys Gly Pro Val Gly Leu Leu Ser Arg Ser Phe
1               5                   10                  15

Pro Pro

-continued

```
<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Val Pro Pro Ala Pro Val Val Ser Leu Arg Ser Ala His Ala Arg Pro
1               5                   10                  15

Pro Tyr

<210> SEQ ID NO 52
<211> LENGTH: 17
<212> TYPE: PRT
<213> ORGANISM: Artificial Sequence
<220> FEATURE:
<223> OTHER INFORMATION: Flexible linker

<400> SEQUENCE: 52

Leu Arg Pro Thr Pro Pro Arg Val Arg Ser Tyr Thr Cys Cys Pro Thr
1               5                   10                  15

Pro

<210> SEQ ID NO 53
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Pro Asn Val Ala His Val Leu Pro Leu Leu Thr Val Pro Trp Asp Asn
1               5                   10                  15

Leu Arg

<210> SEQ ID NO 54
<211> LENGTH: 18
<212> TYPE: PRT
<213> ORGANISM: Artificial Sequence
<220> FEATURE:
<223> OTHER INFORMATION: Flexible linker

<400> SEQUENCE: 54

Cys Asn Pro Leu Leu Pro Leu Cys Ala Arg Ser Pro Ala Val Arg Thr
1               5                   10                  15

Phe Pro

<210> SEQ ID NO 55
<211> LENGTH: 11
<212> TYPE: PRT
<213> ORGANISM: Artificial Sequence
<220> FEATURE:
<223> OTHER INFORMATION: Linker

<400> SEQUENCE: 55

Asp Leu Cys Leu Arg Asp Trp Gly Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Linker
```

<400> SEQUENCE: 56

Asp Ile Cys Leu Pro Arg Trp Gly Cys Leu Trp
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Linker

<400> SEQUENCE: 57

Met Glu Asp Ile Cys Leu Pro Arg Trp Gly Cys Leu Trp Gly Asp
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: Linker

<400> SEQUENCE: 58

Gln Arg Leu Met Glu Asp Ile Cys Leu Pro Arg Trp Gly Cys Leu Trp
1               5                   10                  15

Glu Asp Asp Glu
            20

<210> SEQ ID NO 59
<211> LENGTH: 20
<212> TYPE: PRT
<213> ORGANISM: Artificial Sequence
<220> FEATURE:
<223> OTHER INFORMATION: Linker

<400> SEQUENCE: 59

Gln Gly Leu Ile Gly Asp Ile Cys Leu Pro Arg Trp Gly Cys Leu Trp
1               5                   10                  15

Gly Arg Ser Val
            20

<210> SEQ ID NO 60
<211> LENGTH: 21
<212> TYPE: PRT
<213> ORGANISM: Artificial Sequence
<220> FEATURE:
<223> OTHER INFORMATION: Linker

<400> SEQUENCE: 60

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 61
<211> LENGTH: 15
<212> TYPE: PRT
<213> ORGANISM: Artificial Sequence
<220> FEATURE:
<223> OTHER INFORMATION: Linker

<400> SEQUENCE: 61

Glu Asp Ile Cys Leu Pro Arg Trp Gly Cys Leu Trp Glu Asp Asp
1               5                   10                  15

```
<210> SEQ ID NO 62
<211> LENGTH: 18
<212> TYPE: PRT
<213> ORGANISM: Artificial Sequence
<220> FEATURE:
<223> OTHER INFORMATION: Linker

<400> SEQUENCE: 62

Arg Leu Met Glu Asp Ile Cys Leu Pro Arg Trp Gly Cys Leu Trp Glu
1               5                   10                  15

Asp Asp

<210> SEQ ID NO 63
<211> LENGTH: 16
<212> TYPE: PRT
<213> ORGANISM: Artificial Sequence
<220> FEATURE:
<223> OTHER INFORMATION: Linker

<400> SEQUENCE: 63

Met Glu Asp Ile Cys Leu Pro Arg Trp Gly Cys Leu Trp Glu Asp Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Linker

<400> SEQUENCE: 64

Met Glu Asp Ile Cys Leu Pro Arg Trp Gly Cys Leu Trp Glu Asp
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Linker

<400> SEQUENCE: 65

Arg Leu Met Glu Asp Ile Cys Leu Ala Arg Trp Gly Cys Leu Trp Glu
1               5                   10                  15

Asp Asp

<210> SEQ ID NO 66
<211> LENGTH: 20
<212> TYPE: PRT
<213> ORGANISM: Artificial Sequence
<220> FEATURE:
<223> OTHER INFORMATION: Linker

<400> SEQUENCE: 66

Glu Val Arg Ser Phe Cys Thr Arg Trp Pro Ala Glu Lys Ser Cys Lys
1               5                   10                  15

Pro Leu Arg Gly
            20

<210> SEQ ID NO 67
<211> LENGTH: 20
<212> TYPE: PRT
<213> ORGANISM: Artificial Sequence
<220> FEATURE:
```

<223> OTHER INFORMATION: Linker

<400> SEQUENCE: 67

Arg Ala Pro Glu Ser Phe Val Cys Tyr Trp Glu Thr Ile Cys Phe Glu
1               5                   10                  15

Arg Ser Glu Gln
            20

<210> SEQ ID NO 68
<211> LENGTH: 11
<212> TYPE: PRT
<213> ORGANISM: Artificial Sequence
<220> FEATURE:
<223> OTHER INFORMATION: Linker

<400> SEQUENCE: 68

Glu Met Cys Tyr Phe Pro Gly Ile Cys Trp Met
1               5                   10

<210> SEQ ID NO 69
<211> LENGTH: 11
<212> TYPE: PRT
<213> ORGANISM: Artificial Sequence
<220> FEATURE:
<223> OTHER INFORMATION: peptide sequence

<400> SEQUENCE: 69

Gly Ala Pro Ala Pro Ala Ala Pro Ala Pro Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: peptide sequence

<400> SEQUENCE: 70

Pro Pro Pro Pro
1

<210> SEQ ID NO 71
<211> LENGTH: 6
<212> TYPE: PRT
<213> ORGANISM: Artificial sequence
<220> FEATURE:
<223> OTHER INFORMATION: Linker

<400> SEQUENCE: 71

Ala Ser Gly Gly Gly Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Linker

<400> SEQUENCE: 72

Ala Ser Gly Gly Gly Gly Ser Gly
1               5

<210> SEQ ID NO 73
<211> LENGTH: 5
<212> TYPE: PRT

```
<213> ORGANISM: Artificial Sequence
<220> FEATURE:
<223> OTHER INFORMATION: Linker

<400> SEQUENCE: 73

Ala Ser Gly Gly Gly
1               5

<210> SEQ ID NO 74
<211> LENGTH: 7
<212> TYPE: PRT
<213> ORGANISM: Artificial Sequence
<220> FEATURE:
<223> OTHER INFORMATION: Linker

<400> SEQUENCE: 74

Ala Ala Ala Ser Gly Gly Gly
1               5

<210> SEQ ID NO 75
<211> LENGTH: 20
<212> TYPE: PRT
<213> ORGANISM: Artificial Sequence
<220> FEATURE:
<223> OTHER INFORMATION: Linker

<400> SEQUENCE: 75

Ser Gly Gly Gly Gly Ser Gly Gly Gly Ser Gly Gly Gly Ser
1               5                   10                  15

Gly Gly Gly Ser
            20

<210> SEQ ID NO 76
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 76

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Lys Lys
            20                  25                  30

Leu Val Gly Glu Arg His His His His His His
            35                  40

<210> SEQ ID NO 77
<211> LENGTH: 43
<212> TYPE: PRT
<213> ORGANISM: artificial sequence
<220> FEATURE:
<223> OTHER INFORMATION: GCN4 peptide variant

<400> SEQUENCE: 77

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Lys Ala
            20                  25                  30

Leu Val Gly Glu Arg His His His His His
            35                  40

<210> SEQ ID NO 78
<211> LENGTH: 43
```

```
<212> TYPE: PRT
<213> ORGANISM: Artificial Sequence
<220> FEATURE:
<223> OTHER INFORMATION: GCN4 peptide variant

<400> SEQUENCE: 78

Gly Gly Gly Gly Ser Gly Gly Gly Gly Ser Gly Gly Gly Gly Ser Gly
1               5                   10                  15

Gly Gly Gly Ser Tyr His Leu Glu Asn Glu Val Ala Arg Leu Ala Lys
            20                  25                  30

Leu Val Gly Glu Arg His His His His His His
        35                  40

<210> SEQ ID NO 79
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 79

Gly Gly Gly Gly Ser Gly Gly Gly Gly Ser Gly Gly Gly Gly Ser Gly
1               5                   10                  15

Gly Gly Gly Ser Tyr His Leu Glu Asn Glu Val Ala Arg Leu Gln Lys
            20                  25                  30

Leu Val Gly Glu Arg His His His His His His
        35                  40

<210> SEQ ID NO 80
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 80

Gly Gly Gly Gly Ser Gly Gly Gly Gly Ser Gly Gly Gly Gly Ser Gly
1               5                   10                  15

Gly Gly Gly Ser Tyr His Leu Glu Asn Glu Val Ala Arg Leu Asn Lys
            20                  25                  30

Leu Val Gly Glu Arg His His His His His His
        35                  40

<210> SEQ ID NO 81
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 81

Gly Gly Gly Gly Ser Gly Gly Gly Gly Ser Gly Gly Gly Gly Ser Gly
1               5                   10                  15

Gly Gly Gly Ser Tyr His Leu Glu Asn Glu Val Ala Arg Leu Ala Ala
            20                  25                  30

Leu Val Gly Glu Arg His His His His His His
        35                  40

<210> SEQ ID NO 82
<211> LENGTH: 43
<212> TYPE: PRT
<213> ORGANISM: Artificial Sequence
<220> FEATURE:
```

<223> OTHER INFORMATION: GCN4 peptide variant

<400> SEQUENCE: 82

Gly Gly Gly Gly Ser Gly Gly Gly Ser Gly Gly Gly Ser Gly
1               5                   10                  15

Gly Gly Gly Ser Tyr His Leu Glu Asn Glu Val Ala Arg Leu Gln Ala
                20                  25                  30

Leu Val Gly Glu Arg His His His His His His
        35                  40

<210> SEQ ID NO 83
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 83

Gly Gly Gly Gly Ser Gly Gly Gly Ser Gly Gly Gly Ser Gly
1               5                   10                  15

Gly Gly Gly Ser Tyr His Leu Glu Asn Glu Val Ala Arg Leu Asn Ala
                20                  25                  30

Leu Val Gly Glu Arg His His His His His His
        35                  40

<210> SEQ ID NO 84
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 84

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
                20                  25                  30

Lys Leu Val Gly Glu Arg His His His His His His
        35                  40

<210> SEQ ID NO 85
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 85

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
                20                  25                  30

Ala Leu Val Gly Glu Arg His His His His His His
        35                  40

<210> SEQ ID NO 86
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 86

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Ala Leu Val Gly Glu Arg His His His His His His
        35                  40

<210> SEQ ID NO 87
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 87

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
        35                  40

<210> SEQ ID NO 88
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 88

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 89
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 89

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 90
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 90

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
        35                  40

<210> SEQ ID NO 91
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 91

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 92
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 92

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 93
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 93

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 94
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 94

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His
        35                  40

<210> SEQ ID NO 95
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 95

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Ala Leu Val Gly Glu Arg His His His His His His
        35                  40

<210> SEQ ID NO 96
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 96

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 97
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 97

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His His
        35                  40

<210> SEQ ID NO 98
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 98

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Ala Leu Val Gly Glu Arg His His His His His His
        35                  40

<210> SEQ ID NO 99
<211> LENGTH: 243
<212> TYPE: PRT
<213> ORGANISM: Artificial Sequence
<220> FEATURE:
<223> OTHER INFORMATION: 52SR4 scFV variant

<400> SEQUENCE: 99

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Ser Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser
```

<210> SEQ ID NO 100
<211> LENGTH: 292
<212> TYPE: PRT
<213> ORGANISM: Artificial Sequence
<220> FEATURE:
<223> OTHER INFORMATION: 52SR4 scFv variant

<400> SEQUENCE: 100

```
Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60
```

Ser Arg Leu Ser Val Thr Lys Asp Asn Ser Lys Ser Gln Val Phe Leu
 65                  70                  75                  80

Lys Met Asn Ser Leu Gln Ser Gly Asp Ser Ala Arg Tyr Tyr Cys Val
                 85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
            115                 120                 125

Thr Ile Thr Gly Ala Gln Thr Glu Asp Glu Ala Ile Tyr Phe Cys Val
130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly Gly
            165                 170                 175

Gly Ser Gly Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
            195                 200                 205

Thr Gly Ala Val Thr Thr Ser Asn Tyr Ala Ser Trp Val Gln Glu Lys
210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
            245                 250                 255

Ala Leu Thr Ile Thr Gly Ala Gln Thr Glu Asp Glu Ala Ile Tyr Phe
            260                 265                 270

Cys Val Leu Trp Tyr Ser Asp His Trp Val Phe Gly Cys Gly Thr Lys
            275                 280                 285

Leu Thr Val Leu
    290

<210> SEQ ID NO 101
<211> LENGTH: 20
<212> TYPE: PRT
<213> ORGANISM: Artificial Sequence
<220> FEATURE:
<223> OTHER INFORMATION: signal sequence

<400> SEQUENCE: 101

Met Ser Val Pro Thr Gln Val Leu Gly Leu Leu Leu Leu Trp Leu Thr
1               5                   10                  15

Asp Ala Arg Cys
            20

<210> SEQ ID NO 102
<211> LENGTH: 19
<212> TYPE: PRT
<213> ORGANISM: Artificial Sequence
<220> FEATURE:
<223> OTHER INFORMATION: signal sequence

<400> SEQUENCE: 102

Met Glu Trp Ser Trp Val Phe Leu Phe Phe Leu Ser Val Thr Thr Gly
1               5                   10                  15

Val His Ser

<210> SEQ ID NO 103

```
<211> LENGTH: 19
<212> TYPE: PRT
<213> ORGANISM: Artificial Sequence
<220> FEATURE:
<223> OTHER INFORMATION: signal sequence

<400> SEQUENCE: 103

Met Asp Trp Leu Trp Thr Leu Leu Phe Leu Met Ala Ala Ala Gln Ser
1               5                   10                  15

Ala Gln Ala

<210> SEQ ID NO 104
<211> LENGTH: 19
<212> TYPE: PRT
<213> ORGANISM: Artificial Sequence
<220> FEATURE:
<223> OTHER INFORMATION: signal sequence

<400> SEQUENCE: 104

Met Gly Trp Ser Trp Thr Phe Leu Phe Leu Leu Ser Gly Thr Ser Gly
1               5                   10                  15

Val Leu Ser
```

METHOD EMPLOYING BISPECIFIC ANTIBODIES

REFERENCE TO AN ELECTRONIC SEQUENCE LISTING

The contents of the electronic sequence listing (00890018US1seqlist.txt; Size: 38 KB; and Date of Creation May 22, 2018) is herein incorporated by reference in its entirety.

FIELD OF INVENTION

The present disclosure relates to a method of combining two binding specificities in a heterodimerically-tethered multispecific protein complex to facilitate cell surface capture of soluble molecules to the cell that produced them and hence identification, separation and characterisation of that cell or population of cells, libraries/multiplexes of the multispecific protein complexes, and kits and compositions thereof. The disclosure further relates to said novel multispecific protein complexes, for example for use in research and experimental purposes, such as for use in assays to characterise patient populations by identifying cell populations relevant to a pathology and/or prognosis. The present disclosure also extends to methods of preparing said multispecific complexes.

BACKGROUND OF INVENTION

Secreted soluble molecules are key mediators of cellular function, and understanding the cell lineages that produce them, under what conditions and when is at the heart of complex cell biology in nature and in disease. Methods exist to study secretion from single cells but they all have limitations. Some require complex technologies such as single cell imaging, or microegraving (Nat. Biotech. 2006. 24. 703-707; Clin. Immunol. 2008. 129. 10-18). Simpler methods for use by flow cytometry such as bispecific antibody capture (Eur. J. Immunol. 1999. 29. 4053-4059) have been reported and are sold commercially for some cell/cytokine combinations (Miltenyi biotech), however these require the generation of bespoke reagents with pre-defined combinations of cell surface marker & soluble molecule specificities. Thus there exists the requirement for a simple modular system to combine any cell surface marker specificity with any soluble molecule specificity for the study of cellular function and lineages.

The preparation of known (traditional) multispecific formats is time consuming and labour intensive.

Typically for a single bispecific antibody construct at least two variable regions need to be sub-cloned from the original source of discovery vectors (e.g. phage display, hybridoma or single B-cell cloning) into appropriate bispecific expression vectors, each arm of the bispecific has to be expressed and the resulting bispecific antibody purified. This cloning and subsequent expression effort quickly becomes a significant practical bottleneck if large numbers of pairs of variable regions are to be combined in an attempt to interrogate the sample or samples, with a large number of functional questions.

For example, if 50 unique antibodies are available to a panel of 10 cell surface targets, and 50 unique antibodies are available to a panel of 10 soluble molecules, then a total of 2500 bispecific antibodies could potentially be generated (envisaged as an X-by-Y grid). With the bispecific antibody formats known in the art this would require at least 100 individual cloning reactions (50-X and 50-Y) followed by 2500 antibody expression experiments. Increasing the number of starting monoclonal antibodies to 100 would increase the minimal number of cloning reactions to 200 (100-X and 100-Y) and the expression number to 10,000.

Generally the root cause of this 'expression bottleneck' is the fact that the formats described above require both protein chain 'halves' of the final bispecific construct to be expressed simultaneously within a single expression experiment in the same cell. Therefore, for many formats, to produce 2500 bispecific antibodies, 2500 expression experiments are required.

The 'expression bottleneck' is further exacerbated if the bispecific antibody format is monocistronic (i.e. cloned and expressed as a single chain protein), for example single chain diabodies, as the number of cloning experiments would be 2500 and 10,000 respectively for the numbers given above.

Furthermore after expression, extensive purification may be required to isolate the desired construct.

Some bispecific approaches employ a common light chain in the bispecific constructs in order to reduce the amount of cloning, although this doesn't reduce the number of expression experiments. Furthermore, using a common chain, such as a common light chain, makes the challenge of antibody discovery harder as it is more difficult to find the starting antibody variable domains as the antibody needs to bind its antigen with a high enough affinity through one chain, such as the heavy chain, alone.

Many promising bispecific antibody formats have now been developed that could potentially work as successful therapeutics including DVD-Ig (Abbvie), DuoBodies (Genmab), Knobs-in-Holes (Genentech), Common light chain (Merus). However, in each case these formats are not ideally suited for analysis and/or characterisation of populations of cells from patients, for example in large scale clinical trials.

New medical treatments (new medicines) often are only effective in a sub-population of patients. However, to identify such populations, large amounts of data need to be collected so that any underlying patterns can be identified.

Often data is collected in the form of transcriptomic c information which gives evidence on the up-regulation and down-regulation of a set of genes. Whilst this information is valuable it does not instruct on how these changes are reflected at protein level.

Since changes in protein level reflect the outcome of many inputs such as changes in gene transcription, epigenetic regulation, protein transcription, protein translation, protein modification, and metabolic function they represent a more integrated measure of cell health and function. Thus analysis of proteins is more relevant for the reasons indicated and in addition can be used to sensitively discriminate cellular populations and sub-populations in health and disease. Although characterisation of cellular subsets can be determined by quantification of cell surface proteins currently cellular secretion products (which can include but not exclusively proteins, lipids, nucleic acids etc.) cannot not be used as a cellular identifier unless the cells are held in a solid or semi-solid matrix. Hence there is a need for an optimised system to capture secreted cell products that can also be measured in an aqueous environment such as the blood or interstitial fluids. In addition there is also the need for a technique that can work in complex cell mixtures and only capture the secreted product of the cell that produced it and not by other cells in close proximity.

We propose that rather than designing and testing a limited selection of bispecific or multispecific antibodies that engage given epitopes on a cell target and a soluble target, the true potential of identifying cells producing soluble molecules can only be achieved by being able to combine, flexibly, a large, diverse combinatorial panel of bispecific or multispecific antibodies or protein ligands. To facilitate this a format and a method is required that enables the generation of large numbers of diverse multispecific proteins which can be readily constructed and screened for the ability to capture secreted molecules to the surface of the cell that produced them and hence identify that cell. This approach further allows for the serendipitous identification of biological mechanisms and/or sub-groups of cells.

Thus it would be useful to generate and screen a large number of multispecific protein complexes with binding domains with different combinations of specificities. In particular, it would be useful to be able to screen a sample or samples with a large number of different multispecific protein complexes in a quick and efficient manner.

Coupling and conjugation techniques exist for generating antibody drug conjugates and in vivo targeting technologies. One such method is chemical cross-linking however this is labour intensive as the relevant proteins may need to be purified from homodimers and other undesirable by-products. In addition, the chemical modification steps can alter the integrity of the proteins, thus leading to poor stability or altered biological function. As a result, the production of bispecific antibodies by chemical cross-linking is often inefficient and can also lead to a loss of antibody activity.

Another method of manufacturing bispecific antibodies is by cell-fusion (e.g. hybrid hybridomas), wherein the engineered cells express two heavy and two light antibody chains that assemble randomly. Since there are 4 possible variants to choose from, this results in the generation of 10 possible bispecific antibody combinations, of which only some (in many cases, only one) combinations would be desired. Hence, generating bispecific antibodies by cell-fusion results in low production yields and also requires an additional purification step in order to isolate the desired bispecific antibodies from the other bispecific antibodies produced. These disadvantages increase both time and costs.

Recombinant DNA techniques have also been employed for generating bispecific antibodies. For example, recombinant DNA techniques have also been used to generate 'knob into hole' bispecific antibodies. The 'knob into hole' technique involves engineering sterically complementary mutations in multimerization domains at the CH3 domain interface (see e.g., Ridgway et al., Protein Eng. 9:617-621 (1996); Merchant et al., Nat. Biotechnol. 16(7): 677-81 (1998); see also U.S. Pat. Nos. 5,731,168 and 7,183,076). One constraint of this strategy is that the light chains of the two parent antibodies have to be identical to prevent mispairing and formation of undesired and/or inactive molecules when expressed in the same cell. Each bispecific (heavy and light chains thereof) must be expressed in a single cell and the protein product generally contains about 20% of homodimer, which is subsequently removed by purification.

Other approaches are based on the natural exchange of chains in full-length IgG4 molecules (Genmab Dubody). However, this approach also has difficulties because it does not allow a construct to be prepared without an Fc region. As the Fc region can contribute to biological activity it may be difficult to establish if an activity observed is based on the combination of variable regions, the Fc or both in bispecific molecules comprising an Fc when such molecules are tested in complex functional assays. Furthermore, the exchange is a dynamic process and this may lead to difficulties in relation to what the active species is within a given sample.

Thus there is a need for new methods which address the technical issues discussed above and allow an optimised way to identify cell populations based on their secreted product substances.

SUMMARY OF INVENTION

Thus provided a method for identifying or characterising a population of cells, for example in relation to a soluble molecule or molecules secreted by the cell, wherein the method employs a heterodimerically-tethered bispecific protein complex of formula A-X:Y-B, wherein:
  A-X is a first fusion protein;
  Y-B is a second fusion protein;
  X:Y is a heterodimeric-tether;
  : is a binding interaction between X and Y;
  A is a first protein component of the bispecific protein complex selected from an antibody or binding fragment thereof, or an antigen (including for example a protein ligand);
  B is a second protein component of the multispecific protein complex selected from an antibody or binding fragment, or an antigen (including for example a protein ligand);
  X is a first binding partner of a binding pair independently selected from an antigen or an antibody or binding fragment thereof; and
  Y is a second binding partner of the binding pair independently selected from an antigen or an antibody or a binding fragment thereof;
  wherein A is specific to a cell surface protein, for example a cell surface marker, and
  B captures (for example binds) a soluble molecule of interest secreted from the cell, with the proviso that when X is an antigen Y is an antibody or binding fragment thereof specific to the antigen represented by X and when Y is an antigen X is an antibody or binding fragment thereof specific to the antigen represented by Y, said method comprising the steps of:
    i) introducing to cells for analysis a combination of the fusion proteins A-X and B-Y in an uncomplexed form or in a heterodimerically-tethered bispecific protein complex form, and
    ii) detecting the capture (for example binding) of a soluble molecule of interest by component A or B.

Within the present disclosure, the fusion proteins' terms "A-X" and "Y-B" may be analogously indicated as "X-A" or "B-Y". The same applies to term for the heterodimeric-tether "X:Y" which can also be indicated herein as "Y:X".

In one embodiment the soluble molecule of interest captured by B is selected from the group comprising hormones, cytokines, chemokines, chemoattractants, leukotrienes, prostaglandins, vasoactive amines, enzymes, complement and fragments of complement, lipids, sphingolipids, second messenger components (for example; nitric oxide, cyclic AMP etc.), vitamins, minerals, cations, anions, sugars, clotting factors, acute phase proteins, gamma globulins (including immunoglobulins), albumins, soluble cell membrane receptors, splice variants of cell expressed proteins, nucleic acids, small membrane vesicles (such as exosomes, microvesicles, liposomes etc.), secretory peptides, immune complexes and intracellular proteins from dead or dying cells.

A cell may secret one or more cytokines. Thus in one embodiment the cytokine is, for example IL-1a, IL-1b, IL-1Ra, IL-2, IL-3, IL-4, IL-5, IL-6, IL-7, IL-9, IL-10, IL-11, IL-12, IL-13, IL-14, IL-15 IL-16, IL-17A, IL-17B, IL-17C, IL-17D, IL-17F, IL-18, IL-19, IL-20, IL-21, IL-22, IL-23, IL-24, IL-25, IL-26, IL-27, IL-28, IL-29, IL-30, IL-31, IL-32, IL-3, IL-34, IL-35, IL-36a, IL-36b, IL-36g, IL-37a, IL-37, IL-38, TNSF1, TNFSF2, TNFSF3, TNFSF4, TNFSF5, TNFSF6, TNFSF7, TNFSF8, TNFSF9, TNFSF10, TNFSF11, TNFSF12, TNFSF13, TNFSF13b, TNFSF14, TNFSF15, TNFSF18, IFNa, IFNb, IFNe, IFNk, IFNw, IFNg, IFN11, IFN12, IFN12, CSF1, CSF2, CSF3, TGFb1, TGFb2, TGFb3, CLC, CNTF, Leptin, OPG, LIF, Neuropoietin, Oncostain M, NGF, BDNF, NT-3, PAI-1, RBP4, Adiponectin, Apelin, Chimerin, Visfatin, Sclerostin and DKK-1.

The bispecific complexes of the present disclosure may be employed for the detection of cytokine producing cells for isolation, examination, for neutralisation, targeting and/or for modulation of cellular function or health. This has many applications, for example it is thought that some cytokine producing cells have a deleterious function in lung disease, such as asthma, for example by secreting one or more cytokines selected from the group IL-17, IL-13 and IL-5.

In one embodiment the soluble molecule of interest is a chemokine, for example selected from the group comprising CCL1, 2, 3, 4, 5, 6, 7, 8, 9/10, 11, 12, 13, 14, 15, 16, 17, 18, 19, 20, 21, 22, 23, 24, 25, 26, 27, 28, CXCL 1, 2, 3, 4, 5, 6, 7, 8, 9, 10, 11, 12, 13, 14, 15, 16, 17, XCL1, XCL2 and CX3CL1.

In one embodiment the soluble secreted molecule is an immunoglobulin, for example a particular isotype of immunoglobulin, for example B is specific for the constant region of an antibody light chain or a constant region of an antibody heavy chain, of an immunoglobulin secreted by the cell. Thus in one embodiment B is specific to a particular antibody isotype, for example selected from the group comprising IgG1, IgG2, IgG3, IgG4, IgA1, IgA2, IgE IgM and fragments thereof.

Generally if B is specific to the immunoglobulin secreted from the cell, for example B is an antibody or binding fragment specific to an epitope in the constant region of the secreted immunoglobulin (such as CL or CH1), then A will generally be directed to (or specific to) a cell surface marker other than that specific immunoglobulin.

Thus the method of the present disclosure can be used to detect and/or quantify the class of secreted immunoglobulin (for example distinguishing IgG1, IgG2, IgG3 and IgG4 subclasses) or fragments thereof, such as heavy chain or light chain components. This can allow the enumeration and detection of plasma cells using the A-X: B-Y complex.

Thus the present method can be applied to the isolation of immunoglobulin subclass specific responses for example the specific capture of IgG4 to the exclusion of other subclasses of IgG which may prove useful in the detection of patient populations with IgG4-linked diseases.

Alternatively, B may be antigen which is capable of specifically binding to the binding domain of an immunoglobulin secreted from the cell, for example it is an antigen that specifically binds the immunoglobulin secreted by the cell. In one embodiment B is an antigen selected from a group comprising but not exclusively autoantigens, tumour antigens, infectious agents, haptens or carriers which includes whole proteins or peptide fragments thereof.

The present method may also be employed for the detection of antibody producing cells for isolation, examination or targeting, for example autoantibody or pathogen-specific antibody producing plasma cells (especially in the case of surface IgG negative cells).

In one embodiment A binds a cell surface marker which is selected from the group comprising a stably expressed cell lineage marker and a marker stably expressed on non-lineage cells (that is cells which are not stained by antigens to a lineage maker).

In one embodiment the cell marker is selected from any cell surface receptor that characterises a cell set or sub-set of interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

In one embodiment the cell marker is selected from a marker for antibody secreting cell (such as B cell including a plasma cell) or T cell marker.

In one embodiment the B cell marker is independently selected from the group comprising CD19, CD20, CD21, CD22, CD23, CD24, CD27, CD35, CD38, CD40, B220 (also known as CD45), CD43, CD81, CD138, CXCR4, BCMA and IL-6R, for example CD38, CD138, CD45, CD27, CD19 or CD20, such as CD38 or CD138.

In one embodiment an immunoglobulin expressed on the surface of a B cell is employed as a marker for an antibody secreting cell (such as a B cell marker and/or plasma cell marker), for example the B cell marker is a constant region of an antibody light chain or a constant region of an antibody heavy chain, expressed as part of an immunoglobulin on the surface of the cell.

Thus in one embodiment A is specific to a particular antibody isotype, for example selected from the group comprising IgG1, IgG2, IgG3, IgG4, IgA, IgE, IgM and fragments thereof. These markers may be particularly useful for identifying class switched antibodies.

Generally both A and B will not both be specific to an immunoglobulin at the same time within one bispecific protein complex.

Thus in one embodiment the method employs docking the A-X to a cell surface marker whilst the other arm B-Y is employed to capture secreted immunoglobulin.

Thus in another embodiment the cell surface marker stably expressed on non-lineage cells is for example CD45 and the protein component A-X is specific to CD45 via the A moiety, whilst B in the other arm B-Y is employed to capture secreted immunoglobulin.

In one embodiment A is specific to a T cell surface marker, for example selected from the group comprising CD2, CD3, CD4, CD5, CD6, CD7, CD8, CD25, CD127 CD196 (CCR6), CD197 (CCR7), CD62L, CD69 and CD45.

T cells can be categorised into different populations based on the different levels of expression of surface markers, for example CD3, CD4, CD8, CD25, CD127 and CD196 (CCR6) and combinations thereof. However, important information about the T cells status can be obtained by analysing the surface expression of one or more of the markers CD197 (CCR7), CD62L, CD69 and CD45.

T lymphocytes are generally at least positive for CD45 and CD3

Cytotoxic T cells may be positive for the makers CD45, CD3 and CD8.

Regulatory T cells may be positive to the markers CD4, CD25 and Foxp3.

T helper cells may be positive for CD45, CD3 and CD4.

Thus it envisaged in the present disclosure that a first selection is performed with a bispecific protein complex (or components thereof) according to the present disclosure, for example with A specific to a marker selected from CD2, CD3, CD4, CD5, CD6, CD7, CD8, CD25, CD127 CD196

(CCR6), CD197 (CCR7), CD62L, CD69 and CDR0, and a second selection is performed with a bispecific protein complex (or components thereof) according to the present disclosure, for example with A specific to a marker selected from CD197 (CCR7), CD62L, CD69 and CD45.

Natural killer cells may be positive for the makers CD16, CD56, CD31, CD30, CD38 CD94, CD96, CD158, CD159, CD162R, CD223, CD244 and negative for CD3.

Monocyte/myeloid cell or monocyte/myeloid cell subsets antigens expressed, either as whole proteins or smaller peptides of the whole proteins, on such cells can be but are not limited to CDw12, CD13, CD14, CD33, CD64, CD11, CD112, CD115, CD163, CD204 etc.

Dendritic cell or dendritic subsets antigens expressed, either as whole proteins or smaller peptides of the whole proteins, on such cells can be but are not limited to CD85, CD205, CD209 etc.

Neutrophil cell or neutrophil subset antigens expressed, either as whole proteins or smaller peptides of the whole proteins, on such cells can be but are not limited to CD66a, CD66c, CD170 etc.

Basophil cell or basophil subset antigens expressed, either as whole proteins or smaller peptides of the whole proteins, on such cells can be but are not limited to surface IgE, CD123, CD203e, FceR1a etc.

Eosinophil cell or eosinophil subset antigens expressed, either as whole proteins or smaller peptides of the whole proteins, on such cells can be but are not limited to siglec-8, CD294 etc.

Mast cell or mast subset antigens expressed, either as whole proteins or smaller peptides of the whole proteins, on such cells can be but are not limited to surface IgE, FceR1a, CD117 etc.

Platelets/megakaryocytes or platelet/megakaryocyte subset antigens expressed, either as whole proteins or smaller peptides of the whole proteins, on such cells can be but are not limited to CD41, CD42a/b/c/d, CD51, CD110 etc.

Haematopoietic progenitor cells or haematopoietic progenitor cell subset antigens expressed, either as whole proteins or smaller peptides of the whole proteins, on such cells can be but are not limited to CD34, CD46, CD55, CD90, CD100, CD117, CD123, CD127, CD243, CD338, SSEA-3, SSEA-5, TRA-1-81, TRA-2-49, TRA-2-54 etc.

A surface marker on all tissues or cellular subsets that include brain/nervous system, endocrine system, blood/immune system, liver, kidney, heart and skeletal muscle, skin/bones/joints, gastrointestinal tract, lungs, male tissues and female tissues.

A surface marker where the cell expresses a tumour antigen, for example selected from a list including erbB-2, CEA, NCAM, GD2, CD33, CD44, CD70, EpCAM, CD19, CD20, KDR, Tag-72 etc.

In one embodiment more than two selections are employed.

In one embodiment the first selection is performed before the second selection is performed (i.e. the selections are performed sequentially).

In one embodiment the first selection and the second selection is performed at the same time, for example as a multiplex, and different labels, such as different fluorophores are employed for the two or more selections. Advantageously, when the selections are performed as a multiplex the desired population of cell can be isolated in essentially one step.

Thus in one embodiment the bispecific protein complexes of the present disclosure can be used for the identification of cell populations based on their secretion phenotype. An example of this is be the capture of IL-17 on CD4 positive T cells to identify or isolate T helper 17 cells which have been associated with the onset and maintenance of autoimmunity.

Whilst not wishing to be bound by theory it is thought CD4 and CXCR3 and/or CD4 and CXCR5 expression may be distorted in autoimmune disease. CD4 and CCR6 expression may be distorted in organ specific autoimmune disease. CD8 expression may be distorted in GVHD. CD4, CCR4, Crth2 expression may be distorted in allergy and asthma.

The antibody format of the disclosure is such that the bispecific protein complexes can be readily assembled and these can be used to screen patients (and ex vivo samples therefrom, such as a blood sample) to gain insights into the disease mechanisms and/or prognosis and/or to defined patient sub-groups and/or to assign a patient to a sub-group.

The antibody complexes of the present disclosure can be prepared rapidly to include a single domain antibody sdAb as A, specific for cell surface marker by which to anchor the complex on the surface of the requisite cell in combination with a further sdAb as B specific to:

a soluble factor secreted from the cell, or an antigen.

Thus the bi/multispecific formats according to the disclosure are useful in the detection, identification, isolation, separation characterisation and/or quantification of the cells and cell populations.

In one embodiment A is independently selected from an antigen, ligand, receptor, a full length antibody, a Fab fragment, a Fab' fragment, a sdAb, a VH, a VL and a scFv, such as full length antibody, a Fab fragment, a Fab' fragment, a sdAb, a VH, a VL and a scFv, in particular a Fab, scFv or sdAb.

In one embodiment protein component A is a protein, for example a ligand to a receptor expressed on the surface of the cell.

Preferably, A is a scFv or a Fab fragment.

In one embodiment protein component B is independently selected from an antigen, ligand, receptor a full length antibody, a Fab fragment, a Fab' fragment, a sdAb, a VH, a VL and a scFv, such as full length antibody, a Fab fragment, a Fab' fragment, a sdAb, a VH, a VL and a scFv, in particular a Fab, scFv or sdAb.

It should be understood that the present method may also be employed in such situations when the antibody or binding fragment represented by the protein component A or B binds an antigen which is also bound by the soluble molecule of interest secreted by the cell, for example as shown in FIGS. 3 and 4.

Preferably, B is a scFv or a Fab fragment.

In one embodiment protein component B is a protein, for example a ligand or soluble receptor.

In one embodiment component B is an antigen which can directly capture the soluble molecule of interest, for example as shown in FIG. 7.

In one embodiment X is fused, optionally via a linker, to the C-terminal of the protein component A, for example, to the C-terminal of the heavy chain of an antibody or binding fragment thereof, such as the C-terminal of the heavy chain in a Fab fragment or Fab' fragment represented by A.

In one embodiment X is fused, optionally via a linker, to the C-terminal of the light chain of an antibody or binding fragment thereof, such as a Fab fragment or Fab' fragment represented by A.

In one embodiment X is connected via a linker, in particular a linker disclosed herein In one embodiment Y is fused, optionally via a linker, to the C-terminal of the protein component B, to the C-terminal of the heavy chain of an antibody or binding fragment thereof, such as a heavy chain in a Fab fragment or Fab' fragment represented by B.

In one embodiment Y is fused, optionally via a linker, to the C-terminal of a light chain in a Fab fragment or Fab' fragment represented by B.

In one embodiment X is fused, optionally via a linker, to the N-terminal of a scFv or the N-terminal of the heavy chain in the Fab fragment or Fab' fragment, whichever is represented by A.

In one embodiment Y is fused, optionally via a linker, to the N-terminal of the scFv represented by B.

In one embodiment the variable X is an antibody binding fragment such as a Fab fragment, a Fab' fragment, scFv, Fv, VH, VL or sdAb (in particular a Fab, scFv or sdAb) and Y variable is an antigen, such as a peptide.

In one embodiment the variable Y is an antibody binding fragment such as a Fab fragment, a Fab' fragment, scFv, Fv, VH, VL or sdAb (in particular a Fab, scFv or sdAb) and X is an antigen, such as a peptide.

In one embodiment the variable X or Y is a Fab fragment, a Fab' fragment, a scFv, or sdAb and the other variable is a peptide, for example a Fab fragment, a Fab' fragment, a scFv, or sdAb specific to the peptide GCN4 (SEQ ID NO:1 or amino acids 1 to 38 of SEQ ID NO:1).

In one embodiment the variable X or Y is a scFv or sdAb and the other variable is a peptide.

In one embodiment X or Y is a scFv 52SR4 (SEQ ID NO:3 or amino acids 1 to 243 of SEQ ID NO:3, 99 or 100 as shown in Table 1A). It will be appreciated that where X or Y is a Fab or Fab' fragment which binds GCN4 it may comprise the VH and VL regions from scFv 52SR4.

In one embodiment X is independently selected from a scFv, a sdAb and a peptide, with the proviso that when X is a peptide Y is an antibody or binding fragment thereof, such as a scFv or sdAb and when X is a scFv or sdAb then Y is an antigen, such as a peptide.

In one embodiment Y is independently selected from a scFv, a sdAb and a peptide, with the proviso that when Y is a peptide X is an antibody or binding fragment, such as a scFv or sdAb and when Y is a scFv or a sdAb then X is an antigen, such as a peptide.

In one embodiment X or Y is is a peptide GCN4 (SEQ ID NO:1 or amino acids 1 to 38 of SEQ ID NO:1) or an epitope fragment thereof. The nucleotide sequence encoding the GCN4 peptide according to SEQ ID NO: 1 is shown in SEQ ID NO: 1A as SEQ ID NO: 2 (Table 1A).

TABLE 1A

| | |
|---|---|
| GCN4(7P14P)<br>SEQ ID NO: 1 | ASGGGRMKQLEPKVEELLPKNYHLENEVARLKKLVGERHHHHHH |
| GCN4 (7P14P)<br>SEQ ID NO: 2 | GCTAGCGGAGGCGGAAGAATGAAACAACTTGAACCCAAGGTTGAAGAATTGCTT<br>CCGAAAAATTATCACTTGGAAAATGAGGTTGCCAGATTAAAGAAATTAGTTGGC<br>GAACGCCATCACCATCACCATCAC |
| 52SR4 ds<br>scFv<br>SEQ ID NO: 3 | DAVVTQESALTSSPGETVTLTCRSSTGAVTTSNYASWVQEKPDHLFTGLIGGTN<br>NRAPGVPARFSGSLIGDKAALTITGAQTEDEAIYFCVLWYSDHWVFGCGTKLTV<br>LGGGGGSGGGGSGGGGSGGGGSDVQLQQSGPGLVAPSQSLSITCTVSGFLLTDY<br>GVNWVRQSPGKCLEWLGVIWGDGITDYNSALKSRLSVTKDNSKSQVFLKMNSLQ<br>SGDSARYYCVTGLFDYWGQGTTLTVSSAAAHHHHHHEQKLISEEDL |
| 52SR4 ds scFv<br>SEQ ID NO: 4 | GATGCGGTGGTGACCCAGGAAAGCGCGCTGACCAGCAGCCCGGGCGAAACCGTG<br>ACCCTGACCTGCCGCAGCAGCACCGGCGCGGTGACCACCAGCAACTATGCGAGC<br>TGGGTGCAGGAAAAACCGGATCATCTGTTTACCGGCCTGATTGGCGGCACCAAC<br>AACCGCGCGCCGGGCGTGCCGGCGCGCTTTAGCGGCAGCCTGATTGGCGATAAA<br>GCGGCGCTGACCATTACCGGCGCGCAGACCGAAGATGAAGCGATTTATTTTGC<br>GTGCTGTGGTATAGCGACCATTGGGTGTTTGGCTGCGGCACCAAACTGACCGTG<br>CTGGGTGGAGGCGGTGGCTCAGGCGGAGGTGGCTCAGGCGGTGGCGGGTCTGGC<br>GGCGGCGGCAGCGATGTGCAGCTGCAGCAGAGCGGCCCGGGCCTGGTGGCGCCG<br>AGCCAGAGCCTGAGCATTACCTGCACCGTGAGCGGCTTTCTCCTGACCGATTAT<br>GGCGTGAACTGGGTGCGCCAGAGCCCGGGCAAATGCCTGGAATGGCTGGGCGTG<br>ATTTGGGGCGATGGCATTACCGATTATAACAGCGCGCTGAAAAGCCGCCTGAGC<br>GTGACCAAAGATAACAGCAAAAGCCAGGTGTTTCTGAAAATGAACAGCCTGCAG<br>AGCGGCGATAGCGCGCGCTATTATTGCGTGACCGGCCTGTTTGATTATTGGGGC<br>CAGGGCACCACCCTGACCGTGAGCAGCGCGGCCGCCCATCACCATCACCATCAC<br>GAACAGAAACTGATTAGCGAAGAAGATCTGTAATAG |
| SEQ ID NO: 99 | DAVVTQESALTSSPGETVTLTCRSSTGAVTTSNYASWVQEKPDHLFTGLIGGTN<br>NRAPGVPARFSGSLIGDKAALTITGAQTEDEAIYFCVLWYSDHWVFGCGTKLTV<br>LGGGGSGGGGSGGGGSGGGGSDVQLQQSGPGLVAPSQSLSITCTVSGFLLTDY<br>GVNWVRQSPGKCLEWLGVIWGDGITDYNSALKSRLSVTKDNSKSQVFLKMNSLQ<br>SGDSARYYCVTGLFDYWGQGTTLTVSS |
| SEQ ID NO: 100 | DVQLQQSGPGLVAPSQSLSITCTVSGFLLTDYGVNWVRQSPGKCLEWLGVIWGD<br>GITDYNSALKSRLSVTKDNSKSQVFLKMNSLQSGDSARYYCVTGLFDYWGQGTT<br>LTVSSPARFSGSLIGDKAALTITGAQTEDEAIYFCVLWYSDHWVFGCGTKLTVL<br>GGGGGSGGGGSGGGGSGGGGSDAVVTQESALTSSPGETVTLTCRSSTGAVTTSN<br>YASWVQEKPDHLFTGLIGGTNNRAPGVPARFSGSLIGDKAALTITGAQTEDEAI<br>YFCVLWYSDHWVFGCGTKLTVL |
| SEQ ID NO: 101 | MSVPTQVLGLLLLWLTDARC |
| SEQ ID NO: 102 | MEWSWVFLFFLSVTTGVHS |

TABLE 1A-continued

| SEQ ID NO: 103 | MDWLWTLLFLMAAAQSAQA |
| --- | --- |
| SEQ ID NO: 104 | MGWSWTFLFLLSGTSGVLS |

Other variants of the GCN4 peptides are shown in Table 1B (SEQ ID NO: 75-97), wherein the amino acids in bold are optional and the amino acids in italics form the sequence of the linker.

TABLE 1B

| SEQ ID NO: 76 | *GGGGSGGGGSGGGGSGGGGS*YHLENEVARLKKLVGERHHHHHH |
| --- | --- |
| SEQ ID NO: 77 | *GGGGSGGGGSGGGGSGGGGS*YHLENEVARLKALVGERHHHHHH |
| SEQ ID NO: 78 | *GGGGSGGGGSGGGGSGGGGS*YHLENEVARLAKLVGERHHHHHH |
| SEQ ID NO: 79 | *GGGGSGGGGSGGGGSGGGGS*YHLENEVARLQKLVGERHHHHHH |
| SEQ ID NO: 80 | *GGGGSGGGGSGGGGSGGGGS*YHLENEVARLNKLVGERHHHHHH |
| SEQ ID NO: 81 | *GGGGSGGGGSGGGGSGGGGS*YHLENEVARLAALVGERHHHHHH |
| SEQ ID NO: 82 | *GGGGSGGGGSGGGGSGGGGS*YHLENEVARLQALVGERHHHHHH |
| SEQ ID NO: 83 | *GGGGSGGGGSGGGGSGGGGS*YHLENEVARLNALVGERHHHHHH |
| SEQ ID NO: 84 | *ASGGG*AMKQLEPKVEELLPKNYHLENEVARLKKLVGERHHHHHH |
| SEQ ID NO: 85 | *ASGGG*RMKQLEPKVEELLPKNYHLENEVARLKALVGERHHHHHH |
| SEQ ID NO: 86 | *ASGGG*AMKQLEPKVEELLPKNYHLENEVARLKALVGERHHHHHH |
| SEQ ID NO: 87 | *ASGGG*RMKQLEPKVEELLPKNYHLENEVARLAKLVGERHHHHHH |
| SEQ ID NO: 88 | *ASGGG*RMKQLEPKVEELLPKNYHLENEVARLQKLVGERHHHHHH |
| SEQ ID NO: 89 | *ASGGG*RMKQLEPKVEELLPKNYHLENEVARLNKLVGERHHHHHH |
| SEQ ID NO: 90 | *ASGGG*AMKQLEPKVEELLPKNYHLENEVARLAKLVGERHHHHHH |
| SEQ ID NO: 91 | *ASGGG*AMKQLEPKVEELLPKNYHLENEVARLQKLVGERHHHHHH |
| SEQ ID NO: 92 | *ASGGG*AMKQLEPKVEELLPKNYHLENEVARLNKLVGERHHHHHH |
| SEQ ID NO: 93 | *ASGGG*RMKQLEPKVEELLPKNYHLENEVARLAALVGERHHHHHH |
| SEQ ID NO: 94 | *ASGGG*RMKQLEPKVEELLPKNYHLENEVARLQALVGERHHHHHH |
| SEQ ID NO: 95 | *ASGGG*RMKQLEPKVEELLPKNYHLENEVARLNALVGERHHHHHH |
| SEQ ID NO: 96 | *ASGGG*AMKQLEPKVEELLPKNYHLENEVARLAALVGERHHHHHH |
| SEQ ID NO: 97 | *ASGGG*AMKQLEPKVEELLPKNYHLENEVARLQALVGERHHHHHH |
| SEQ ID NO: 98 | *ASGGG*AMKQLEPKVEELLPKNYHLENEVARLNALVGERHHHHHH | fusion. Preferred signal peptide sequences are shown in Table 1A with SEQ ID NOs: 101-104.

In one embodiment X is connected via a linker, in particular a linker disclosed herein.

It should be understood that A-X and Y-B fusions may be generated in various orientations which means that the polynucleotide constructs encoding such fusion may be designed to express X or A in both orientations (A-X where A's C-terminal is fused to X's N-terminal or X-A where X's C-terminal is fused to A's N-terminal). The same applies to the Y-B fusion. Irrespective of whether A, X, Y or B is at the N-terminal of the fusion, the polynucleotide sequence to generate such fusions will comprise a nucleotide sequence designed to encode a signal peptide sequence, at the very N-terminal of the fusion, for assisting extracellular release. The signal peptide is ultimately cleaved from the mature fusion.

In one embodiment Y is connected via a linker, in particular a linker disclosed herein.

In one embodiment the linker is selected from AAASGGG SEQ ID NO: 74, ASGGG SEQ ID NO: 73, ASGGGG SEQ ID NO: 71, SGGGGSGGGGSGGGGS SEQ ID NO: 18, and SGGGGSGGGGSGGGGSGGGS SEQ ID NO: 75.

When A or B is a Fab and the corresponding X or Y is a peptide then the linker to the respective X or Y may, for example be ASGGG or ASGGGG or AAASGGG SEQ ID NO: 72.

When A or B is a scFv and the corresponding X or Y is a peptide then the linker may, for example be ASGGG or ASGGGG or AAASGGG.

When A or B is a scFv and the corresponding X or Y is a scFv or sdAb then the linker may, for example be selected from SGGGGSGGGGSGGGGS and SGGGGSGGGGSGGGGSGGGS.

In one embodiment X or Y is a peptide in the range 5 to 25 amino acids in length. In one embodiment the binding affinity between X and Y is 5 nM or stronger, for example 900 pM or stronger, such as 800, 700, 600, 500, 400 or 300 pM.

The bispecific protein complexes of the present disclosure are suitable for use in screening because there is no difficulty expressing the unit A-X or the unit B-Y. The amount of purification required after expression of each unit (A-X or B-Y) is minimal or in fact, unnecessary. The bispecific complex can be formed in a 1:1 molar ratio by simply admixing the relevant units i.e. without recourse to conjugation and coupling chemistry. The binding partners X and Y drive the equilibrium in favour of forming the requisite heterodimer bispecific complex. Again little or no purification is required after formation of the complex after heterodimerisation. Thus large number of A-X and B-Y can be readily prepared and combined.

In one embodiment A and/or B comprise an Fc region.

In one embodiment the A and/or B in the constructs of the present disclosure lack an Fc region.

In one embodiment one or more scFvs employed in the bispecific protein complex according to the present disclosure is disulfide stabilised.

The ability to prepare and screen a bispecific complex lacking the Fc fragment CH2-CH3 also ensures that the biological activity observed is in fact due solely to the variable region pairs in the complex. The simplicity of the bispecific complex of the invention and the methods of preparing it are a huge advantage in the context of rapid and extensive screening for characterisations, isolation purposes, etc.

In one embodiment the capture of a soluble molecule of interest by protein component B is detected employing a labelled protein. The label protein may be an antigen, an antibody or a binding fragment thereof, such as a full-length antibody.

In one embodiment the heterodimerically-tethered bispecific protein complex A-X:Y-B is prepared by mixing A-X and B-Y in vitro before introducing the complex to the cells for analysis. Thus in one embodiment the method comprises an in vitro mixing step bringing A-X and B-Y into contact.

In one embodiment the components A-X and B-Y are introduced as separate fusion proteins but at approximately the same time to the cells for analysis and come together to form the complex A-X:Y-B after their addition to the sample of cells.

In one embodiment A-X or B-Y is first added to the cells for analysis and later the corresponding reagent, respectively B-Y and A-X is added. The time difference may be, for example 15 mins to 24 hours. Only after addition of the second fusion protein does the complex A-X:Y-B form.

In one embodiment multiple bispecific protein complexes according to the present disclosure are employed in parallel, for example A may have a fixed specificity and a variety of B-X with different specificity in the protein component B are employed. Alternatively, B may have fixed specificity and the specificity of A may be varied. Alternatively, A and B may both be varied.

In one embodiment the method of the present disclosure is performed in a grid format.

In one embodiment the method of the present disclosure is performed in a multiplex format.

In one embodiment the method of the present disclosure is ex vivo/in vitro.

Thus in one embodiment the fusion proteins A-X and B-Y are not co-expressed in the same cell. This is advantageous because it allows, for example 100 fusion proteins to expressed and optionally purified and the subsequent mixing of the 100 fusion proteins in the various permutations can provide 10,000 heterodimerically-tethered bispecific protein complexes, of which 5,000 are unique pairs.

In contrast certain prior art methods require co-expression of bispecifics and thus for 10,000 complexes, 10,000 transfections, expressions and purifications are required.

However, an obvious alternative, which is technically more challenging, comprises expressing A-X and B-Y in the same cell.

Advantageously, this means that the fusion proteins A-X and Y-B can be readily assembled into a bispecific protein complex simply by mixing the fusion proteins together. Thus the bispecific protein complex of the present disclosure has a modular structure which allows for two different proteins to be easily assembled in order to produce large panels of permutations of bispecific protein complexes with different combinations of antigen binding specificities in, for example a grid-like fashion. This allows for the efficient and systematic screening of a large number of bispecific protein complexes in order to detect additive, synergistic or novel biological function.

Given X and Y are specific for each other this significantly reduces the ability to form homodimers. X and Y are collectively referred to herein as a binding pair or binding partners. In one embodiment X does not have high affinity for other Xs. In one embodiment Y does not have high affinity for other Ys. Advantageously, X and Y do not form homodimers, this prevents the formation of undesired monospecific protein complexes, increases yield of the desired bispecific protein complexes, and removes the need for onerous purification steps to remove the monospecific protein complexes.

This allows rapid assembly of bispecific protein complexes with a yield and/or purity which cannot be obtained efficiently by most prior art methods, in particular prior art methods generally require extensive purification steps. The yield of bispecific complex is typically 75% or higher in the present invention.

Furthermore multiple binding regions (such as variable regions) to a given antigen or epitope can be investigated in parallel to identify nuances in biological function. This allows combinations of variable region sequences directed to a given pair of antigens to be investigated and optimised.

Advantageously the X and Y components allow a multiplex comprising bispecific protein complexes made up of different permutations of fusion proteins to be assembled rapidly and easily.

The present method does not rely on pre-conceived ideas about biological functions. In addition, the present method, upon capturing of the soluble molecule of interest, may induce or prevent subsequent biological functions on the detected cell(s), such as inhibition of cell proliferation or induction of apoptosis.

Variations of these Figures are envisaged where the detection is a labelled protein, for example an antibody which binds part of protein component A or B.

Figure 6:
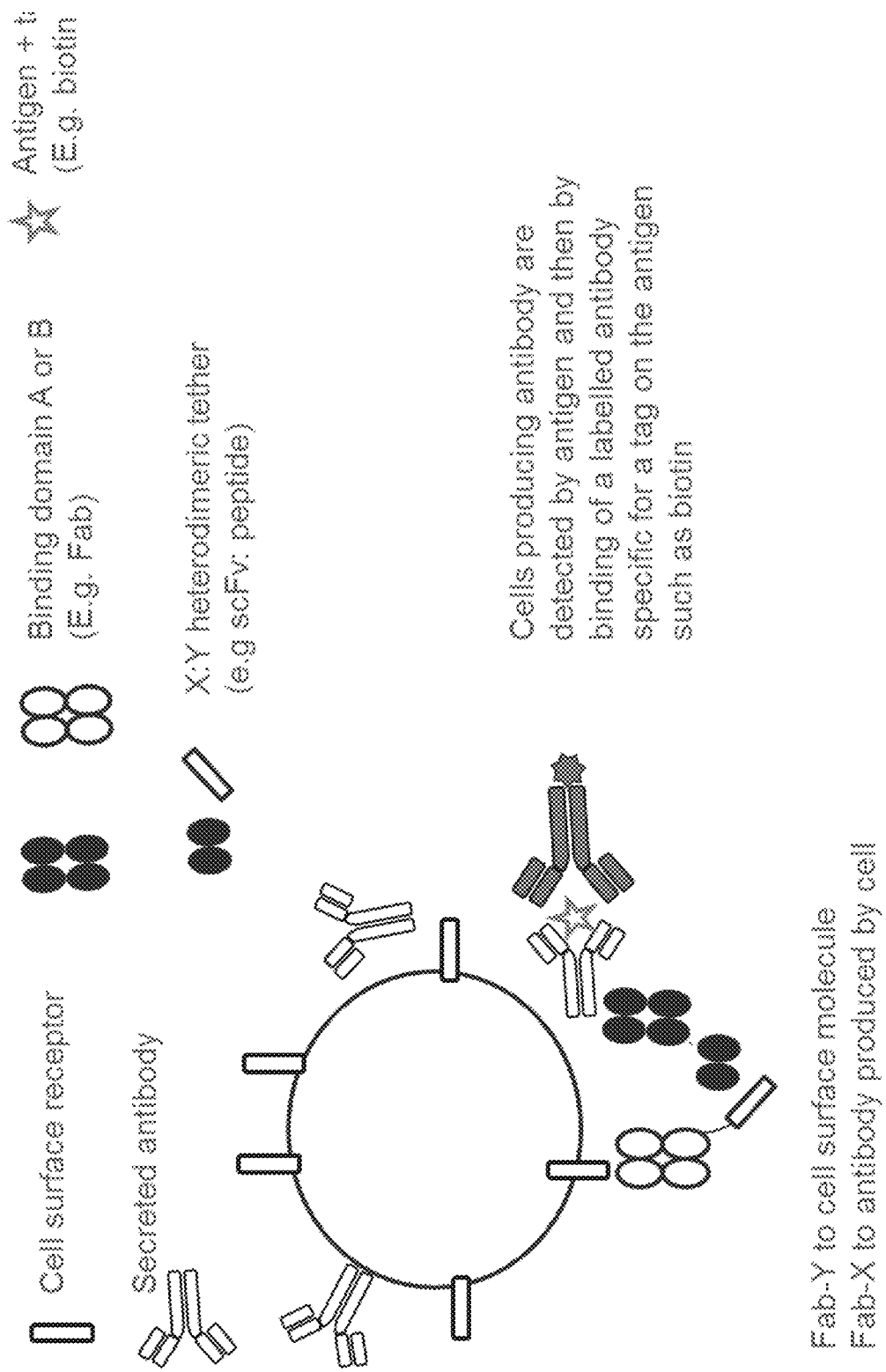
FIG. 6 shows a Fab-peptide (A-X respectively) in complex with to a scFv-Fab (Y-B respectively) wherein Fab A is bound to (specific to) a cell surface receptor and Fab B binds to (is specific to) and immunoglobulin secreted from the cell, and the detection system is a labelled antibody that binds, an antigen (also optionally labelled) which is also bound by the immunoglobulin secreted from the cell. That is the labelled antibody indirectly labels the secreted immunoglobulin.

Variations of these Figures are envisaged where the detection is a labelled protein, for example in FIG. 6, where labelled antigen is employed and then a further labelled antibody is necessarily employed.

DETAILED DESCRIPTION

"Bispecific protein complex" as used herein refers to a molecule comprising two proteins (A and B referred to herein as bispecific components also referred to herein as the first protein component and second protein component, respectively of the bispecific) which are retained together by a heterodimeric-tether. In one embodiment one or both of the proteins have a binding domain, for example one or both of the proteins are antibodies or fragments thereof (in particular a Fab or Fab' fragment).

"Fusion proteins" as employed herein comprise a protein component A or B fused to a binding partner X or Y (as appropriate). In one embodiment the fusion protein is a translational protein expressed by recombinant techniques from a genetic construct, for example expressed in a host from a DNA construct. In the context of the present disclosure one of the key characteristics of a fusion protein is that it can be expressed as a "single protein/unit" from a cell (of course in the case of fusion proteins comprising a Fab/Fab' fragment there will be two chains but this will be considered a single protein for the purpose of the present specification with one chain, typically the heavy chain fused at its C-terminus to X or Y as appropriate, optionally via a linker as described herein below).

The function of the heterodimeric tether X:Y is to retain the proteins A and B in proximity to each other so that synergistic function of A and B can be effected or identified, for example employing the method described herein.

"heterodimeric-tether" as used herein refers to a tether comprising two different binding partners X and Y which form an interaction: (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein.

In one embodiment "unsuitable for forming homodimers" as employed herein refers to formation of the heterodimers of X-Y are more preferable, for example more stable, such as thermodynamically stable, once formed than homodimers. In one embodiment the binding interaction between X and Y is monovalent.

In one embodiment the X-Y interaction is more favourable than the X-X or Y-Y interaction. This reduces the formation of homodimers X-X or Y-Y when the fusion proteins A-X and B-Y are mixed. Typically greater than 75% heterodimer is formed following 1:1 molar ratio mixing.

If desired, a purification step (in particular a one-step purification), such as column chromatography may be employed, for example to purify the fusion proteins and/or bispecific protein complexes according to the present disclosure.

In one embodiment a purification step is provided after expression for each fusion protein, although typically aggregate levels are low. Thus in one embodiment prior to in vitro mixing, the fusion protein(s) is/are provided in substantially pure form. Substantially pure form as employed herein refers to wherein the fusion protein is 90, 91, 92, 93, 94, 95, 96, 97, 98, 99 or 100% monomer.

In one embodiment no purification of the fusion protein or proteins is performed.

In one embodiment each fusion protein unit is expressed in a different expression experiment/run.

In one embodiment no purification of the fusion protein or proteins is performed before mixing to generate a bispecific protein complex. In one embodiment no purification of the fusion protein or proteins is performed before and/or after mixing.

In one embodiment no purification is required after the bispecific protein complex formation.

In one embodiment after mixing, and generally without further purification, at least 50% of the composition is the desired bispecific protein complex, for example at least 60, 65, 70, 75, 80% of the composition is the required bispecific protein complex.

In one embodiment the ratio of fusion proteins employed in the in vitro mixing step of the present method is A-X to B-Y 0.8:1 to 3:1, such as 1.5:1 or 2:1.

In one embodiment the ratio of fusion proteins employed in the in vitro mixing step of the present method is B-Y to A-X 0.8:1 to 3:1, such as 1.5:1 or 2:1, in a particular a molar ratio.

In one embodiment the ratio of A-X to B-Y employed in the in vitro mixing step is 1:1, in particular a 1:1 molar ratio.

The present disclosure also extends to a method of preparing a bispecific complex according to the present disclosure comprising admixing a fusion protein A-X and B-Y, for example in a 1:1 molar ratio.

In one embodiment the mixing occurs in vitro.

In one embodiment, the mixing occurs in a sample containing cells for analysis, i.e. the fusion proteins A-X and B-Y interact with each other within after introducing the individual fusion proteins.

In one embodiment, the mixing occurs in vivo, i.e. the fusion proteins A-X and B-Y interact with each other within a subject's body to form the heterodimeric-tether and in consequence, the bispecific protein complex.

In one embodiment, X and Y are completely specific for each other and do not bind to any other peptides/proteins in a cell or within a subject's body. This can be achieved for example by ensuring that X and Y are not naturally present in the target cell or in the target subject's body. This can be achieved, for example by selecting X or Y to be from a species or entity which is different to the subject (e.g. a yeast protein) and ensuring the other variable is specific to it. Advantageously, this prevents the binding of the fusion proteins A-X and/or B-Y to an undesired target, thereby generating unwanted off-target effects.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer, for example an amino acid sequence of the peptide binding partner is mutated to eliminate or minimise the formation of homodimers and a sdAb specific thereto is employed.

Incapable of forming homodimers or aggregates as employed herein, refers to a low or zero propensity to form homodimers or aggregate. Low as employed herein refers to 5% or less, such as 4, 3, 2, 1, 0.5% or less aggregate, for example after mixing or expression or purification.

Small amounts of aggregate in the fusion proteins or residual in the heterodimerically-tethered bispecific protein complex generally has minimal effect on the screening method of the present disclosure. Therefore, in one embodiment no purification of fusion protein(s) and/or bispecific protein complex(es) is/are employed in the method, in particular after the mixing step.

In one embodiment : is a binding interaction based on attractive forces, for example Van der Waals forces, such as hydrogen bonding and electrostatic interactions, in particular, based on antibody specificity for an antigen (such as a peptide).

In one embodiment : is a covalent bond formed from a specific chemical interaction, such as click chemistry. In one embodiment : is not a covalent bond. In one embodiment conjugation/coupling chemistry is not employed to prepare the bispecific protein complexes of the present disclosure.

"Form the complex" as employed herein refers to an interaction, including a binding interaction or a chemical reaction, which is sufficiently specific and strong when the fusion protein components A-X and B-Y are brought into contact under appropriate conditions that the complex is assembled and the fusion proteins are retained together.

"Retained together" as employed herein refers to the holding of the components (the fusion proteins) in the proximity of each other, such that after X:Y binding the complex can be handled as if it were one molecule, and in many instances behaves and acts like a single molecule. In one embodiment the retention renders the complex suitable for use in the method disclosed herein, i.e. suitable for use in at least one functional screen.

Specificity as employed herein refers to where, for example the partners in the interaction e.g. X:Y or A and antigen or B and antigen only recognise each other or have significantly higher affinity for each other in comparison to non-partners, for example at least 2, 3, 4, 5, 6, 7, 8, 9, 10 times higher affinity, than for example a background level of binding to an unrelated non partner protein.

Specificity in relation to X and Y as employed herein refers to where the binding partners X and Y in the interaction only recognise each other or have significantly higher affinity for each other in comparison to non-partners, for example at least 2, 3, 4, 5, 6, 7, 8, 9, 10 times higher affinity.

In one embodiment the binding interaction is reversible. In one embodiment the binding interaction is essentially irreversible.

Essentially irreversible as employed herein refers to a slow off rate (dissociation constant) of the antibody or binding fragment.

In one embodiment, the binding interaction between X and Y has a low dissociation constant. Examples of a low dissociation constant include $1\text{-}9\times10^{-2}$ $s^{-1}$ or less, for example $1\text{-}9\times10^{-3}$ $s^{-1}$, $1\text{-}9\times10^{-4}$ $s^{-1}$, $1\text{-}9\times10^{-5}$ $s^{-1}$, $1\text{-}9\times10^{-6}$ $s^{-1}$ or $1\text{-}9\times10^{-7}s^{-1}$. Particularly suitable dissociation constants include $2\times10^{-4}$ $s^{-1}$ or less, for example $1\times10^{-5}$ $s^{-1}$, $1\times10^{-6}$ $s^{-1}$ or $1\times10^{-7}s^{-1}$.

Whilst not wishing to be bound by theory it is thought that the low dissociation constant (also referred to as off rate) allows the molecules to be sufficiently stable to render the bispecific protein complex useful, in particular in functional screening assays.

In one embodiment, the affinity of X and Y for each other is 5 nM or stronger, for example 900 pM or stronger, such as 800, 700, 600, 500, 400, 300, 200, 100 or 50 pM or stronger.

Affinity is a value calculated from the on and off rate of the entity. The term "affinity" as used herein refers to the strength of the sum total of non-covalent interactions between a single binding site of a molecule (e.g. an antibody) and its binding partner (e.g. a peptide). The affinity of a molecule for its binding partner can generally be represented by the dissociation constant (KD). Affinity can be measured by common methods known in the art, including those described herein, such as surface plasmon resonance methods, in particular BIAcore.

However, the ability to hold the complex together is not just about affinity. Whilst not wishing to be bound by theory, we hypothesise that in fact there are three significant components: the on-rate, off-rate and the affinity. The calculation for affinity is based on on-rate and off-rate. So if the on-rate is low and the off-rate is fast, then the affinity will be low and that will not be sufficient to hold the bispecific protein complex together. However, a slow on-rate could be compensated for by a slow off-rate giving an overall suitable affinity.

In some embodiments a high on-rate may be sufficient to hold the complex together.

If the binding partners (X and Y) employed in the complex have a slow on-rate then additional time may be required after mixing the components to allow the complex to form.

If the affinity between the binding partners is sufficiently high, it may be possible for the bispecific protein complex to perform its desired biological function even if the affinity of the proteins (A and B) of the bispecific protein complex only bind weakly to their targets. Conversely, if the proteins (A and B) are able to bind strongly to their targets, it may be possible to achieve the same biological function even if the affinity of the binding partners (X and Y) for each other is lower. In other words, a 'trinity' relationship exists such that a higher affinity between the binding partners can compensate for a lower affinity for the targets and vice versa.

In one embodiment an interaction between a constant domain in a heavy chain, such as CH1 and a constant domain in a light chain, such as CKappa contribute to the formation and/or stability of a bispecific complex according to the present disclosure. Thus employing Fab or Fab' fragments in certain embodiments of the bispecific complexes of the present disclosure is beneficial.

In one embodiment the bispecific complex of the present disclosure does not comprise a component with an effector function, for example the complex does not comprise a constant domain other than a CH1 and CKappa or CLambda, in particular does not comprise constant domains independently selected from the group comprising CH2, CH3, CH4 and combinations thereof. In one embodiment the bispecific complex of the present disclosure lacks an Fc region.

Cell surface marker is a moiety, for example a protein expressed on the surface of the cell that be employed alone or in combination with other surface marker to identify and/or isolate the cell. The marker may be associated with the lineage of the cell or activation status of the cell, a molecule expressed by the cell or the like.

Soluble molecule of interest as employed herein refers to a molecule secreted by the cell, wherein said molecule in vivo does not precipitate after secretion. Examples of soluble molecules secreted by the cell are provide herein and include hormones, cytokines, chemokines, chemoattractants, leukotrienes, prostaglandins, vasoactive amines, enzymes, complement and fragments of complement, lipids, sphingolipids, second messenger components (for example; nitric oxide, cyclic AMP etc.), vitamins, minerals, cations, anions, sugars, clotting factors, acute phase proteins, gamma globulins (including immunoglobulins), albumins, soluble cell membrane receptors, splice variants of cell expressed proteins, nucleic acids, small membrane vesicles (such as exosomes, microvesicles, liposomes etc.), secretory peptides, immune complexes and intracellular proteins from dead or dying cells.

"Multiplex" as employed herein refers to combining multiple bispecific protein complexes according to the present disclosure in the same pot essentially simultaneously, for example such that the readout from the analysis of the same needs to be deconvoluted.

In one embodiment simultaneously refers to concomitant analysis where the signal output is analysed by an instrument at essentially the same time. This signal may require deconvolution to interpret the results obtained.

Advantageously, testing multiple bispecific protein complexes allows for more efficient screening of a large number of bispecific protein complexes for the identification of cells secreting molecules & hence of new and interesting biological mechanisms.

In one embodiment the multiplex comprises 2 to hundreds of thousands of heterodimerically-tethered bispecific protein complexes, for example 2 to 500,000 of said complexes, such as 2 to 100,000 or 2 to 10,000, in particular generated from mixing in a grid 2 to 100s of first and second fusion proteins (A-X and B-Y). In one embodiment the multiplex comprises for example 2 to 1,000, such as 2 to 900, 2 to 800, 2 to 700, 2 to 600, 2 to 500, 2 to 400, 2 to 300, 2 to 200, 2 to 100, 2 to 90, 3 to 80, 4 to 70, 5 to 60, 6 to 50, 7 to 40, 8 to 30, 9 to 25, 10 to 20 or 15 bispecific protein complexes.

In one embodiment the number of heterodimerically-tethered bispecific proteins in this multiplex is $n^2$ where n is 1, 2, 3, 4, 5, 6, 7, 8, 9, 10, 11, 12, 13, 14, 15 or more.

In one embodiment the method is performed in a grid or an an array, for example a microtitre plate, wherein each well of the microplate may contain a different bispecific protein complex.

The bispecific protein complexes may be tethered to a solid substrate surface, for example attached to a bead, or they may be suspended in a liquid (e.g. a solution or media) form, for example within a well or within a droplet.

In one embodiment every 'A' in the multiplex is a different protein, preferably an antibody or binding fragment thereof that binds to a target antigen and every 'B' is a different protein preferably an antibody or binding fragment thereof that binds to a target antigen.

In one embodiment the multiplex is provided in a grid as discussed below, for example an 8×8, 16×16 or 16×20, which equates to 64, 256 or 320 samples respectively.

"Grid" as employed herein refers to a two dimensional plot or array where one variable, such a protein A (in A-X) is varied along one axis, such as the X-axis (horizontal axis) and another variable such as protein B (in B-Y) is varied along the other axis, such as the Y axis (vertical axis). This arrangement assists in systematically evaluating the various combinations (permutations) of the variables.

In one embodiment the array is provided on 96 well plates and the samples analysed may be multiples thereof i.e. 96, 192, 384 etc.

Advantageously, a grid arrangement is particularly advantageous for efficiently screening the biological function of bispecific protein complexes according to the present disclosure.

Figure 3:
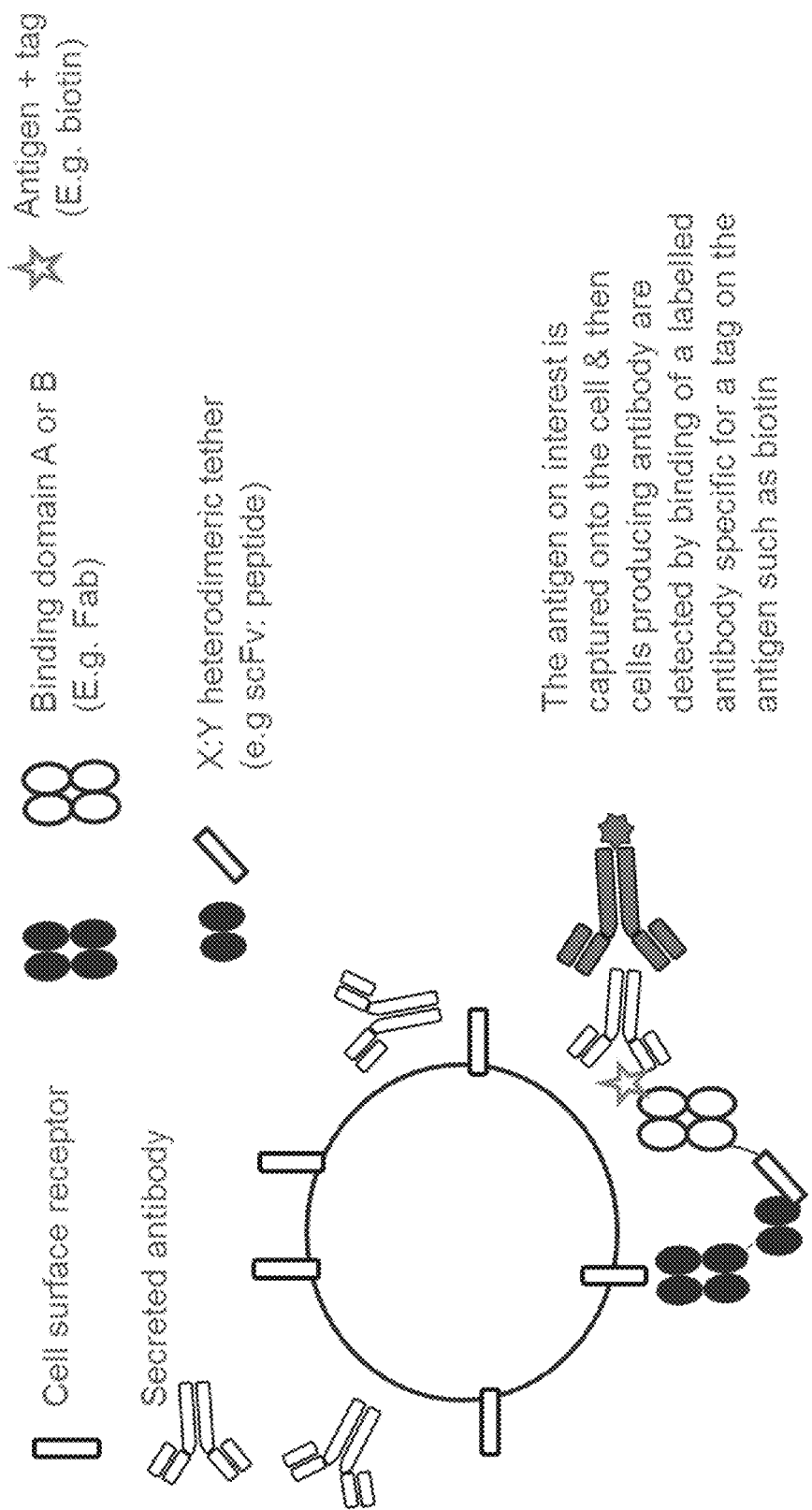
FIG. 3 shows a Fab-scFv (A-X respectively labelled Fab-X in the figure) in complex with a peptide-Fab (Y-B respectively labelled Fab-Y in the figure) wherein Fab A is bound to (specific to) a cell surface receptor and Fab B binds to (is specific to) an antigen which is also bound by a immunoglobulin secreted from the cell, and the detection system is a labelled antibody. Fab B and the secreted immunoglobulin bind different epitopes on the antigen.

FIG. 3 shows an example of such a grid, whereby 4 first fusion proteins can be readily combined with 4 second fusion proteins to produce 16 bispecific protein complexes.

Other variations of a screening grid will be apparent to the skilled addressee, for example the first protein (A) in the first fusion protein (A-X) may be kept constant whilst the second protein (B) in the second fusion protein (B-X) is varied. This may be useful for quickly screening a large number of different second proteins for synergistic function with the pre-selected first protein.

In another embodiment, protein A is varied along one axis by changing the antibody variable regions of protein A such that each antibody variant is specific for the same antigen but has a different combination of variable regions. Protein B may either be kept constant or may also be varied in the same fashion or varied such that the antigen specificity changes (across or down the grid) for the B proteins.

In one embodiment, a "common" first fusion protein (A-X) according to the present disclosure may be present within each well. A range of different second fusion proteins (B-Y) according to the present disclosure may then be dispensed into each well. Subsequently, the specific binding interaction of the two binding partners (X and Y) physically brings the two fusion proteins together to form the bispecific protein complexes. This results in an array comprising bispecific protein complexes which all bind to a first target cell antigen (bound by A) but are also capable of binding to a second soluble target antigen (bound by B) which may be different for each bispecific protein complex.

In one embodiment the A-X fusion proteins comprise different variable regions to the same cell surface target antigen to allow optimisation of the variable regions and/or epitopes of the given target antigen bound by B when combined with the variable regions in A-X.

In one embodiment the B-Y fusion proteins comprise different variable regions to the same soluble target antigen to allow optimisation of the variable regions and/or epitopes of the given target antigen bound by B when combined with the variable regions in A-X.

The skilled person is also aware of different variations of the above, such that the desired specificities of the bispecific protein complexes at each position in the multiplex can be readily controlled. This allows for the efficient screening of different combinations of bispecific protein complexes when such multiplexes are used in binding and functional assays. In one embodiment factorial design is employed to define the variables employed in the grid.

In one embodiment the method of the present disclosure is conducive to high-throughput analysis.

In one embodiment, multiple bispecific protein complexes are tested in parallel or essentially simultaneously.

Cells identified by methods of the present disclosure can be sorted employing techniques such as FACS, magnetic beads, microfluidics or another method available in the art.

In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number 05412 and 05627 respectively), HA-tag which correspond to amino acids 98 to 106 of human influenza hemagglutinin, polyhistidine (His), c-myc and FLAG. Other peptides are also contemplated as suitable for use in the present disclosure and particularly suitable peptides are affinity tags for protein purification because such peptides have a tendency to bind with high affinity to their respective binding partners.

In one embodiment the peptide is not E5B9.

The term "peptide" as used herein refers to a short polymer of amino acids linked by peptide bonds, wherein the peptide contains in the range of 2 to 100 amino acids, for example 5 to 99, such as 6 to 98, 7 to 97, 8 to 96 or 5 to 25. In one embodiment a peptide employed in the present disclosure is an amino acid sequence of 50 amino acid residues or less, for example 40, 30, 20, 10 or less.

In one embodiment, the protein is an antibody or an antibody fragment.

The term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site herein), located in the variable region of the immunoglobulin molecule.

As used herein "antibody molecule" includes antibodies and binding fragments thereof.

"Antibody fragments" or "antigen-binding fragment" of an antibody as employed herein refer to fragments of an antibody, naturally occurring or man-made, including but not limited to Fab, modified Fab, Fab', modified Fab', F(ab')2, Fv, single domain antibodies (sdAb), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171. Multi-valent antibodies may comprise multiple specificities e.g. bispecific or may be monospecific (see for example WO92/22853, WO05/113605, WO2009/040562 and WO2010/035012).

An "antigen-binding fragment" as employed herein refers to a fragment capable of binding a target peptide or antigen with sufficient affinity to characterise the fragment as specific for the peptide or antigen.

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain. In one example the heavy chain sequences of the Fab fragment "terminates" at the interchain cysteine of CH1. In one embodiment the Fab fragment employed in a fusion protein of the present disclosure, such as A-X and/or B-Y is monovalent.

A Fab' fragment as employed herein refers to a Fab fragment further comprising all or part of a hinge region. In one embodiment the Fab' fragment employed in a fusion protein of the present disclosure, such as A-X and/or B-Y is monovalent.

The term "single-chain Fv" or abbreviated as "scFv", as used herein refers to an antibody fragment that comprises VH and VL antibody domains linked (for example by a peptide linker) to form a single polypeptide chain. The constant regions of the heavy and light chain are omitted in this format. Single-chain Fv as employed herein includes disulfide stabilised versions thereof wherein in addition to the peptide linker a disulfide bond is present between the variable regions.

Disulfide stabilised scFv may eliminate the propensity of some variable regions to dynamically breath, which relates to variable regions separating and coming together again.

The term "single domain antibody" as used herein refers to an antibody fragment consisting of a single monomeric variable antibody domain. Examples of single domain antibodies include VH or VL or sdAb.

The term "sdAb" or "single domain antibodie(s)" as used herein refers to molecules comprising a single antigen-binding domain. They may be artificially created or naturally occurring and include, but are not limited to, VH only, VL only, camelid VHHs, human domain antibodies, shark derived antibodies such as IgNARs.

In one embodiment the antibody binding fragment and/or the bispecific antibody complex does not comprise an Fc region. "Does not comprise an Fc region" as employed herein refers to the lower constant domains, such as CH2, CH3 and CH4 which are absent. However, constant domains such as CH1, CKappa/CLambda may be present.

In one embodiment, the antibody heavy chain comprises a CH1 domain and the antibody light chain comprises a CL domain, either kappa or lambda.

In one embodiment, the antibody heavy chain comprises a CH1 domain, a CH2 domain and a $CH_3$ domain and the antibody light chain comprises a CL domain, either kappa or lambda.

In one embodiment, the first protein, A, and/or second protein, B, of the bispecific protein complex is an antibody or antibody fragment. Such a bispecific protein complex may be referred to as a bispecific antibody complex.

Bispecific protein complex comprise a protein capable of binding the cell surface and protein capable of binding a soluble molecule secrete from the cell, tethered together by X and Y.

In one embodiment the bispecific protein complex is an bispecific antibody complex.

In one embodiment "Bispecific antibody complex" as employed herein refers to a bispecific protein complex comprising at least two antibody binding sites wherein the component antibodies, fragments or both are complexed together by a heterodimeric-tether.

Complexed as employed herein generally refers to where A-X and B-Y are tethered together by the interaction X:Y.

Uncomplexed as employed herein refers to where A-X and B-Y are separate molecules. In one embodiment, B and the labelled antibody for detection (for example antibodies, fragments or a combination of an antibody and a fragment) target the same antigen, for example binding to two different epitopes on the same target antigen In another embodiment, B and the labelled antibody for detection (for example antibodies, fragments or a combination of an antibody and a fragment) may have different antigen specificities, for example binding to two different target antigens.

In one embodiment each antibody or fragment employed in the bispecific antibody complex of the disclosure comprises one binding site i.e. each binding site is monovalent for each target antigen.

Antigen as employed herein as employed herein refers to a molecule which under appropriate conditions stimulates the body to raise antibodies to it. Antigens are usually peptides, proteins, glycoproteins, polysaccharides, lipid and synthetic or naturally occurring chemical compounds or combinations thereof. As used herein, the term "antigen" preferably refers to a proteins, such as a glycoproteins or complexes of proteins with lipids, such as membrane lipids, and in particular to CD45 and immunoglobulins. The full length antibody or antibody fragment employed in the fusion proteins (A-X or B-Y) may be monospecific, monovalent, multivalent or bispecific.

Advantageously, the use of two bispecific antibody or antibody fragments allows the bispecific antibody complex of the present disclosure to potentially be specific for up to 4 different antigens (i.e. the complex may be tetraspecific). This allows avidity type effects to be investigated.

In one embodiment, the antibody or antibody fragment employed in the first fusion protein (A-X) is a monospecific antibody or antibody fragment, in particular a monovalent Fab, Fab', scFv, Fv, sdAb or similar.

In one embodiment, the antibody or antibody fragment employed in the second fusion protein (B-Y) is a monospecific antibody or antibody fragment, in particular a monovalent Fab, Fab', scFv or similar.

"Monospecific" as employed herein refers to the ability to bind only one target antigen.

"Monovalent" as employed herein refers to the antibody or antibody fragment having a single binding site and therefore only binding the target antigen only once.

In one embodiment, the antibody or antibody fragment employed in the first fusion protein (A-X) is multivalent, that is has two or more binding domains.

In one embodiment, the antibody or antibody fragment employed in the second fusion protein (B-Y) is multivalent, that is has two or more binding domains.

In one embodiment, the antibody or antibody fragment employed in the first fusion protein (A-X) is monovalent and the antibody or antibody fragment employed in the second fusion protein (B-X) is monovalent.

In one embodiment, the antibody or antibody fragment employed in the first fusion protein (A-X) is monovalent and the antibody or antibody fragment employed in the second fusion protein (B-Y) is multivalent.

In one embodiment, the antibody or antibody fragment employed in the first fusion protein (A-X) is multivalent and the antibody or antibody fragment employed in the second fusion protein (B-Y) is monovalent.

In one embodiment, the antibody or antibody fragment employed in the first fusion protein (A-X) is multivalent and the antibody or antibody fragment employed in the second fusion protein (B-Y) is multivalent.

In one embodiment A-X or B-Y is not a fusion protein comprising two scFvs one specific to the antigen CD33 and one specific to the antigen CD3 or alternatively a bispecific complex format specific to these two antigens.

In one embodiment the A-X or B-Y is not a fusion protein comprising a scFv (or alternatively another antibody format) specific to CD3 linked to a peptide E5B9.

A "binding domain or site" as employed herein is the part of the antibody that contacts the antigen/epitope and participates in a binding interaction therewith. In one embodiment the binding domain contains at least one variable domain or a derivative thereof, for example a pair of variable domains or derivatives thereof, such as a cognate pair of variable domains or a derivative thereof.

In one embodiment the binding domain comprises 3 CDRs, in particular where the binding domain is a domain antibody such as a VH, VL or sdAb. In one embodiment the binding domain comprises two variable domains and 6 CDRs and a framework and together these elements contribute to the specificity of the binding interaction of the antibody or binding fragment with the antigen/epitope.

A "cognate pair" as employed herein refers to a heavy and light chain pair isolated from a host as a pre-formed couple. This definition does not include variable domains isolated from a library, wherein the original pairings from a host is not retained. Cognate pairs may be advantageous because they are often affinity matured in the host and therefore may have high affinity for the antigen to which they are specific.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, GPI anchors, or solvent exposed lysines. These modifications can be achieved by replacing the relevant amino acid residues with a conservative amino acid substitution.

In one embodiment, the bispecific antibody complexes of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment, the first antibody or antibody fragment (A) is specific to a first antigen and the second antibody or antibody fragment (B) is specific to a second antigen, and generally the first and second antigens are different. This presents the possibility of the antibody complex binding to two different antigens, each located on a different entity, thereby bringing the two entities into close physical proximity with each other.

In one embodiment, the first antibody/fragment (A), second antibody/fragment (B) or both the first and second antibody/fragment of the bispecific antibody complex of the present disclosure may be a Fab.

In one embodiment, the first antibody/fragment (A), second antibody/fragment (B) or both the first and second antibody/fragment of the bispecific antibody complex of the present disclosure may be a Fab'.

In one embodiment, the first antibody/fragment (A), second antibody/fragment (B) or both the first and second antibody/fragment of the bispecific antibody complex of the present disclosure may be a scFv.

In one embodiment, the first (A) or second (B) antibody/fragment or both the first and second antibody/fragment of the bispecific antibody complex of the present disclosure is/are a sdAb.

For convenience bispecific protein complexes of the present disclosure are referred to herein as A-X:Y-B. A and B and X and Y are nominal labels referred to for assisting the explanation of the present technology.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair.

In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

In one embodiment, the first binding partner (X) is selected from the group comprising: a full length antibody, a Fab, a Fab', Fv, dsFv, a scFv and a sdAb, wherein examples of a sdAb include VH or VL or sdAb.

When X is an antibody or binding fragment thereof then Y is a protein or peptide, in particular a peptide.

In one embodiment, the second partner (Y) is selected from the group comprising: a full length antibody, a Fab, a Fab', Fv, dsFv, a scFv and a sdAb, wherein examples of a sdAb include VH or VL or sdAb.

When Y is an antibody or binding fragment thereof then X is a protein or peptide, in particular a peptide.

In one embodiment, where A is an antibody or fragment thereof the first binding partner (X) is attached to the C-terminal of the heavy or light chain of the first antibody or antibody fragment, for example, the first binding partner (X) is attached to the C-terminal of the heavy chain of the first antibody or antibody fragment (A).

In another embodiment, where B is an antibody or fragment thereof the second binding partner (Y) is attached to the C-terminal of the heavy or light chain of the second antibody or antibody fragment, for example the second binding partner (Y) is attached to the C-terminal of the heavy chain of the second antibody or antibody fragment (B).

In one embodiment X is attached to the C-terminal of the heavy chain of the antibody or fragment (protein A) and Y is attached to the C-terminal of the heavy chain of the antibody or fragment (protein B).

In one embodiment X is attached via a linker (such as ASGGGG SEQ ID NO: 71 or ASGGGGSG SEQ ID NO: 72 or ASGGG SEQ ID NO: 73 or AAASGGG SEQ ID NO: 74) or any other suitable linker known in the art or described herein below, to the C-terminal of the heavy chain of the antibody or fragment (protein A) and Y is attached via a linker (such as ASGGGG SEQ ID NO: 71 or ASGGGGSG SEQ ID NO: 72 or ASGGG SEQ ID NO: 73 or AAASGGG SEQ ID NO: 74) to the C-terminal of the heavy chain of the antibody or fragment (protein B).

Examples of a suitable binding pair (X or Y) may include GCN4 (SEQ ID NO: 1 or lacking the HIS tag, amino acids 1-38 of SEQ ID NO: 1) or a variant thereof (for example any of the sequences shown by SEQ ID NOs: 76-98) and 52SR4 (SEQ ID NO: 3 or lacking the HIS tag amino acids 1 to 243 of SEQ ID NO:3) or a variant thereof, which is a scFv specific for GCN4.

In a one embodiment, the first binding partner (nominally X) is GCN4 (for example as shown in SEQ ID NO: 1) or a fragment or variant thereof (for example without the His tag or any of the sequences shown by SEQ ID NOs: 76-98) and the second binding partner (nominally Y) is a scFv or sdAb specific for GCN4 (for example as shown in SEQ ID NO: 3, 99 or 100) or a variant thereof.

In one embodiment, the first binding partner (nominally X) is a sFv or sdAb specific for GCN4 (for example as shown in SEQ ID NO: 3, 99 or 100) or a variant thereof and the second binding partner (nominally Y) is GCN4 (for example as shown in SEQ ID NO: 1) or a fragment or variant thereof (for example any of the sequences shown by SEQ ID NOs: 76-98).

GCN4 variants include an amino acid sequence with at least 80%, 85%, 90%, 91%, 92%, 93%, 94% 95%, 96%, 97% or 98%, or 99% identity to SEQ ID NO: 1. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO: 2, or a sequence encoded by a nucleotide sequence which hybridises to SEQ ID NO: 2 under stringent conditions.

A suitable scFv specific to GCN4 is 52SR4 (SEQ ID NO: 3) or a variant thereof (SEQ ID NO: 99 or 100). Variants of 52SR4 include an amino acid sequence with at least 80%, or 85%, or 90%, or 95%, or 98%, or 99% identity to SEQ ID NO: 3. 52SR4 variants also include an amino acid sequence having at least at least 80%, or 85%, or 90%, or 95%, or 98%, or 99% to a sequence encoded by a nucleotide sequence SEQ ID NO: 4, or a sequence encoded by a nucleotide sequence which hybridises to SEQ ID NO: 4 under stringent conditions.

The present inventors have found that the single chain antibody 52SR4 and peptide GCN4, are a binding pair suitable for use in the bispecific protein complexes of the present disclosure.

Alternatively, any suitable antibody/fragment and antigen (such as a peptide) may be employed as X and Y. Preferably such an X and Y pair result in greater than 75% heterodimer when A-X and Y-B are combined in a 1:1 molar ratio.

In one embodiment, the first binding partner (X) and the second binding partner (Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the first or second binding partner (X or Y) is a protein or peptide.

The linker may be any structural component useful and capable to connect the fusion proteins. In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker; alternatives may be a lipid or a sugar linker or a chemical compound.

The term "peptide linker" as used herein refers to a peptide with an amino acid sequence. A range of suitable peptide linkers will be known to the person of skill in the art.

In one embodiment, the binding partners of the bispecific protein complexes are joined to their respective proteins via peptide linkers.

In one embodiment the fusion proteins are a translational fusion, that is a fusion protein expressed in a host cell comprising a genetic construct from which the fusion protein is expressed.

In one embodiment the fusion protein is prepared by fusing the heavy chain of A to X and/or the heavy chain of B to Y optionally via a peptide linker.

In one embodiment, the peptide linker is 50 amino acids in length or less, for example 20 amino acids or less.

Generally it will be more efficient to express the fusion protein recombinantly and therefore a direct peptide bond or a peptide linker that can be expressed by a host cell may be advantageous.

In one embodiment, the linker is selected from a sequence as shown in SEQ ID NOs: 5 to 72 (Tables 2, 3 and 4) or a sequence corresponding to PPP.

TABLE 2

| SEQ ID NO: | SEQUENCE |
|---|---|
| 5 | DKTHTCAA |
| 6 | DKTHTCPPCPA |
| 7 | DKTHTCPPCPATCPPCPA |
| 8 | DKTHTCPPCPATCPPCPATCPPCPA |
| 9 | DKTHTCPPCPAGKPTLYNSLVMSDTAGTCY |
| 10 | DKTHTCPPCPAGKPTHVNVSVVMAEVDGTCY |
| 11 | DKTHTCCVECPPCPA |
| 12 | DKTHTCPRCPEPKSCDTPPPCPRCPA |
| 13 | DKTHTCPSCPA |

TABLE 3

| SEQ ID NO: | SEQUENCE |
|---|---|
| 14 | SGGGGSE |
| 15 | DKTHTS |
| 16 | (S)GGGGS |
| 17 | (S)GGGGSGGGGS |
| 18 | (S)GGGGSGGGGSGGGGS |
| 19 | (S)GGGGSGGGGSGGGGSGGGGS |
| 20 | (S)GGGGSGGGGSGGGGSGGGGSGGGGS |
| 21 | AAAGSG-GASAS |

TABLE 3-continued

| SEQ ID NO: | SEQUENCE |
|---|---|
| 22 | AAAGSG-XGGGS-GASAS |
| 23 | AAAGSG-XGGGSXGGGS-GASAS |
| 24 | AAAGSG-XGGGSXGGGSXGGGS-GASAS |
| 25 | AAAGSG-XGGGSXGGGSXGGGSXGGGS-GASAS |
| 26 | AAAGSG-XS-GASAS |
| 27 | PGGNRGTTTTRRPATTTGSSPGPTQSHY |
| 28 | ATTTGSSPGPT |
| 29 | ATTTGS |
| 30 | AAAAAAAAAAAA |
| 31 | EPSGPISTINSPPSKESHKSP |
| 32 | GTVAAPSVFIFPPSD |
| 33 | GGGGIAPSMVGGGGS |
| 34 | GGGGKVEGAGGGGGS |
| 35 | GGGGSMKSHDGGGGS |
| 36 | GGGGNLITIVGGGGS |
| 37 | GGGGVVPSLPGGGGS |
| 38 | GGEKSIPGGGGS |
| 39 | RPLSYRPPFPFGFPSVRP |
| 40 | YPRSIYIRRRHPSPSLTT |
| 41 | TPSHLSHILPSFGLPTFN |
| 42 | RPVSPFTFPRLSNSWLPA |
| 43 | SPAAHFPRSIPRPGPIRT |
| 44 | APGPSAPSHRSLPSRAFG |
| 45 | PRNSIHFLHPLLVAPLGA |
| 46 | MPSLSGVLQVRYLSPPDL |
| 47 | SPQYPSPLTLTLPPHPSL |
| 48 | NPSLNPPSYLHRAPSRIS |
| 49 | LPWRTSLLPSLPLRRRP |
| 50 | PPLFAKGPVGLLSRSFPP |
| 51 | VPPAPVVSLRSAHARPPY |
| 52 | LRPTPPRVRSYTCCPTP- |
| 53 | PNVAHVLPLLTVPWDNLR |
| 54 | CNPLLPLCARSPAVRTFP |

(S) is optional in sequences 17 to 20. Another linker may be peptide sequence GS. Examples of rigid linkers include the peptide sequences GAPAPAAPAPA (SEQ ID NO: 69), PPPP (SEQ ID NO: 70) and PPP.

TABLE 4

| SEQ ID NO: | SEQUENCE |
|---|---|
| 55 | DLCLRDWGCLW |
| 56 | DICLPRWGCLW |
| 57 | MEDICLPRWGCLWGD |
| 58 | QRLMEDICLPRWGCLWEDDE |
| 59 | QGLIGDICLPRWGCLWGRSV |
| 60 | QGLIGDICLPRWGCLWGRSVK |
| 61 | EDICLPRWGCLWEDD |
| 62 | RLMEDICLPRWGCLWEDD |
| 63 | MEDICLPRWGCLWEDD |
| 64 | MEDICLPRWGCLWED |
| 65 | RLMEDICLARWGCLWEDD |
| 66 | EVRSFCTRWPAEKSCKPLRG |
| 67 | RAPESFVCYWETICFERSEQ |
| 68 | EMCYFPGICWM |

In one aspect, there is provided a method of producing a bispecific protein complex of the present disclosure, comprising the steps of:
 (a) producing a first fusion protein (A-X), comprising a first protein (A), attached to a first binding partner (X) of a binding pair;
 (b) producing a second fusion protein (B-Y), comprising a second protein (B), attached to a second binding partner (Y) of a binding pair; and
 (c) mixing the first (A-X) and second fusion proteins (B-Y) prepared in step a) and b) together.

Typically the mixing of A-X and B-Y in step (c) is in a 1:1 molar ratio.

In one embodiment each fusion proteins employed in the complexes of the present disclosure are produced by expression in a host cell or host cells in an expression experiment.

In one aspect, there is provided a method of preparing a bispecific protein complex of the present disclosure, comprising the steps of:
 (a) expressing a first fusion protein (A-X), comprising a first protein (A), attached to a first binding partner (X) of a binding pair;
 (b) expressing a second fusion protein (B-Y), comprising a second protein (B), attached to a second binding partner (Y) of a binding pair;
wherein fusion protein A-X and B-Y are expressed from the same host cell or distinct host cells.

Distinct host cells as employed herein refers to individual cells, including cells of the same type (even same clonal type).

In one embodiment the expression is transient expression. The use of transient expression is highly advantageous when combined with the ability to generate bispecific complexes without recourse to purification. This results in a rapid method to generate bispecific protein complexes as transient transfection is much simpler and less resource intensive than stable transfection.

In one embodiment the expression is stable expression i.e. wherein the DNA encoding the fusion protein in question is stably integrated into the host cell genome.

In one embodiment a polynucleotide encoding A-X and a polynucleotide encoding B-Y on the same or different polynucleotide sequences are transfected into a cell as part of a functional assay, wherein the proteins are expressed in the cell and/or released therefrom. In particular the polynucleotides are transiently transfected on the same of different plasmids.

The mixing of A-X and B-Y is generally effected in conditions where the X and Y can interact. In one embodiment, the fusion proteins are incubated in cell culture media under cell culturing conditions, for example the fusion proteins are incubated for 90 minutes in a 37° C./5% $CO_2$ environment.

In one embodiment the fusion proteins of the present disclosure are mixed in an aqueous environment, for example one fusion protein may be bound to a solid surface such as a bead or a plate and the other fusion protein can be introduced thereto in an aqueous solution/suspension. The solid phase allows excess components and reagents to be washed away readily. In one embodiment neither fusion is attached a solid phase and are simply mixed in a liquid/solution/medium. Thus in one embodiment A-X and B-Y are mixed as free proteins in an aqueous media.

Advantageously, the method of the present disclosure can be employed to prepare complexes formed between heterogenous pairs (i.e. between the first fusion protein [A-X] and second fusion protein [B-Y]) wherein interactions between homogenous pairs (i.e. between two first fusion proteins [A-X] or two second fusion proteins [B-Y]) are minimised. Thus the present method allows large numbers of bispecific protein complexes to be prepared, with minimal or no contamination with homodimeric complexes. An advantage of the constructs and method of the present disclosure is that the ratio of A-X to B-Y is controlled by the properties of the A-X and B-Y and in particular a molar ratio of 1:1 can be achieved. This element of control is a significant improvement over the certain prior art methods.

If present constant region domains of a bispecific antibody complex or antibody molecule of the present disclosure, if present, may be selected having regard to the proposed function of the complex or antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

The present disclosure also provides a composition comprising one or more bispecific protein complexes as described above, wherein the composition predominantly comprises heterodimeric bispecific complexes according to the present disclosure, for example with minimal or no contamination with homodimeric complexes.

In one embodiment, at least 60%, at least 65%, at least 70%, at least 75%, at least 80%, at least 90%, or at least 95% of the fusion proteins in the composition are in a bispecific protein complex form.

In one embodiment, at least 60% of the fusion proteins in the composition are in a bispecific protein complex form.

In one embodiment the complexes formed require no further purification steps and thus the compositions comprise unpurified bispecific complexes.

In one embodiment the complexes formed require one purification step, for example column chromatography.

In one embodiment the method further comprises at least one purification step, for example after expression of a fusion protein according to the present disclosure and before mixing the fusion proteins.

In one aspect the present disclosure relates to a fusion protein, a heterodimerically-tethered bispecific protein complex, a composition comprising a fusion protein or said bispecific protein complex, a multiple, array, library as defined herein.

In one embodiment, the bispecific protein complex is in solution or suspension.

In one embodiment, the bispecific protein complexes are fixed on a solid substrate surface.

In one embodiment, the multiplex is in the form of an array, for example in a microplate, such as a 96 or 384 well plate. Such arrays can be readily implemented in screening assays to identify bispecific protein complexes with desired functionality.

In another embodiment, the bispecific protein complexes are conjugated to beads.

A fusion protein as defined above is a component of the bispecific protein complex according to the present disclosure. In one aspect, the present disclosure relates to a fusion protein described herein.

In a further aspect, there is provided a library, comprising two or more fusion proteins as defined above.

The term "library" as used herein refers to two or more bispecific antibody complexes of the present disclosure or multiple fusion proteins of the present disclosure that can be combined to form at least two different bispecific antibody complexes according to the present disclosure. As described throughout the specification, the term "library" is used in its broadest sense and may also encompass sub-libraries.

Advantageously, the library may comprise a range of different fusion proteins which have either the first binding partner (X) or second binding partner (Y) of a particular binding pair attached thereto. In one embodiment part of the library comprises proteins/antibodies/fragments each connected to a binding partner X and the remainder of the library comprises the same proteins/antibodies/fragments each connected to a binding partner Y. This thus allows any two fusion proteins to be readily combined to form a bispecific protein complex of the present disclosure, as long as one fusion protein has the first binding partner of a binding pair attached and the other fusion protein has the second binding partner of the binding pair attached.

In one embodiment bispecific protein complexes of the present invention are suitable for therapeutic applications and may provide novel therapies for treating diseases. Thus in a further aspect, there is provided a bispecific protein complex as described above for use in therapy.

In one embodiment there is provided a fusion protein obtained or obtainable for a method of the present disclosure.

In one embodiment there is provided an bispecific antibody complex obtained or obtainable from a method of the present disclosure In one embodiment there is provided a bispecific or multispecific antibody molecule comprising variable regions combinations identified by a method according to the present disclosure.

In one embodiment there is provided a composition, such as a pharmaceutical composition comprising a fusion protein, a bispecific antibody complex or a bispecific/multispecific antibody molecule obtained from a method of the present disclosure.

Various different components can be included in the composition, including pharmaceutically acceptable carriers, excipients and/or diluents. The composition may, optionally, comprise further molecules capable of altering the characteristics of the population of antibodies of the invention thereby, for example, reducing, stabilizing, delaying, modulating and/or activating the function of the antibodies. The composition may be in solid, or liquid form and may inter alia, be in the form of a powder, a tablet, a solution or an aerosol.

The present disclosure also provides a pharmaceutical or diagnostic composition comprising a bispecific protein complex of the present invention in combination with one or more of a pharmaceutically acceptable excipient, diluent or carrier. Accordingly, provided is the use of a bispecific protein complex of the invention for use in the treatment and for the manufacture of a medicament for the treatment of a pathological condition or disorder.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

The present disclosure also provides a pharmaceutical or diagnostic composition comprising a bispecific protein complex of the present invention in combination with one or more of a pharmaceutically acceptable excipient, diluent or carrier. Accordingly, provided is the use of a bispecific protein complex of the invention for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule or bispecific antibody complex of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragés, capsules, liquids, gels, syrups, slurries and suspensions, for ingestion by the patient.

The bispecific protein complexes of the invention can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The bispecific antibody complex (or bispecific/multispecific antibody molecule of the present disclosure) may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment, the antibody, fragment or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternatively a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the bispecific antibody complex of the invention (or a bispecific/multispecific antibody molecule of the present disclosure).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

Where the product is for injection or infusion, it may take the form of a suspension, solution or emulsion in an oily or aqueous vehicle and it may contain formulatory agents, such as suspending, preservative, stabilising and/or dispersing agents. Alternatively, the bispecific protein complex (or bispecific/multispecific antibody molecule of the present disclosure) may be in dry form, for reconstitution before use with an appropriate sterile liquid. If the composition is to be administered by a route using the gastrointestinal tract, the composition will need to contain agents which protect the antibody from degradation but which release the bispecific protein complex once it has been absorbed from the gastrointestinal tract.

A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

Antigens include cell surface receptors such as T cell or B cell signalling receptors, co-stimulatory molecules, checkpoint inhibitors, natural killer cell receptors, Immunolglobulin receptors, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors or soluble molecules such as cytokines, chemokines, leukotrienes, growth factors, hormones or enzymes or ion channels, epitopes, fragments and post translationally modified forms thereof.

In one embodiment, the bispecific protein complex comprises one or two cell surface receptor specificities.

In one embodiment, the bispecific protein complex comprises one or two cytokine or chemokine specificities.

Antibodies or fragments to a pair of targets identified by the method according to the present disclosure may be incorporated into any format suitable for use as a laboratory reagent, an assay reagent or a therapeutic.

Thus in one aspect the disclosure extends to use of antibodies fragments or combinations thereof as pairs in any format, examples of which are given above.

The disclosure also extends to compositions, such as pharmaceutical compositions comprising said novel formats with the particular antigen specificity.

In a further aspect the disclosure includes use of the formats and the compositions in treatment.

In one embodiment, the bispecific protein complex of the present disclosure may be used to functionally alter the activity of the antigen or antigens of interest. For example, the bispecific protein complex may neutralize, antagonize or agonise the activity of said antigen or antigens, directly or indirectly.

The present disclosure also extends to a kit, for example comprising A-X and B-Y in a complexed or uncomplexed form, for use in the method of the present disclosure.

In another embodiment, the kit further comprises instructions for use.

In yet another embodiment, the kit further comprises one or more reagents for performing one or more functional assays.

In one embodiment, fusion proteins, bispecific proteins complexes, multiplexes, grids, libraries, compositions etc as described herein are for use as a laboratory reagent.

In a further aspect, there is provided a nucleotide sequence, for example a DNA sequence encoding a fusion protein and/or a bispecific protein complex as defined above.

In one embodiment, there is provided a nucleotide sequence, for example a DNA sequence encoding a bispecific protein complex according to the present disclosure.

In one embodiment there is provided a nucleotide sequence, for example a DNA sequence encoding a bispecific or multispecific antibody molecule according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F.

M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example E. coli, and other microbial systems may be used or eukaryotic, for example mammalian, host cell expression systems may also be used. Suitable mammalian host cells include CHO, myeloma or hybridoma cells.

The present disclosure also provides a process for the production of a fusion protein according to the present disclosure comprising culturing a host cell containing a vector of the present disclosure under conditions suitable for leading to expression of protein from DNA encoding the molecule of the present disclosure, and isolating the molecule.

The bispecific protein complexes of the present disclosure may be used in diagnosis/detection kits, wherein bispecific protein complexes with particular combinations of antigen specificities are used. For example, the kits may comprise bispecific antibody complexes that are specific for two antigens, both of which are present on the same cell type, and wherein a positive diagnosis can only be made if both antigens are successfully detected. By using the bispecific antibody complexes of the present disclosure rather than two separate antibodies or antibody fragments in a non-complexed form, the specificity of the detection can be greatly enhanced.

In one embodiment, the bispecific antibody complexes are fixed on a solid surface. The solid surface may for example be a chip, or an ELISA plate.

Further provided is the use of a bispecific protein complex of the present disclosure for detecting in a sample the presence of a first and a second peptide, whereby the bispecific complexes are used as detection agents.

The bispecific antibody complexes of the present disclosure may for example be conjugated to a fluorescent marker which facilitates the detection of bound antibody-antigen complexes. Such bispecific antibody complexes can be used for immunofluorescence microscopy. Alternatively, the bispecific antibody complexes may also be used for western blotting or ELISA.

In one embodiment, there is provided a process for purifying an antibody (in particular an antibody or fragment according to the invention).

In one embodiment, there is provided a process for purifying a fusion protein or bispecific protein complex according to the present disclosure comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements.

Positive embodiments employed herein may serve basis for the excluding certain aspects of the disclosure.

Disclosures in the context of the method relating to the bispecific complexes apply equally to the complexes per se and vice versa.

EXAMPLES

Figure 10:
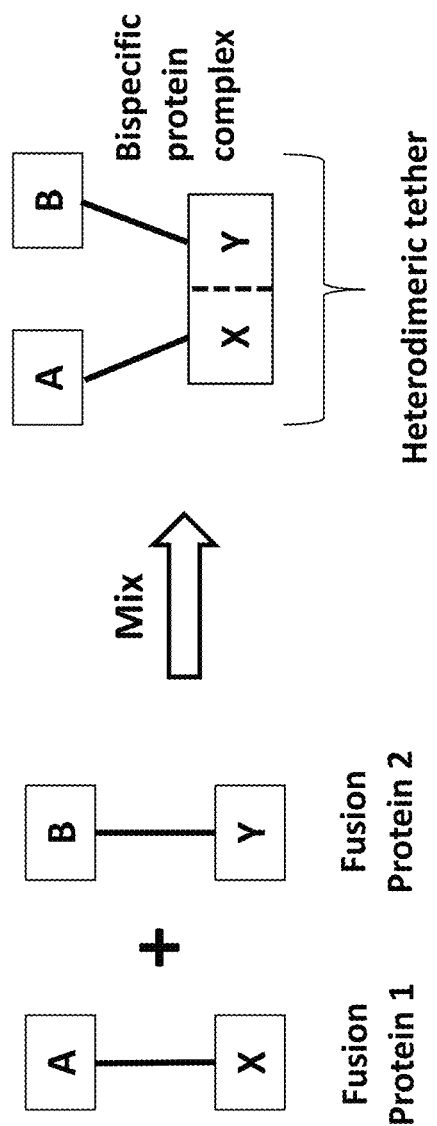
FIG. 10 is a schematic diagram showing the generic structure and assembly of a bispecific protein complex according to the present invention.
Figure 11:
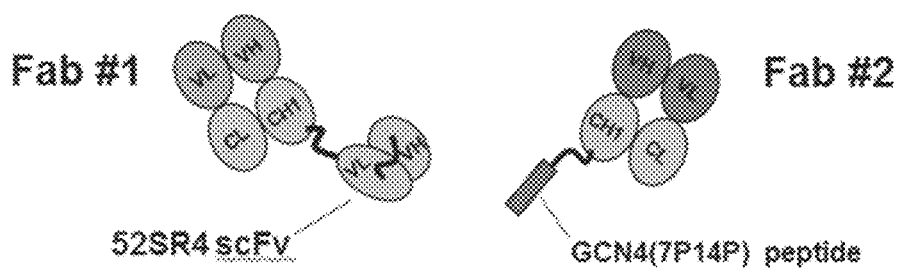
FIG. 11 is a cartoon showing the formation of a bispecific protein complex according to the present invention where A is a Fab which has fused at its C-terminal a X represented by 52SR4 scFv and B is a Fab which has fused at its C-terminal a Y represented by a GCN4 peptide (7P14P).
Figure 11:
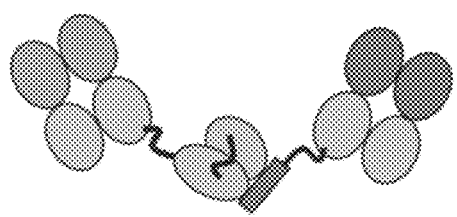

Example 1 Construction of a Bispecific Antibody Complex of the Present Disclosure FabB-GCN4(7P14P):52SR4-FabA FIGS. 10 and 11 show a representative bispecific antibody complex of the present disclosure. The bispecific antibody complex is composed of a first and second fusion protein. The first fusion protein (A-X) includes a Fab fragment (Fab A (also referred to as Fab #1) with specificity to soluble antigen IL-6, which is attached to X a scFv (clone 52SR4 SEQ ID NO: 3) via a peptide linker ASGGGG SEQ ID NO: 71 which is linked to the c-terminal of the $CH_1$ domain of the Fab fragment and the $V_L$ domain of the scFv. The scFv itself also contains a peptide linker located in between its $V_L$ and $V_H$ domains.

The second fusion protein (B-Y) includes a Fab fragment (Fab B [also referred to as Fab #2] with specificity to cell surface antigen CD3). However, in comparison to the first protein, the Fab fragment is attached to Y a peptide GCN4 (clone 7P14P SEQ ID NO: 1) via a peptide linker ASGGG SEQ ID NO: 73 which is linked to the $CH_1$ domain of the Fab fragment.

The scFv, X, is specific for and complementary to the binding partner Y, GCN4. As a result, when the two fusion proteins are brought into contact with each other, a non-covalent binding interaction between the scFv and GCN4 peptide occurs, thereby physically retaining the two fusion proteins in the form of a bispecific antibody complex.

The single chain antibody (scFv) 52SR4 was derived by constructing and panning a ribosome display VL-linker-VH scFv library from the spleens of mice immunized with GCN4(7P14P) (Hanes J, Jermutus L, Weber-Bornhauser S, Bosshard H R, Plückthun A. (1998) Proc. Natl. Acad. Sci. U.S.A. 95, 14130-14135). A further 2004 publication describes the affinity maturation of 52SR4 to a reported 5 pM again using ribosome display of randomised libraries (Zhand C, Spinelli S, Luginbuhl B, Amstutz P, Cambillau C, Pluckthun A. (2004) J. Biol. Chem. 279, 18870-18877).

The GCN4 peptide was derived from the yeast transcription factor GCN4 by inclusion of Proline residues at positions 7 and 14, hence GCN4(7P14P) remains in a monomeric state on scFv binding as described in a 1999 publication by Berger et al (Berger C, Weber-Bornhauser S, Eggenberger Y, Hanes J, Pluckthun A, Bosshard H. R. (1999) F.E.B.S. Letters 450, 149-153).

The nucleotide sequences encoding the GCN4 peptide and the 52SR4 scFv were cloned into two separate vectors downstream of in-house heavy chain Fab expression vectors which contain CH$_1$ and which are already designed to receive antibody VH-regions.

VH-regions from an anti-IL-6 antibody and an anti-CD3 antibody were then cloned separately into these two heavy chain vectors.

The nucleotide sequences encoding the GCN4 peptide and the 52SR4 scFv were separately cloned into a first and second vector respectively downstream of in-house light chain Fab expression vectors which contain CK and which are designed to receive antibody VL-regions.

VL-regions from an anti-IL-6 antibody and an anti-CD3 antibody were cloned separately in frame with CK in an in-house light chain expression vector for co-expression with the appropriate heavy chain vector to express the Fab-scFv and Fab-peptide proteins.

The vectors were then sequenced to confirm that the cloning has been successful and that the cells subsequently separately expressed Fab-scFv and Fab-peptide proteins with the V-regions from the anti-IL-6 antibody and the anti-CD3 antibody respectively.

Figure 12:
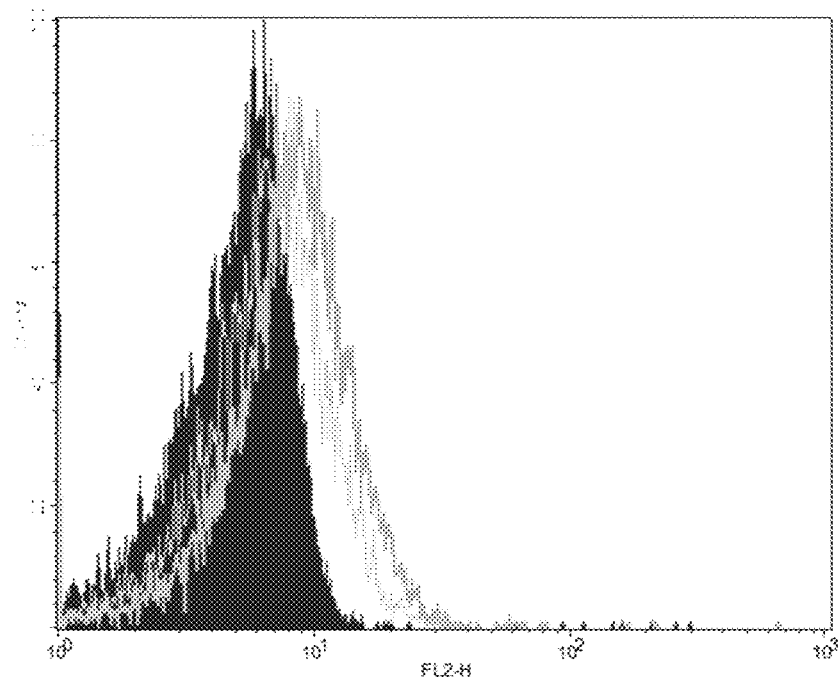
FIG. 12 Flow cytometry detection of antibody complex binding

Example 2—Flow Cytometry Demonstration of scFv:Peptide Interaction Forming a Non-Covalent Bispecific Antibody that can Co-Engage a Cell Surface and a Soluble Antigen Simultaneously FIG. 12 shows the results of a flow cytometry experiment which demonstrates the antigen specificities of two different bispecific antibody complexes formed using the scFv:peptide binding interaction.

The first bispecific antibody complex was constructed using the following two fusion proteins:
1. Anti-CD3 Fab-scFv (52SR4); and
2. Anti-antigen IL-6 Fab-peptide (GCN4)

The second bispecific antibody complex was constructed using the following two fusion proteins:
1. Anti-CD3 Fab-peptide (GCN4); and
2. Anti-antigen IL-6 Fab-scFv (52SR4)

Therefore, the two bispecific antibody complexes had the same Fab fragments and same binding partners (i.e. 52SR4 and GCN4). The difference between the two bispecific antibody complexes was in which Fab fragment is attached to which binding partner.

The control mixture which did not form a complex was made from the following fusion proteins:
1. Anti-CD3 Fab:GCN4; and
2. Anti-IL-6 Fab:GCN4

To demonstrate the ability of the bispecific antibody complexes to bind to CD3, the complexes were incubated with Jurkat cells which express CD3. To demonstrate the ability of the bispecific antibody complexes to bind to IL-6, the complexes once bound to CD3 on Jurkat cells were subsequently contacted with biotinylated antigen IL-6. The biotinylated antigen IL-6 was then detected using fluorescently labelled streptavidin.

The Jurkat cells were then run through a Facscalibur flow cytometer machine, wherein the fluorescently labelled Jurkat cells which can only be labelled when bound to a bispecific antibody complex, which is in turn bound to IL-6, thereby indicating that the bispecific antibody complex is capable of binding to both cell surface CD3 and soluble antigen IL-6 can be separated from Jurkat cells incubated with two fusion proteins capable of binding to CD3 and IL-6, both fused to peptide which cannot form a complex.

The FACS plot in FIG. 12 shows significant shifts for both the bispecific antibody complexes (thin and thick line over and above background filled), thus demonstrating that the bispecific antibody complexes can successfully bind to both target antigens and that the ability to bind to both target antigens is retained regardless of whether a given Fab fragment is connected to a scFv or peptide.

The subsequent capture of either peptide or scFv respectively C-terminally fused to the anti-IL-6 Fab allows further capture of biotinylated antigen IL-6 which is detected in a final layer with fluorescently labelled streptavidin. Accordingly, the results depicted in the FACS plot shows that the bispecific antibody complexes of the present disclosure are able to successfully bind a cell surface and a soluble antigen simultaneously.

Example 3—Biacore Demonstration of scFv:Peptide Interaction

Figure 13:
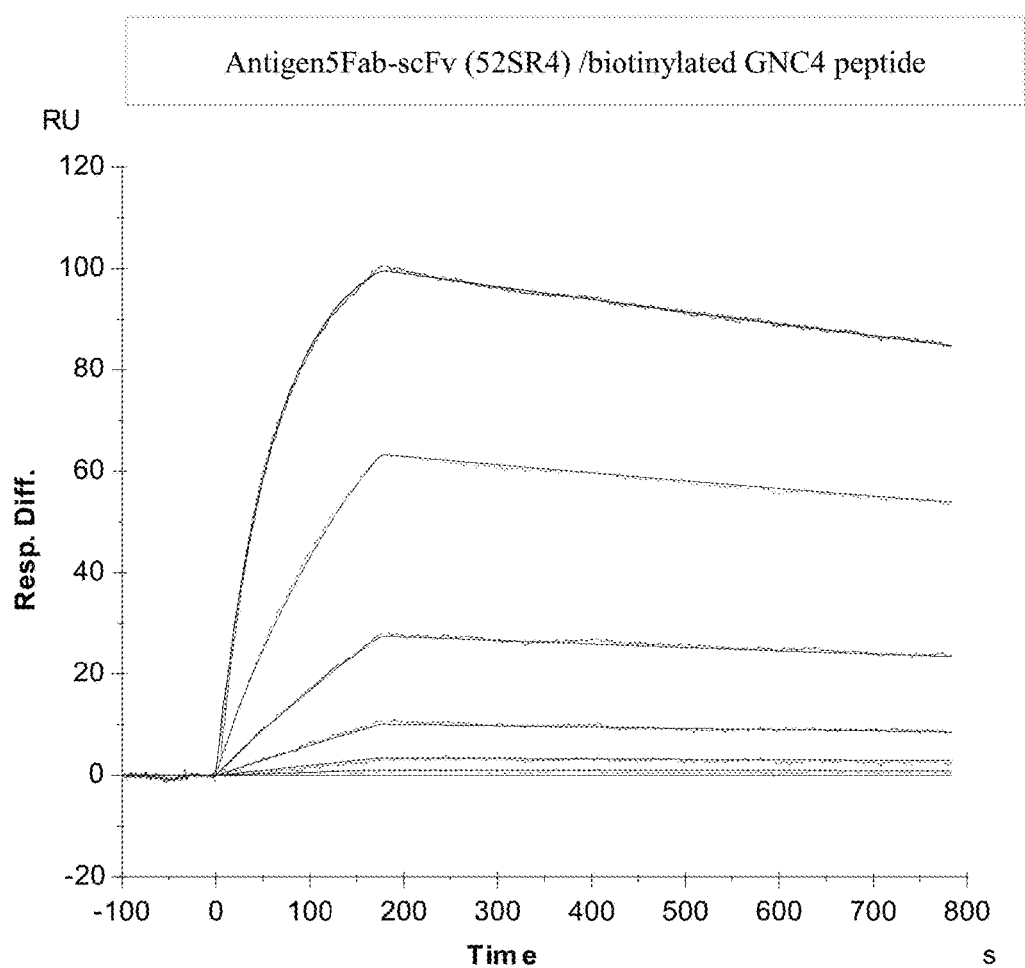
FIG. 13 SPR affinity determination of 52RS4 scFv for GNC4 peptide

FIG. 13 shows a surface plasmon resonance trace which demonstrates the affinity of the scFv:peptide (i.e. 52SR4:GCN4) interaction. Surface plasmon resonance was performed using a Biacore 3000 (GE Healthcare). All experiments were performed at 25° C. Streptavidin (produced in-house) was immobilised on a CM5 Sensor Chip (GE Healthcare) via amine coupling chemistry to a final level of approximately 1750 response units. HBS-N buffer (10 mM HEPES pH 7.4, 0.15M NaCl; GE Healthcare) was used as the running buffer for immobilisation and peptide capture. A 5 µl injection of Biotin-GCN4 peptide in HBS-N (10 nM, M.W. 4360) was used to achieve approximately 6RU of capture on the immobilised streptavidin. The running buffer was switched to HBS-EP+ buffer (10 mM HEPES pH 7.4, 0.15M NaCl, 3 mM EDTA, 0.05% (v/v) surfactant P20; GE Healthcare) for measuring anti-GCN4 (52SR4) scFv binding kinetics. Three-fold serial dilutions of Fab-scFv (generated in-house) from 30 nM, or HBS-EP+ buffer control, were injected over the immobilised GCN4 peptide (3 min association, 15 min dissociation) at a flow rate of 30 µl/min. The surface was regenerated after each injection at a flow-rate of 10 µl/min by two serial 60 sec injection of 2M Guanidine-HCl. Double referenced background subtracted binding curves were analysed using the 3000 BIAEval software (version 4.1) following standard procedures. Kinetic parameters were determined from fitting the 1:1 binding model algorithm. The data demonstrate that the scFv has an affinity for the peptide of 516 pM.

Example 4—Production of Fab-A (Fab-scFv [A-X]) and Fab-B (Fab-peptide [B-Y]) for Binding Assays Cloning Strategy:
Antibody variable region DNA was generated by PCR or gene synthesis with flanking restriction enzyme sites in the DNA sequence. These sites were HindIII and XhoI for variable heavy chains and HindIII and BsiWI for variable light chains. This makes the heavy variable region amenable to ligating into the two heavy chain vectors (pNAFH with FabB-Y and pNAFH with FabA-X) as they have complementary restriction sites. This ligates the variable region upstream (or 5') to the murine constant regions and peptide Y (GCN4) or scFv X (52SR4) creating a whole reading frame. The light chains were cloned into standard in house murine constant kappa vectors (pMmCK or pMmCK S171C) which again use the same complimentary restriction sites. The pMmCK S171C vector is used if the variable region is isolated from a rabbit. The cloning events were confirmed by sequencing using primers which flank the whole open reading frame.

Cultivating CHOS:

Suspension CHOS cells were pre-adapted to CDCHO media (Invitrogen) supplemented with 2 mM (100×) glutamx. Cells were maintained in logarithmic growth phase agitated at 140 rpm on a shaker incubator (Kuner AG, Birsfelden, Switzerland) and cultured at 37° C. supplemented with 8% $CO_2$.

Electroporation Transfection:

Prior to transfection, the cell numbers and viability were determined using CEDEX cell counter (Innovatis AG. Bielefeld, Germany) and required amount of cells ($2\times10^8$ cells/ml) were transferred into centrifuge conical tubes and were spun at 1400 rpm for 10 minutes. The pelleted cells were re-suspended in sterile Earls Balanced Salts Solution and spun at 1400 rpm for further 10 minutes. Supernatant was discarded and pellets were re-suspended to desired cell density.

Vector DNA at a final concentration of 400 µg for $2\times10^8$ cells/ml mix and 800 µl was pipetted into cuvettes (Biorad) and electroporated using in-house electroporation system.

Fab-A (Fab-scFv [A-X]) and Fab-B (Fab-peptide [B-Y]) were transfected separately. Transfected cells were transferred directly into 1×3 L Erlenmeyer Flasks contained ProCHO 5 media enriched with 2 mM glutamx and antibiotic antimitotic (100×) solution (1 in 500) and cells were cultured in Kuhner shaker incubator set at 37° C., 5% $CO_2$ and 140 rpm shaking. Feed supplement 2 g/L ASF (AJINOMOTO) was added at 24 hr post transfection and temperature dropped to 32° C. for further 13 days culture. At day four 3 mM sodium buryrate (n-butric acid sodium Salt, Sigma B-5887) was added to the culture.

On day 14, cultures were transferred to tubes and supernatant separated from the cells after centrifugation for 30 minutes at 4000 rpm. Retained supernatants were further filtered through 0.22 um SARTOBRAN® P Millipore followed by 0.22 µm Gamma gold filters. Final expression levels were determined by Protein G-HPLC.

Large Scale (1.0 L) Purification:

The Fab-A and Fab-B were purified by affinity capture using the AKTA Xpress systems and HisTrap Excel prepacked nickel columns (GE Healthcare). The culture supernatants were 0.22 µm sterile filtered and pH adjusted to neutral, if necessary, with weak acid or base before loading onto the columns. A secondary wash step, containing 15-25 mM imidazole, was used to displace any weakly bound host cell proteins/non-specific His binders from the nickel resin. Elution was performed with 10 mM sodium phosphate, pH7.4+1M NaCl+250 mM imidazole and 2 ml fractions collected. One column volume into the elution the system was paused for 10 minutes to tighten the elution peak, and consequently decrease the total elution volume. The cleanest fractions were pooled and buffer exchanged into PBS (Sigma), pH7.4 and 0.22 µm filtered. Final pools were assayed by A280 Scan, SE-HPLC (G3000 method), SDS-PAGE (reduced & non-reduced) and for endotoxin using the PTS Endosafe system.

Example 5—Bispecific Complex Characterisation

Purification of Fab-X and Fab-Y Reagents:

The formats Fab-X (Fab-scFv-His) and Fab-Y (Fab-peptide-His) were purified as follows after standard CHO expression. Clarified cell culture supernatants were 0.22 µm sterile filtered using a 1 L stericup. The pH was measured and where necessary adjusted to pH7.4. The prepared supernatants were loaded at 5 ml/min onto 5 ml HisTrap Nickel Excel (GE Healthcare) columns equilibrated in 10 mM Sodium phosphate, 0.5 M NaCl, pH7.4. The columns were washed with 15 mM imidazole, 10 mM Sodium phosphate, 0.5M NaCl, pH7.4 and then eluted with 250 mM imidazole, 10 mM Sodium phosphate, 0.5M NaCl, pH7.4. The elution was followed by absorbance at 280 nm and the elution peak collected. The peak elutions were analysed by size exclusion chromatography on a TSKgel G3000SWXL; 5 µm, 7.8×300 mm column developed with an isocratic gradient of 0.2M phosphate, pH7.0 at 1 ml/min, with detection by absorbance at 280 nm. Samples of sufficient purity were concentrated to >1 m/ml and diafiltered into PBS pH7.4 (Sigma Aldrich Chemicals) using Amicon Ultra-15 concentrators with a 10 kDa molecular weight cut off membrane and centrifugation at 4000×g in a swing out rotor. Where product quality was not sufficient the nickel column elutions were concentrated and applied to either a XK16/60 or XK16/60 Superdex200 (GE Healthcare) column equilibrated in PBS, pH7.4 (Sigma Aldrich Chemicals). The columns were developed with an isocratic gradient of PBS, pH7.4 (Sigma Aldrich Chemicals) at 1 ml/min or 2.6 ml/min respectively. Fractions were collected and analysed by size exclusion chromatography on a TSKgel G3000SWXL; 5 µm, 7.8×300 mm column developed with an isocratic gradient of 0.2 M phosphate, pH7.0 at 1 ml/min, with detection by absorbance at 280 nm. Selected fractions were pooled and concentrated to >1 mg/ml using an Amicon Ultra-15 concentrator with a 10 kDa molecular weight cut off membrane and centrifugation at 4000×g in a swing out rotor.

Analysis of Bispecific Formation in Solution

Experiment 1

Purified Fab-X (VR4247) and purified Fab-Y (VR4248) were mixed in a one to one molar ratio, with a total protein concentration of 500 µg/ml and incubated overnight at ambient temperature. Controls consisted of the individual parts of the mixture at the same concentration as they would be in the mixture. 1000 of the sample and each control was injected onto a TSKgel G3000SWXL; 5 µm, 7.8×300 mm column developed with an isocratic gradient of 0.2 M phosphate, pH7.0 at 1 ml/min. Detection was by absorbance at 280 nm (see FIG. 14).

Figure 14:
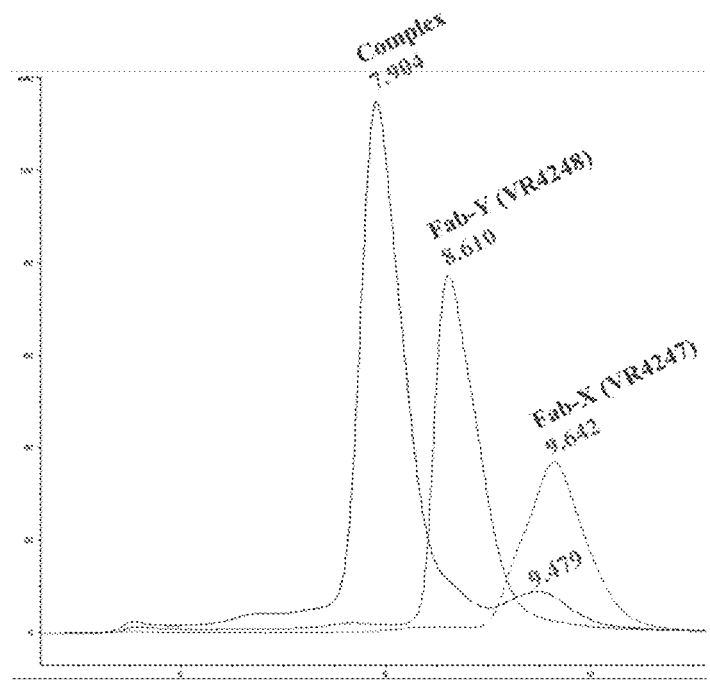
FIG. 14 Size exclusion chromatogram of purified Fab-X (VR4247) and purified Fab-Y (VR4248).

The size exclusion chromatograms in FIG. 14 show that the Fab-X (VR4247) control has a main peak of 92% of the total peak area with a retention time of 8.610 metric minutes. The Fab-Y (VR4248) control has a main peak of 94% of the total peak area with a retention time of 10.767 metric minutes. The retention times measured for the Fab-X and Fab-Y controls were converted to apparent molecular weight of 95 kDa and 35 kDa respectively by using a standard curve created from the retention times of BioRad gel filtration standards (151-1901) run under the same conditions. These apparent molecular weights are consistent with the expected apparent molecular weights for Fab-scFv and Fab-peptide molecules. The main peak for the Fab-X (VR4247)/Fab-Y (VR4248) mixture has a retention time of 9.289 metric minutes. This is converted as above to an apparent molecular weight of 187 kDa. This apparent molecular weight is consistent with that expected for the pairing of one Fab-X (VR4247) with one Fab-Y (VR4248). The main peak is also 84% of the total peak area suggesting that most of the Fab-X (VR4247) and Fab-Y (VR4248) have formed the 1 to 1 bispecific protein complex. The small additional shoulder and peak that elute after the main peak are consistent with the Fab-X (VR4247) and Fab-Y (VR4248) starting materials.

Experiment 2

Purified Fab-X (VR4130) and Fab-Y (VR4131) were mixed in a one to one molar ratio, with a total protein concentration of 500 µg/ml. Aliquots of this mixture were then diluted with PBS pH7.4 to a concentration of 50 µg/ml and 5 µg/ml. Controls consisting of the individual parts of the mixture at the same concentration as they would be in the 500 µg/ml mixture were also set up. All mixtures and controls were incubated overnight at ambient temperature. 100 µl of all samples and controls were injected onto a TSKgel G3000SWXL; 5 µm, 7.8×300 mm column developed with an isocratic gradient of 0.2M phosphate, pH7.0 at 1 ml/min. Detection was by absorbance at 214 nm (see FIG. 15, FIG. 16 and Table 1).

Figure 15:
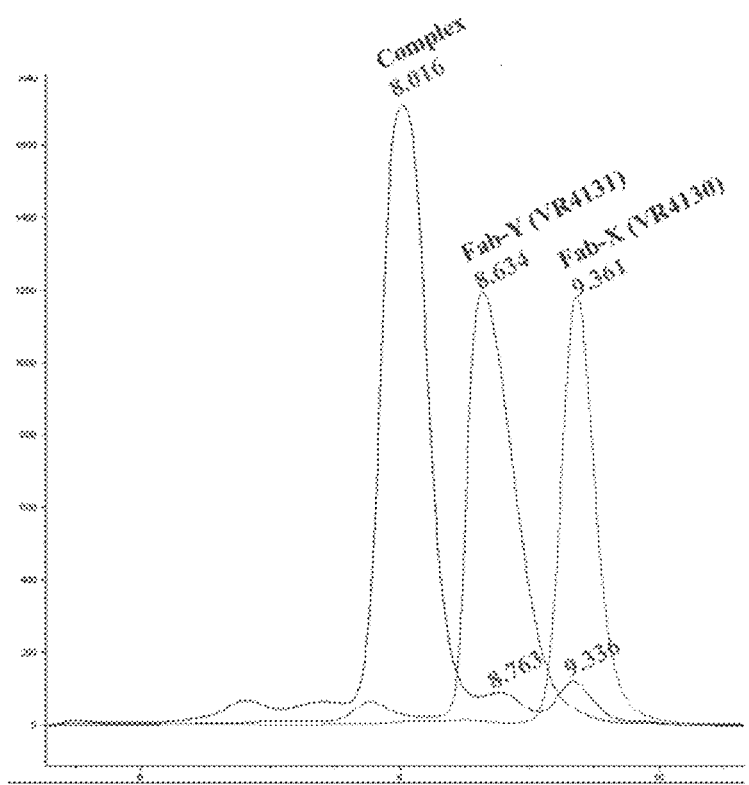
FIG. 15 Size exclusion chromatogram showing the purified Fab-X (VR4130) and Fab-Y (VR4131).

The size exclusion chromatograms in FIG. 15 show that the Fab-X (VR4130) control has a main peak of 91% of total peak area with a retention time of 8.634 metric minutes. The Fab-Y (VR4131) control has a main peak of 97% of total peak area with a retention time of 9.361 metric minutes. The retention times measured for the Fab-X and Fab-Y controls were converted to apparent molecular weights of 109 kDa and 55 kDa respectively by using a standard curve created from the retention times of BioRad gel filtration standards (151-1901) run under the same conditions. These apparent molecular weights are consistent with the expected apparent molecular weights for Fab-scFv and Fab-peptide molecules. The main peak for the Fab-X (VR4130)/Fab-Y (VR4131) mixture has a retention time of 8.016 metric minutes. This was converted as above to an apparent molecular weight of 198 kDa. This apparent molecular weight is consistent with that expected for the pairing of one Fab-X (VR4130) with one Fab-Y (VR4131). The main peak is also 82% of the total peak area suggesting that most of the Fab-X (VR4130) and Fab-Y (VR4131) have formed the 1 to 1 complex. The two small peaks that elute after the main peak are consistent with the Fab-X (VR4130) and Fab-Y (VR4131) starting materials.

Figure 16:
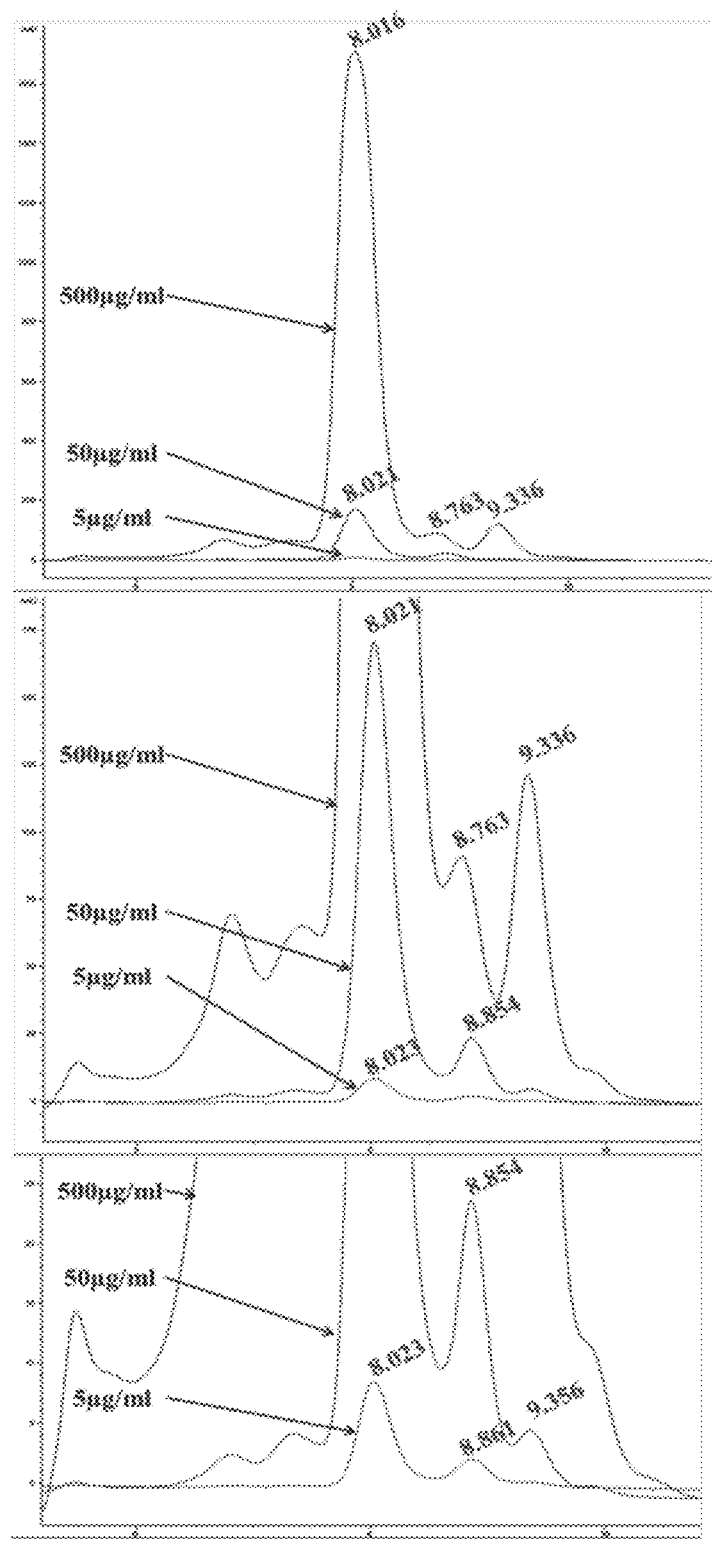
FIG. 16 Size exclusion chromatograms of Fab-X (VR4130)/Fab-Y (VR4131) one to one mixtures at 500 µg/ml, 50 µg/ml and 5 µg/ml concentration.

The size exclusion chromatograms in FIG. 16 are for the Fab-X (VR4130)/Fab-Y (VR4131) 1 to 1 mixtures at 500 µg/ml, 50 µg/ml and 5 µg/ml concentration. All the traces are similar with corresponding peaks between samples having similar retention times and similar relative peak heights and areas. The percentage peak area is collated in Table 5 (Size exclusion peak area data for Fab-X (VR4130)/Fab-Y (VR4131) 1:1 molar ratio mixtures at 500 µg/ml, 50 µg/ml and 5 µg/ml. Peaks were detected at an absorbance of 214 nm), where the % of each peak remains fairly constant upon dilution of the mixture. This indicates that the Fab-X/Fab-Y 1 to 1 complex remains as a complex at all the concentrations tested. 75% of the Fab-X and Fab-Y are present as the 1 to 1 complex even when the mixture is diluted to 5 µg/ml which is equivalent to concentration of 40 nM for the complex.

TABLE 5

| Concentrations | | % Peak Area | | |
|---|---|---|---|---|
| µg/ml | nM | Fab-X (VR4130)/Fab-Y (VR4131) 1 to 1 complex | Fab-X (VR4130) | Fab-Y (VR4131) |
| 500 | 4000 | 82% | 4% | 5% |
| 50 | 400 | 81% | 11% | 3% |
| 5 | 40 | 75% | 21% | 3% |

Hence, the results of these experiments indicate that a high proportion of the Fab-X and Fab-Y fusion proteins form the desired bispecific complexes, with a minimal proportion of monomers left over and no evidence of homodimer formation.

Example 6—Demonstration of Binding of Anti-CD138 and Anti-CH1 Fab-X and Fab-Y

V regions specific for CD138 expressed on human plasma cells and V regions to human CH1 to detect secreted human IgG were expressed and purified and tested for individual binding activities pre-complex formation for the capture of human IgG to human plasma cells.

Antibody Discovery by B Cell Culture & Isolation:

Rabbits were immunised with 3 doses of Rab-9 cells expressing human CD138 or purified human Fab protein.

B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 µl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$.

The presence of antigen-specific antibodies in B cell culture supernatants was determined using a homogeneous fluorescence-based binding assay using HEK293 cells expressing CD138 or furified CD138 or Fab protein. Screening involved the transfer of 10 ul of supernatant from barcoded 96-well tissue culture plates into barcoded 384-well black-walled assay plates containing HEK293 cells transfected with target antigen or protein using a Matrix Platemate liquid handler. Binding was revealed with a goat anti-rabbit IgG Fcγ-specific Cy-5 conjugate (Jackson). Plates were read on an Applied Biosystems 8200 cellular detection system.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and Superavidin™ beads (Bangs Laboratories) coated with recombinant protein or antigen transfected HEK cells. This was done to confirm the specificity of the cloned antibodies.

Production of Small Scale Fab A-X and Fab B-Y

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed Expi293™ Expression Medium for each 50 mL transfection.

To prepare the lipid-DNA complexes for each transfection a total of 50 μs of heavy chain and light chain plasmid DNAs were diluted in Opti-MEM® I medium (LifeTechnologies) to a total volume of 2.5 mL and 135 μL of ExpiFectamine™ 293 Reagent (LifeTechnologies) was diluted in Opti-MEM® I medium to a total volume of 2.5 mL. All dilutions were mixed gently and incubate for no longer than 5 minutes at room temperature before each DNA solution was added to the respective diluted ExpiFectamine™ 293 Reagent to obtain a total volume of 5 mL. The DNA-ExpiFectamine™ 293 Reagent mixtures were mixed gently and incubated for 20-30 minutes at room temperature to allow the DNA-ExpiFectamine™ 293 Reagent complexes to form.

After the DNA-ExpiFectamine™ 293 reagent complex incubation was completed, the 5 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 μL of ExpiFectamine™ 293 Transfection Enhancer 1 (LifeTechnologies) and 2.5 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 μm sterile filtered before 500 μL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Anti-Human IgG Binding Assay

Whole human IgG was coated onto a Nunc ELISA plate at 1 μg/mL in PBS overnight at room temperature. Some wells were left uncoated as negative controls for the assay. The plate was washed 4 times in PBS 0.01% Tween, then blocked with PBS 1% BSA (200 μL per well) for 1 hr. The plate was washed 4 times in PBS 0.01% Tween. Anti-CH1 Fab' Xds, anti-CH1 Fab' Y and an anti-CD138 Fab' Y (as a negative control) were titrated from 1 μg/mL in 1/3 serial dilutions in PBS 1% BSA and added to the hIgG coated plate at 100 μL per well. The plate was incubated for 2 hrs. The plate was washed 4 times in PBS 0.01% Tween. A peroxidase conjugated anti-mouse IgG was diluted 1 in 10000 in PBS 1% BSA, added at 100 μL per well and incubated for 1 hr. The plate was washed 4 times in PBS 0.01% Tween. 100 μL of TMB was added to each well and the plate was left to develop for 20 minutes before stopping the reaction with 50 μL TMB stop solution. The well absorbance was read on the Synergy2 at 450 nm.

Figure 17:
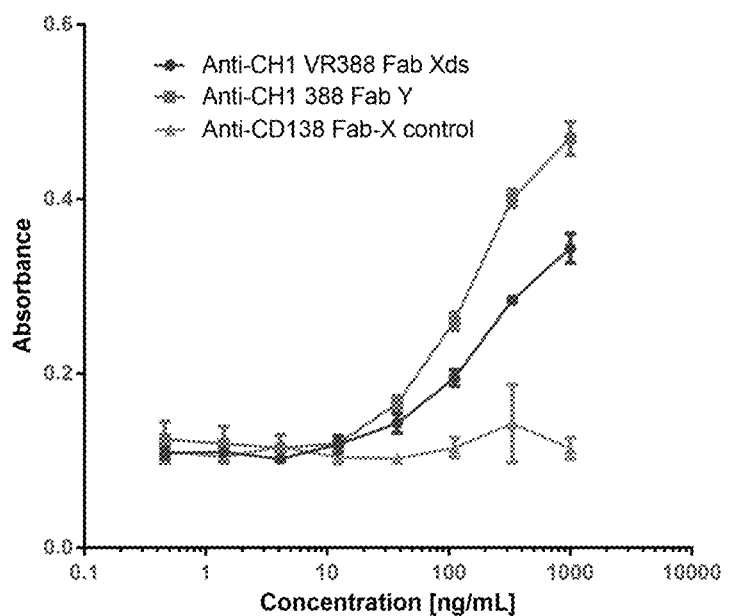
FIG. 17 Human IgG binding.

FIG. 17 shows that in both Fab-X and Fab-Y formats, the anti-human CH1 V regions (VR388) can bind to human IgG CD138 Binding Assay In vitro differentiated plasma blasts expressing high levels of CD138 were plated out in 96 well U-plates at $5 \times 10^4$/well and incubated with 1 μg/mL of each of the anti-human CD138 Fab' Y diluted in FACS buffer (PBS 5% FCS, 2 mM sodium azide) for 30 min on ice. Cells were washed by addition of 100 μL FACS buffer to each well and spun at 500 g for 5 min. FACS buffer was aspirated and a second wash step carried out by addition of 200 μL per well of FACS buffer followed by spin at 500 g for 5 min. FACS buffer was aspirated once more and the cell pellet was loosened by placing the plate on a plate shaker for 10 seconds at 1400 rpm. Secondary detection antibody (FITC conjugated anti-mouse IgG Jackson Immuno Research 115-095-072) diluted at 1:200 in FACS buffer was added to cells at 100 μL per well. Cells were incubated with detection Ab for 30 min on ice and washed once more as described above. Cells were immediately acquired on the iQue. Geometric mean of the FL-1 was plotted in Prism.

Figure 1:
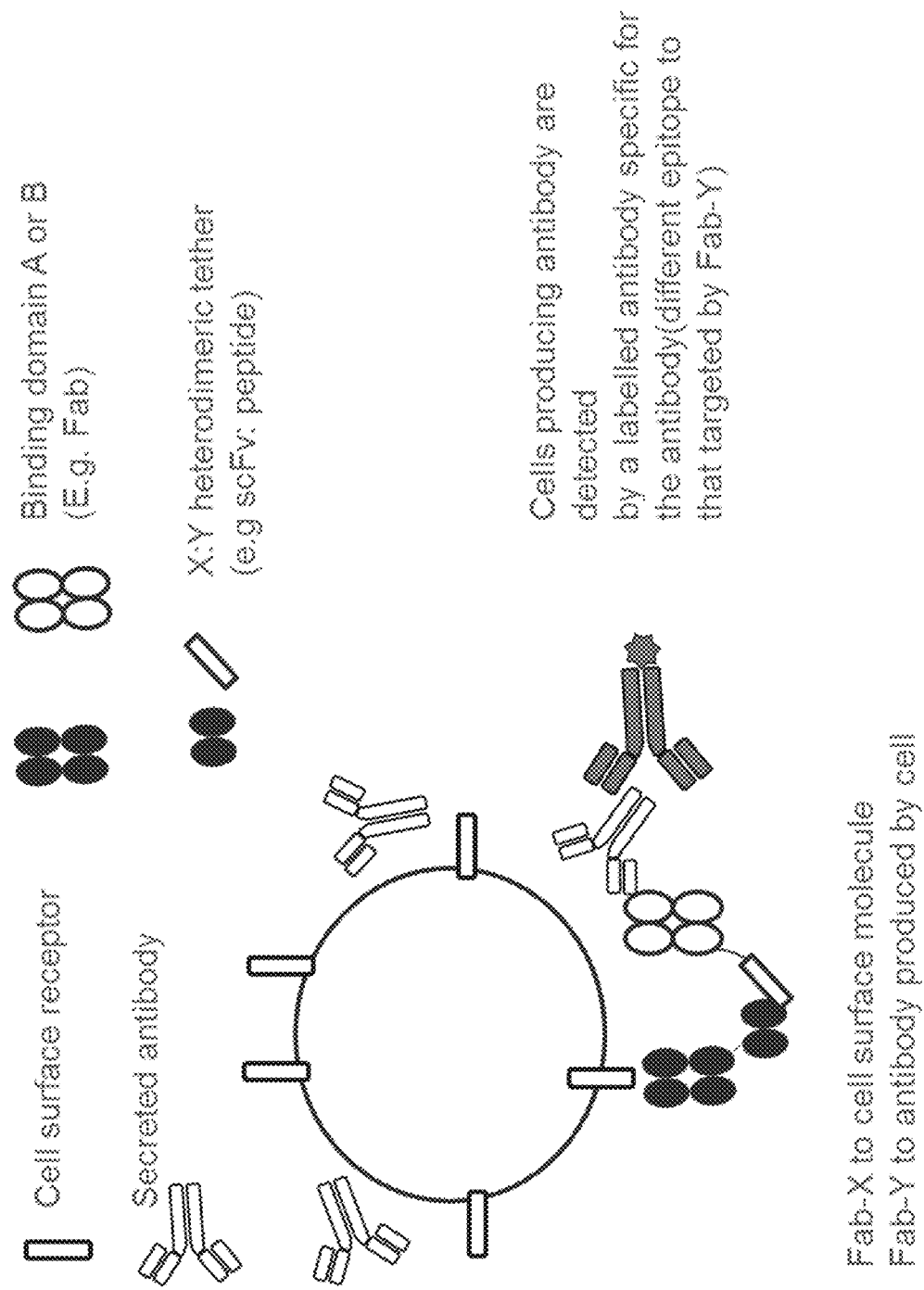
FIG. 1 shows a Fab-scFv (A-X respectively labelled Fab-X in the figure) complexed to a peptide-Fab (Y-B respectively labelled Fab-Y in the figure) wherein Fab A is bound to (specific to) a cell surface receptor and Fab B binds to (is specific to) and immunoglobulin secreted from the cell, and the detection system is a labelled antibody that binds, for example the constant region of the immunoglobulin secreted from the cell.
Figure 18:
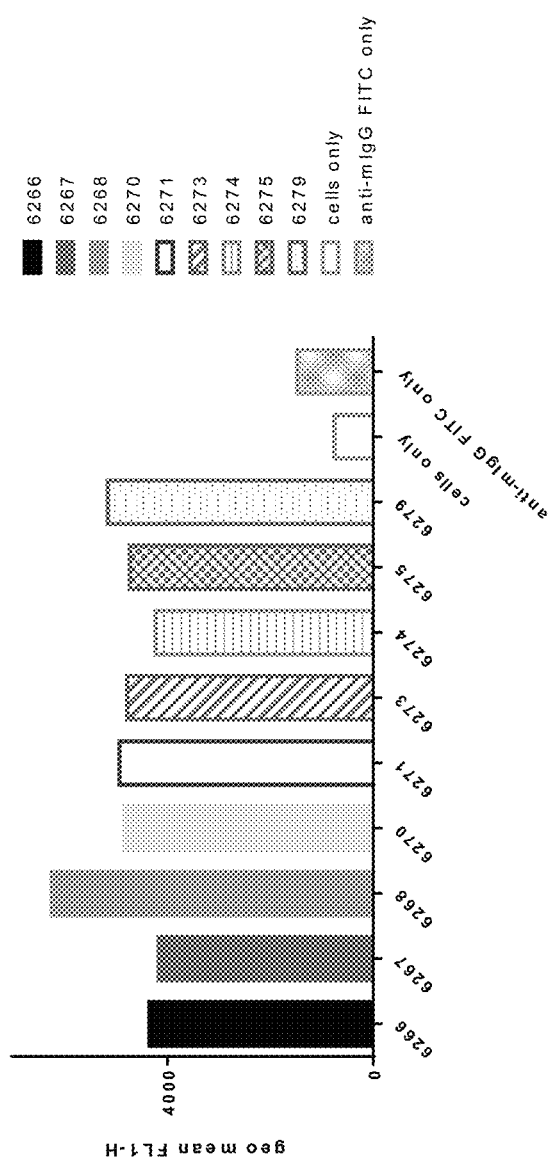
FIG. 18 anti-CD138 binding to plasma cells.

FIG. 18 shows the binding of Fab-Y constructs with different anti-CD138 V regions binding to human plasma cells Method for Identification of Antibody Secreting Cells A-X binds a cell surface receptor expressed on antibody producing cells and B-Y binds the secreted antibody either via the Fc or the Fab'. The secreted antibody is captured to the cell surface by the interaction between X and Y. The cell-captured antibody can then be detected by addition of a labelled anti-antibody reagent either to the Fc or the Fab. The epitope bound by B-Y on the secreted antibody is different to that recognised by the added detection antibody. See for example FIG. 1.

A may be independently selected from anti-CD38, anti-CD138, anti-CD45 (including all isoforms), anti-CD27, anti-CD19, anti-CD20 (most preferably anti-CD38 and CD138).

B may be independently selected from anti-CH1, anti-Cκ, anti-Cλ, anti-Fc pan isotypes, anti-Fc IgG1, 2, 3, 4, IgE or IgA specific.

X may be anti-peptide scFv or sdAb e.g. 52SR4

Y may be a peptide that binds X (for example GCN4).

Example 7—Total or Isotype Specific Antibody Producing Cells

Figure 2:
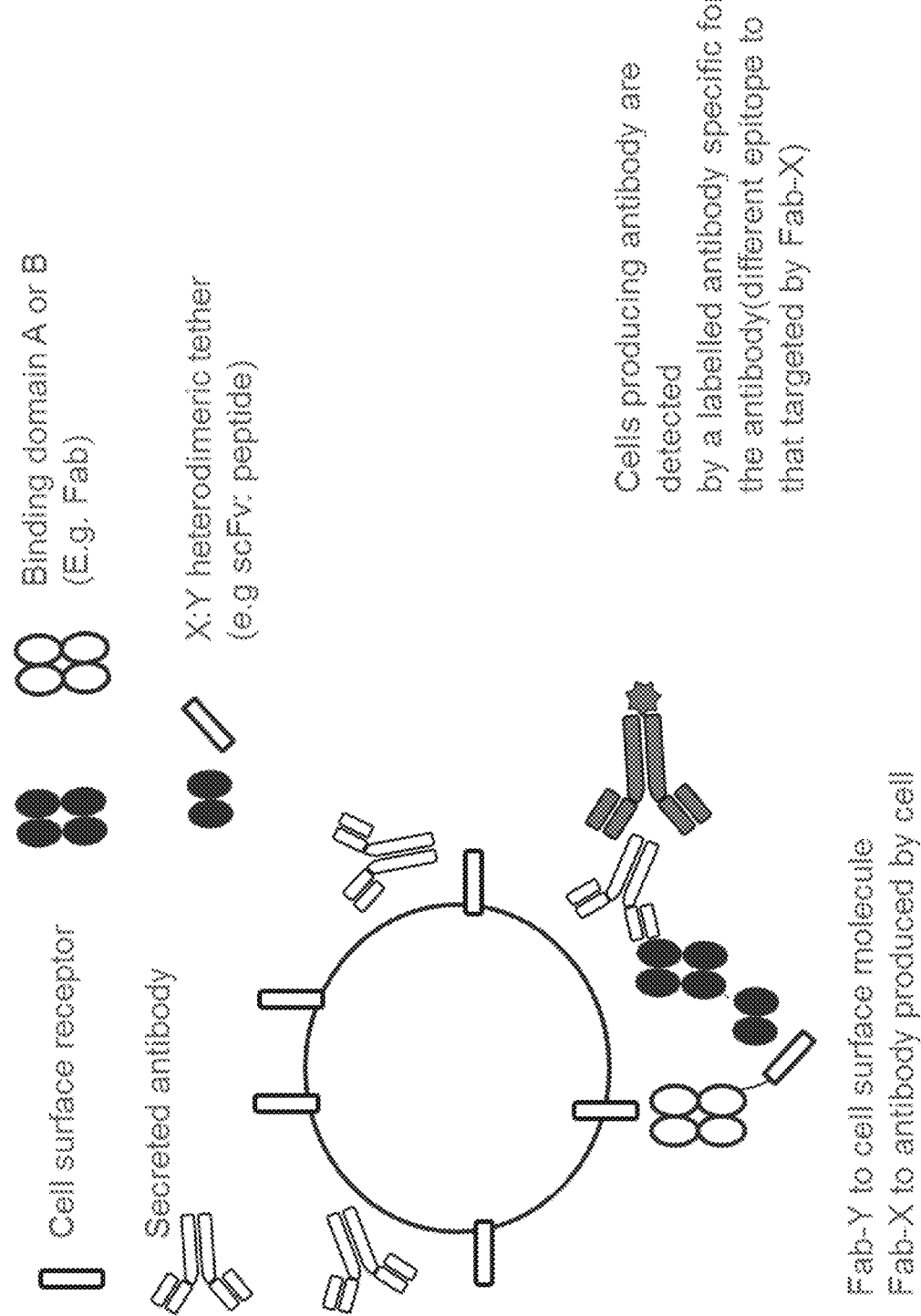
FIG. 2 shows a Fab-peptide (A-X respectively labelled Fab-X in the figure) complexed to a scFv-Fab (Y-B respectively labelled Fab-Y in the figure) wherein Fab A is bound to (specific to) a cell surface receptor and Fab B binds to (is specific to) and immunoglobulin secreted from the cell, and the detection system is a labelled antibody, for example the constant region of the immunoglobulin secreted from the cell.

A-Y binds a cell surface receptor expressed on antibody producing cells and A-Y binds a cell surface receptor expressed on antibody producing cells and B-X binds the secreted antibody either via the Fc or the Fab'. The secreted antibody is captured to the cell surface by the interaction between X and Y. The cell-captured antibody can then be detected by addition of a labelled anti-antibody reagent either to the Fc or the Fab. The epitope bound by B-X on the secreted antibody is different to that recognised by the added detection antibody. See for example FIG. 2.

Specific Examples

A may be independently selected from anti-CD38, anti-CD138, anti-CD45 (including all isoforms), anti-CD27, anti-CD19, and anti-CD20 (for example anti-CD38 and CD138). B may be independently selected from an anti-CH1, anti-Cκ, anti-Cλ, anti-Fc pan isotypes, anti-Fc IgG1, 2, 3, 4, IgE or IgA specific.

Y may be an anti-peptide scFv or sdAb e.g. 52SR4

X may be a peptide that binds Y (for example GCN4)

Example 8—Antigen Specific Antibody Producing Cells

A-Y binds a cell surface receptor expressed on antibody producing cells and B-X binds the antigen that the secreted antibody is also specific for. Antigen is thereby firstly captured to the cell surface by the interaction between X and Y and then the secreted antibody binds to the antigen and is itself captured to the cell surface. The secreted antibody which is now cell-captured can then be detected by the addition of a labelled anti-antibody reagent either to the Fc or the Fab, and can be pan or isotype specific. See, for example FIG. 3.

Specific Examples

A may be independently selected from anti-CD38, anti-CD138, anti-CD45, anti-CD27, anti-CD19, anti-CD20 (most preferably anti-CD38 and CD138).

B may be independently selected from Tagged antigen of interest. Tag=biotin, His, Myc.

X may be an anti-peptide scFv or sdAb e.g. 52SR4

Y may be a peptide that binds X (for example GCN4)

The detection antibody may independently selected from anti-CH1, anti-Cκ, anti-Cλ, anti-Fc pan isotypes, anti-Fc IgG1, 2, 3, 4, IgE or IgA specific.

Example 9—Antigen Specific Antibody Producing Cells

Figure 4:
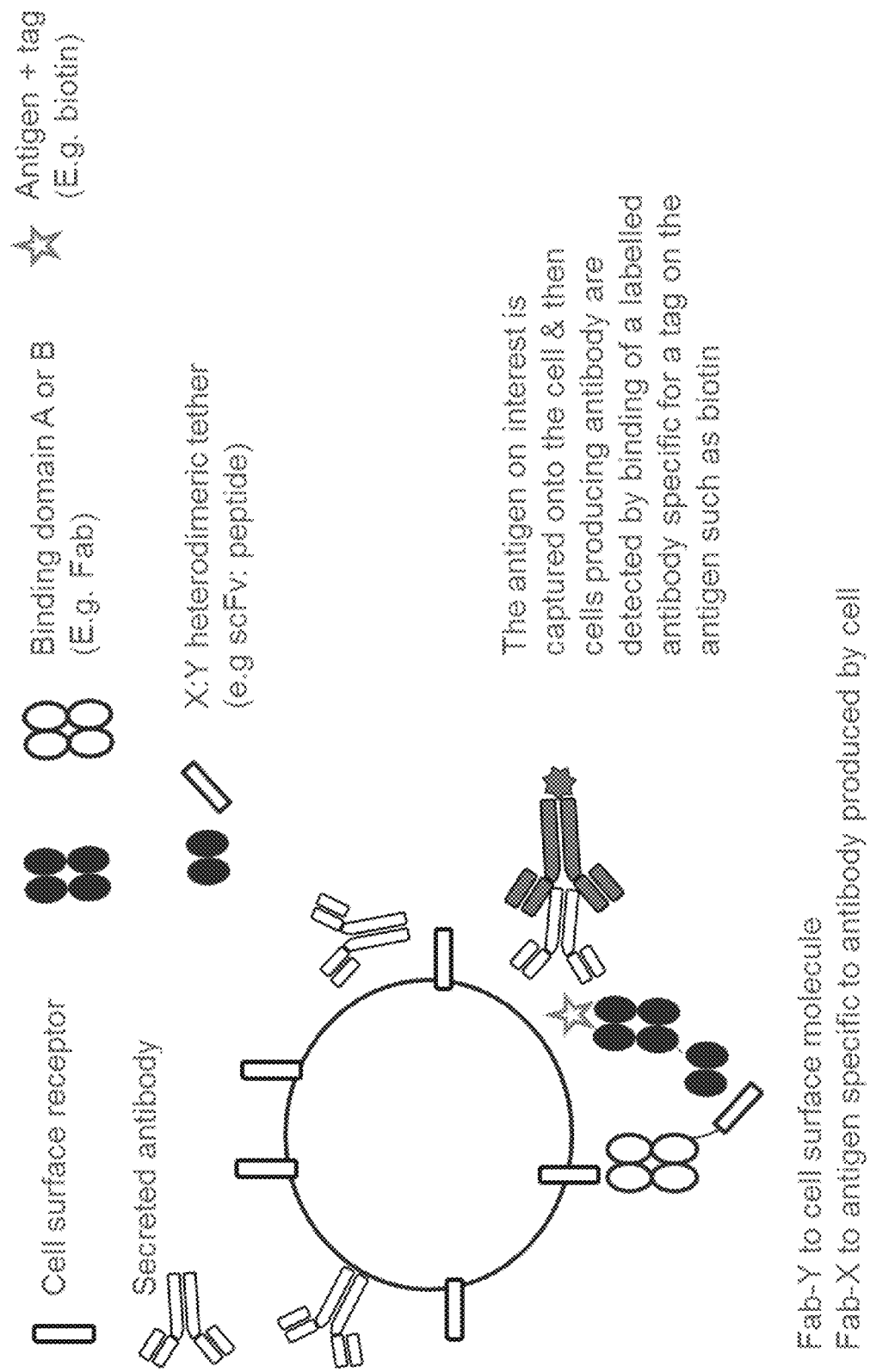
FIG. 4 shows a Fab-peptide (A-X respectively) in complex with to a scFv-Fab (Y-B respectively) wherein Fab A is bound to (specific to) a cell surface receptor and Fab B binds to (is specific to) an antigen which is also bound by a immunoglobulin secreted from the cell, and the detection system is a labelled antibody. Fab B and the secreted immunoglobulin bind different epitopes on the antigen.

A-X binds a cell surface receptor expressed on antibody producing cells and B-Y binds the antigen that the secreted antibody is also specific for. Antigen is thereby firstly captured to the cell surface by the interaction between X and Y and then the secreted antibody binds to the antigen and is itself captured to the cell surface. The secreted antibody which is now cell-captured can then be detected by the addition of a labelled anti-antibody reagent either to the Fc or the Fab, and can be pan or isotype specific. See for example FIG. 4

Specific Examples

A may be independently selected from anti-CD38, anti-CD138, anti-CD45, anti-CD27, anti-CD19, anti-CD20 (most preferably anti-CD38 and CD138).

B may be independently selected from Tagged antigen of interest. Tag=biotin, His, Myc.

Y may be an anti-peptide scFv or sdAb e.g. 52SR4

X may be a peptide that binds Y (for example GCN4)

The detection antibody=anti-CH1, anti-Cκ, anti-Cλ, anti-Fc pan isotypes, anti-Fc IgG1, 2, 3, 4, IgE or IgA specific.

Example 10—Antigen Specific Antibody Producing Cells

Figure 5:
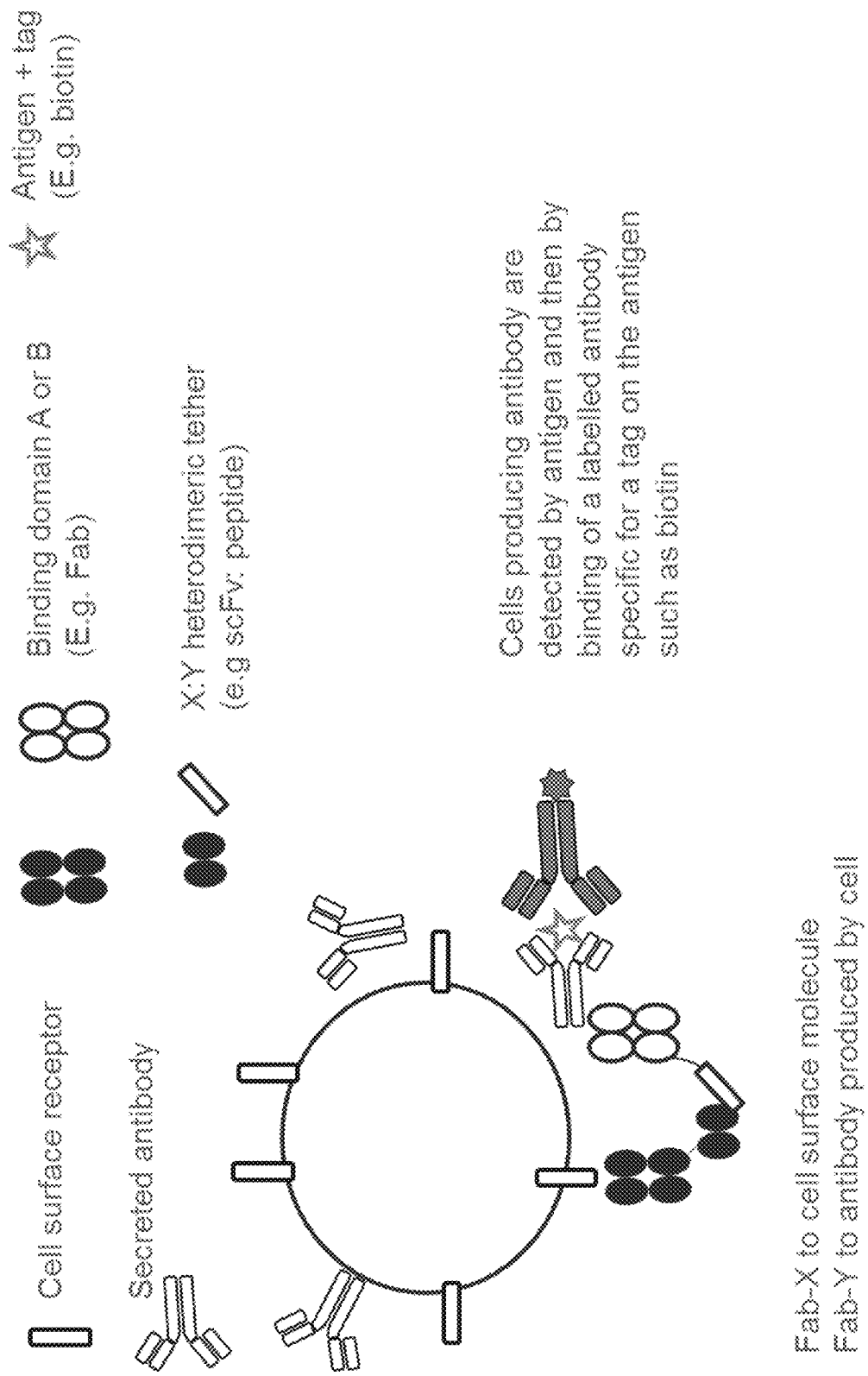
FIG. 5 shows a Fab-scFv (A-X respectively) in complex with to a peptide-Fab (Y-B respectively) wherein Fab A is bound to (specific to) a cell surface receptor and Fab B binds to (is specific to) and immunoglobulin secreted from the cell, and the detection system is a labelled antibody that binds, an antigen (also optionally labelled) which is also bound by the immunoglobulin secreted from the cell. That is the labelled antibody indirectly labels the secreted immunoglobulin.

A-X binds a cell surface receptor expressed on antibody producing cells and B-Y binds the secreted antibody either via the Fc or the Fab'. The secreted antibody is captured to the cell surface by the interaction between X and Y. Antigen-specific cell-captured antibody can then be detected by addition of the antigen with Tag and then a labelled anti-Tag antibody reagent. A may be independently selected from anti-CD38, anti-CD138, anti-CD45 (including all isoforms), anti-CD27, anti-CD19, anti-CD20 (most preferably anti-CD38 and CD138). See, for example FIG. 5.

B may be independently selected from anti-CH1, anti-Cκ, anti-Cλ, anti-Fc pan isotypes, anti-Fc IgG1, 2, 3, 4, IgE or IgA specific.

X may be an anti-peptide scFv or sdAb e.g. 52SR4

Y may be a peptide that binds X (for example GCN4)

Example 11—Antigen Specific Antibody Producing Cells

A-Y binds a cell surface receptor expressed on antibody producing cells and B-X binds the secreted antibody either via the Fc or the Fab'. The secreted antibody is captured to the cell surface by the interaction between X and Y. This antigen-specific cell-captured antibody can then be detected by addition of the antigen with Tag and then a labelled anti-Tag antibody reagent. See, for example FIG. 6

A may be independently selected from anti-CD38, anti-CD138, anti-CD45 (including all isoforms), anti-CD27, anti-CD19, anti-CD20 (most preferably anti-CD38 and CD138). B may be independently selected from anti-CH1, anti-Cκ, anti-Cλ, anti-Fc pan isotypes, anti-Fc IgG1, 2, 3, 4, IgE or IgA specific.

Y may be an anti-peptide scFv or sdAb e.g. 52SR4

X may be a peptide that binds Y (for example GCN4)

Example 12—Antigen Specific Antibody Producing Cells

A-X binds a cell surface receptor expressed on antibody producing cells and Antigen-Y binds the secreted antibody.

Figure 7:
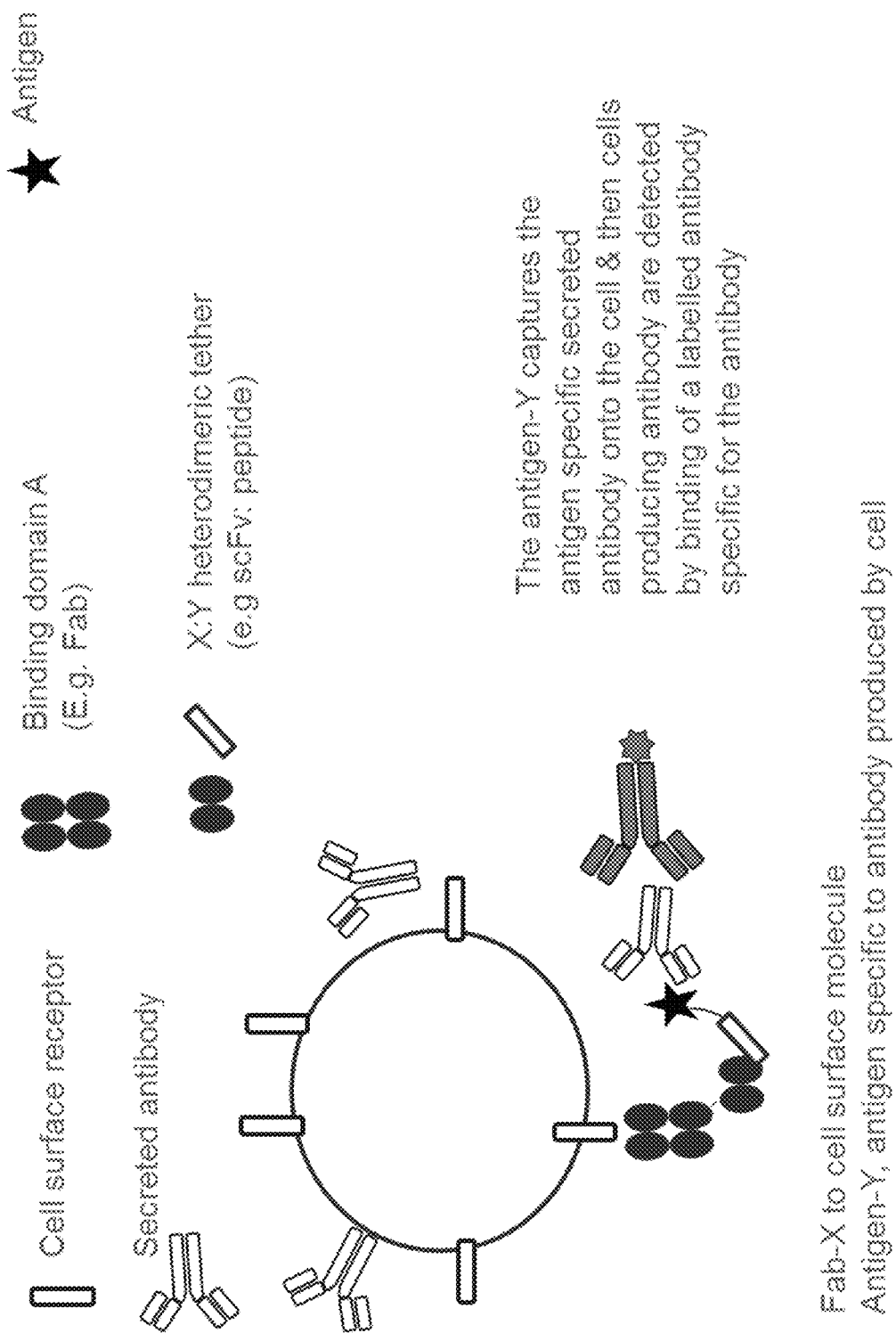
FIG. 7 shows a Fab-scFv (A-X respectively) in complex with to a peptide-antigen (Y-B respectively) wherein Fab A is bound to (specific to) a cell surface receptor and antigen B is bound specifically by immunoglobulin secreted from the cell, and the detection system is a labelled antibody that binds, for example the constant region of the secreted immunoglobulin.

The secreted antibody is captured to the cell surface by the interaction between X and Y. This antigen-specific cell-captured antibody can then be detected by addition of a labelled anti-antibody reagent either to the Fc or the Fab, and can be pan or isotype specific. See for example FIG. 7.

A may be independently selected from anti-CD38, anti-CD138, anti-CD45 CD45 (including all isoforms), anti-CD27, anti-CD19, anti-CD20 (for example anti-CD38 and CD138).

B is antigen

Detection antibody may be independently selected from anti-CH1, anti-Cκ, anti-Cλ, anti-Fc pan isotypes, anti-Fc IgG1, 2, 3, 4, IgE or IgA specific.

X may be an anti-peptide scFv or sdAb e.g. 52SR4

Y may be a peptide that binds X (for example GCN4)

Example 13—Antigen Specific Antibody Producing Cells

Figure 8:
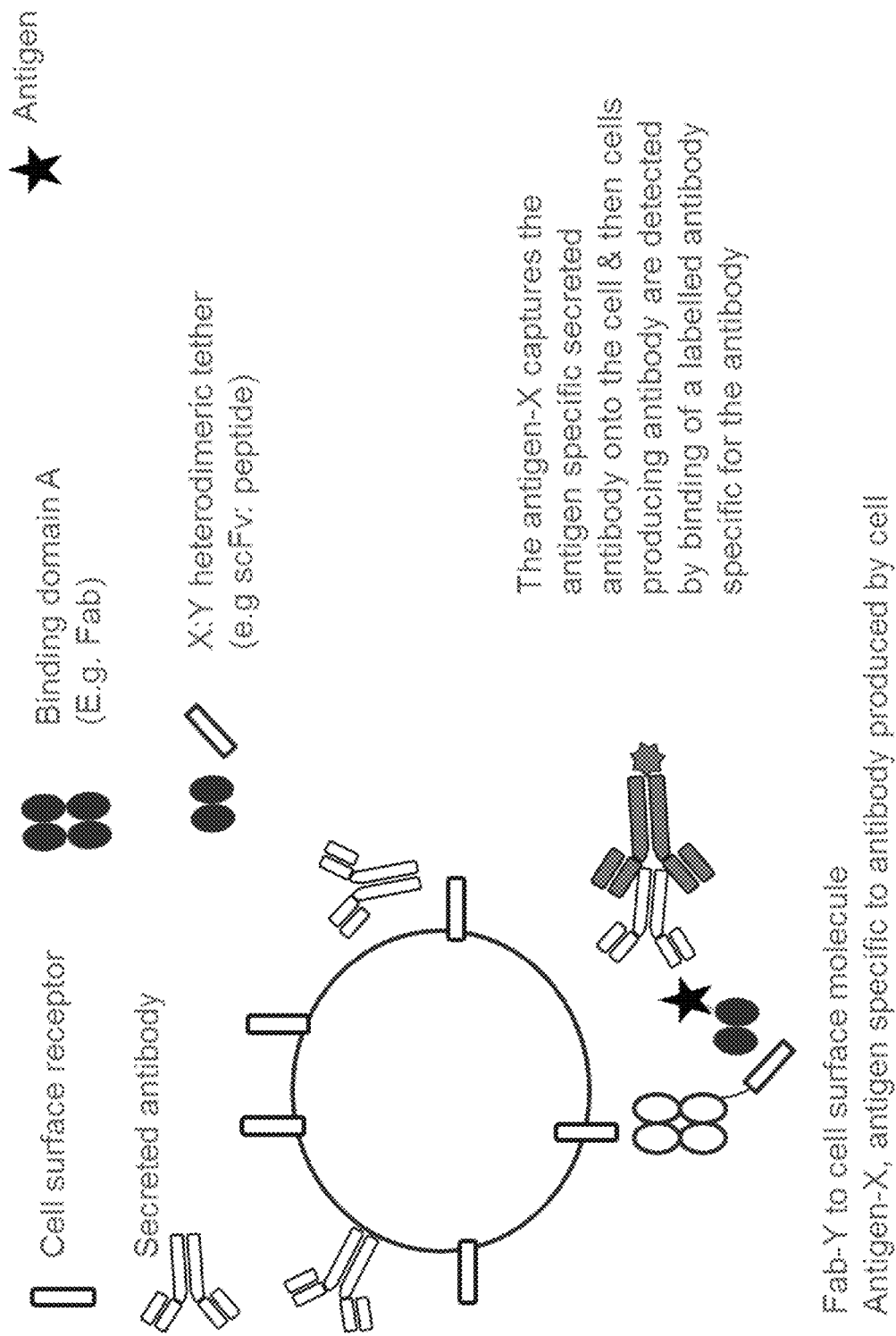
FIG. 8 shows a Fab-peptide (A-X respectively) in complex with to a scFv-antigen (Y-B respectively) wherein Fab A is bound to (specific to) a cell surface receptor and antigen B is bound specifically by immunoglobulin secreted from the cell, and the detection system is a labelled antibody that binds, for example the constant region of the secreted immunoglobulin.

A-Y binds a cell surface receptor expressed on antibody producing cells and Antigen-X binds the secreted antibody. The secreted antibody is captured to the cell surface by the interaction between X and Y. This antigen-specific cell-captured antibody can then be detected by addition of a labelled anti-antibody reagent either to the Fc or the Fab, and can be pan or isotype specific. See for example FIG. 8.

A may be independently selected anti-CD38, anti-CD138, anti-CD45 CD45 (including all isoforms), anti-CD27, anti-CD19, anti-CD20 (most preferably anti-CD38 and CD138).

B is antigen

Detection antibody may be independently selected anti-CH1, anti-Cκ, anti-Cλ, anti-Fc pan isotypes, anti-Fc IgG1, 2, 3, 4, IgE or IgA specific Y may be an anti-peptide scFv or sdAb e.g. 52SR4

X may be a peptide that binds Y (for example GCN4)

Example 14—Identification of Soluble Molecule Secreting Cells

Use of bispecific protein complexes according to the disclosure for the identification of cells producing a soluble molecule for isolation, examination or targeting.

Figures 9A, 9B:
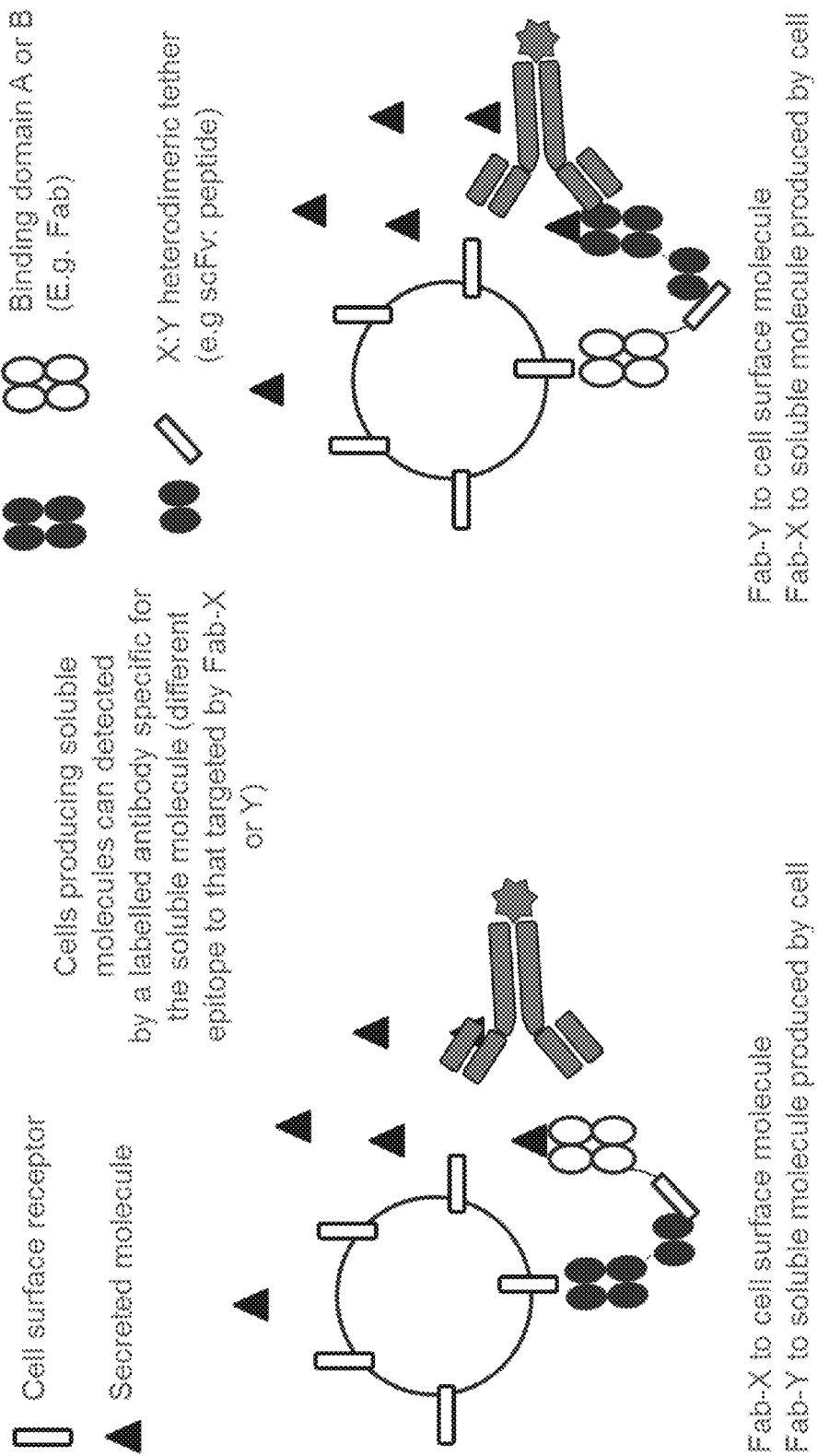
FIG. 9A shows a Fab-scFv (A-X respectively) in complex with to a peptide-Fab (Y-B respectively) wherein Fab A is bound to (specific to) a cell surface receptor and Fab B binds specifically to a molecule secreted from the cell, and the detection system is a labelled antibody that binds to the soluble molecule. Fab B and the detection labelled antibody bind different epitopes on the soluble molecule.
FIG. 9B shows a Fab-peptides (A-X respectively) in complex with to a scFv-Fab (Y-B respectively) wherein Fab A is bound to (specific to) a cell surface receptor and Fab B binds specifically to a molecule secreted from the cell, and the detection system is a labelled antibody that binds to the soluble molecule. Fab B and the detection labelled antibody bind different epitopes on the soluble molecule.

A-X binds a cell surface receptor expressed on cells producing a soluble molecule of interest and B-Y binds the soluble molecule. The secreted soluble molecule is captured to the cell surface by the interaction between X and Y. Cell-captured secreted molecule (& hence the cell that secreted it) can then be detected by addition of a labelled antibody specific to the soluble molecule which would need to bind at different epitope to that targeted by B-Y. See for example FIG. 9A.

A may be independently selected from anti-any cell surface receptor that characterises a cell sub-set on interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

B may be independently selected from anti-any soluble molecule cytokine, chemokine, hormone etc.

X may be an anti-peptide scFv or sdAb e.g. 52SR4

Y may be a peptide that binds X (for example GCN4)

Example 15—Identification of Soluble Molecule Secreting Cells

Use of bispecific protein complexes according to the disclosure for the identification of cells producing a soluble molecule for isolation, examination or targeting.

A-X binds a cell surface receptor expressed on cells producing a soluble molecule of interest and B-Y binds the soluble molecule. The secreted soluble molecule is captured to the cell surface by the interaction between X and Y. Cell-captured secreted molecule (& hence the cell that secreted it) can then be detected by addition of a labelled antibody specific to the soluble molecule which would need to bind at different epitope to that targeted by B-Y. See for example FIG. 9B.

A may be independently selected from anti-any cell surface receptor that characterises a cell sub-set on interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

B may be independently selected from anti-any soluble molecule cytokine, chemokine, hormone etc.

Y may be an anti-peptide scFv or sdAb e.g. 52SR4

X may be a peptide that binds Y (for example GCN4)

Example 16—Screening Cells to Establish which Cell Types Produce a Particular Soluble Molecule Use of bispecific protein complexes according to the disclosure for the identification of which cell sub-sets produce a soluble molecule of interest in a mixed cell system.

A-X binds a cell surface receptor expressed on cells potentially producing a soluble molecule of interest and B-Y binds the soluble molecule. A large number of different A-X cell surface specificities can be complexed with B-Y to a selected soluble molecule in different assays.

The secreted soluble molecule is captured to the cell surface by the interaction between X and Y. Cell-captured secreted molecule (& hence the cell that secreted it) can then be detected by addition of a labelled antibody specific to the soluble molecule but binding at different epitope to that targeted by B-Y. This ability to use different A-X specificities facilitates identification of which cells secrete a particular soluble molecule.

A may be independently selected from anti-any cell surface receptor that characterises a cell sub-set on interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

B may be independently selected from anti-any soluble molecule cytokine, chemokine, hormone etc.

X may be an anti-peptide scFv or sdAb e.g. 52SR4

Y may be a peptide that binds X (for example GCN4)

Example 17—Screening Cells to Establish which Cell Types Produce a Particular Soluble Molecule Use of bispecific protein complexes according to the disclosure for the identification of which cell sub-sets produce a soluble molecule of interest in a mixed cell system.

A-X binds a cell surface receptor expressed on cells potentially producing a soluble molecule of interest and B-Y binds the soluble molecule. A large number of different A-X cell surface specificities can be complexed with B-Y to a selected soluble molecule in different assays.

The secreted soluble molecule is captured to the cell surface by the interaction between X and Y. Cell-captured secreted molecule (& hence the cell that secreted it) can then be detected by addition of a labelled antibody specific to the soluble molecule but binding at different epitope to that targeted by B-Y. This ability to use different A-X specificities facilitates identification of which cells secrete a particular soluble molecule.

A may be independently selected from anti-any cell surface receptor that characterises a cell sub-set on interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

B may be independently selected from anti-any soluble molecule cytokine, chemokine, hormone etc.

Y may be an anti-peptide scFv or sdAb e.g. 52SR4

X may be a peptide that binds Y (for example GCN4)

Example 18—Screening Cells to Establish which Soluble Molecules a Particular Cell Type Makes Use of bispecific protein complexes according to the disclosure for the identification of which soluble molecules a particular cell sub-set of interest secretes in a mixed cell system.

A-X binds a cell surface receptor expressed on cells in a mixed cell population potentially producing soluble molecules of interest and B-Y binds a soluble molecule. A large number of different B-Y soluble molecule specificities can be complexed with A-X to a selected cell surface molecule. The secreted soluble molecule is captured to the cell surface by the interaction between X and Y. Cell-captured secreted molecule can then be detected by addition of a labelled antibody specific to the soluble molecule but binding at different epitope to that targeted by B-Y. This ability to easily use different B-Y specificities facilitates identification of what soluble molecules a particular cell secretes.

A may be independently selected from anti-CD38, anti-CD138, anti-CD45 (including all isoforms), anti-CD27, anti-CD19, anti-CD20 (most preferably anti-CD38 and CD138). B may be independently selected from anti-CH1, anti-Cκ, anti-Cλ, anti-Fc pan isotypes, anti-Fc IgG1, 2, 3, 4, IgE or IgA specific.

B may be independently selected from anti-anti-any soluble molecule cytokine, chemokine, hormone etc.

X may be an anti-peptide scFv or sdAb e.g. 52SR4

Y may be a peptide that binds X (for example GCN4)

Example 19—Screening Cells to Establish which Soluble Molecules a Particular Cell Type Makes Use of bispecific protein complexes according to the disclosure for the identification of which soluble molecules a particular cell sub-set of interest secretes in a mixed cell system.

A-X binds a cell surface receptor expressed on cells in a mixed cell population potentially producing soluble molecules of interest and B-Y binds a soluble molecule. A large number of different B-Y soluble molecule specificities can be complexed with A-X to a selected cell surface molecule. The secreted soluble molecule is captured to the cell surface by the interaction between X and Y. Cell-captured secreted molecule can then be detected by addition of a labelled antibody specific to the soluble molecule but binding at different epitope to that targeted by B-Y. This ability to easily use different B-Y specificities facilitates identification of what soluble molecules a particular cell secretes.

A may be independently selected from anti-any cell surface receptor that characterises a cell sub-set on interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

B may be independently selected from anti-anti-any soluble molecule cytokine, chemokine, hormone etc.

Y may be an anti-peptide scFv or sdAb e.g. 52SR4

X may be a peptide that binds Y (for example GCN4)

Example 20—IgG Capture from Antibody Secreting Cells

One of the distinctions of antibody secreting B cells is their switch from rapidly dividing to non-dividing cells. During this switch the rate of antibody secretion rises prodigiously. A hallmark of this switch from B cell to plasma cell is the total loss of cell surface IgG (also known as the B cell receptor (BcR)). Cell surface IgG can be used to characterise not only the type of immunoglobulin (for example IgG, IgA, IgE etc.) produced by the cell but also its antigen specificity. Accompanying this change in cell surface IgG is also a progressive loss of classical B cell differentiation markers such as CD20, CD22 and CD19 with a concomitant increase in new markers such as CD38 and CD138. The end result of these changes is that plasma cells are much harder to distinguish from other cells, particularly in tissues, and without cell surface immunoglobulin their nature and antigen specificity can be even harder to establish. At best, current methods that can be used to identify such cells rely on treatments that are detrimental to cell health such as protocols that fix and permeabilise cells to measure intracellular IgG. The method described, using the claimed technology, allows the dual targeting and capture of soluble IgG to the cell surface of the cell that produced it enabling similar applications to those using cell associated BcR. These include the phenotyping, antigen determination, separation and sorting of cells. In addition this method allows any cell receptor to be used to capture secreted IgG which has the advantage of utilising receptors expressed to a higher density than any lineage markers whilst also still allowing lineage marker to be detected independently. This means that more secreted IgG can be captured on the cell surface and allows identification of rarer subsets or immunoglobulins with weaker affinity for antigen. In addition this method may be used to enhance capture on cells that already have surface BcR. The method is flexible and interchangeable in respect to both the cell surface binding partner and capture reagent.

Figure 19:
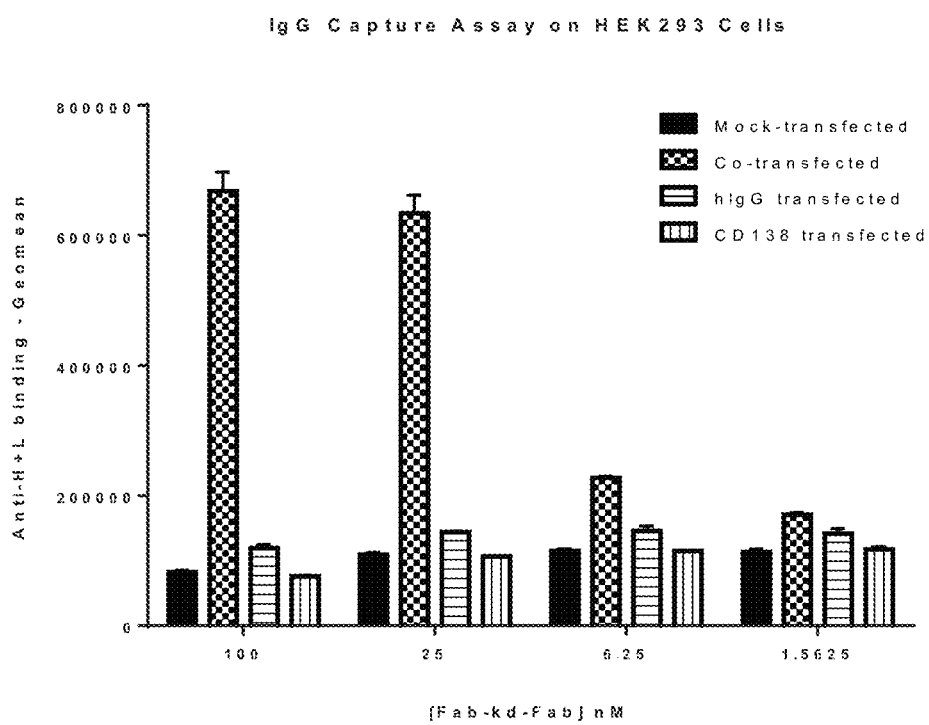
FIG. 19 Mock transfected cells are the solid black bars, CD138 only transfected cells are the vertical black lines, IgG only transfected cells are the horizontal black lines and the dual transfected (CD138 and IgG) cells are the bars with black dots.
Figure 20:
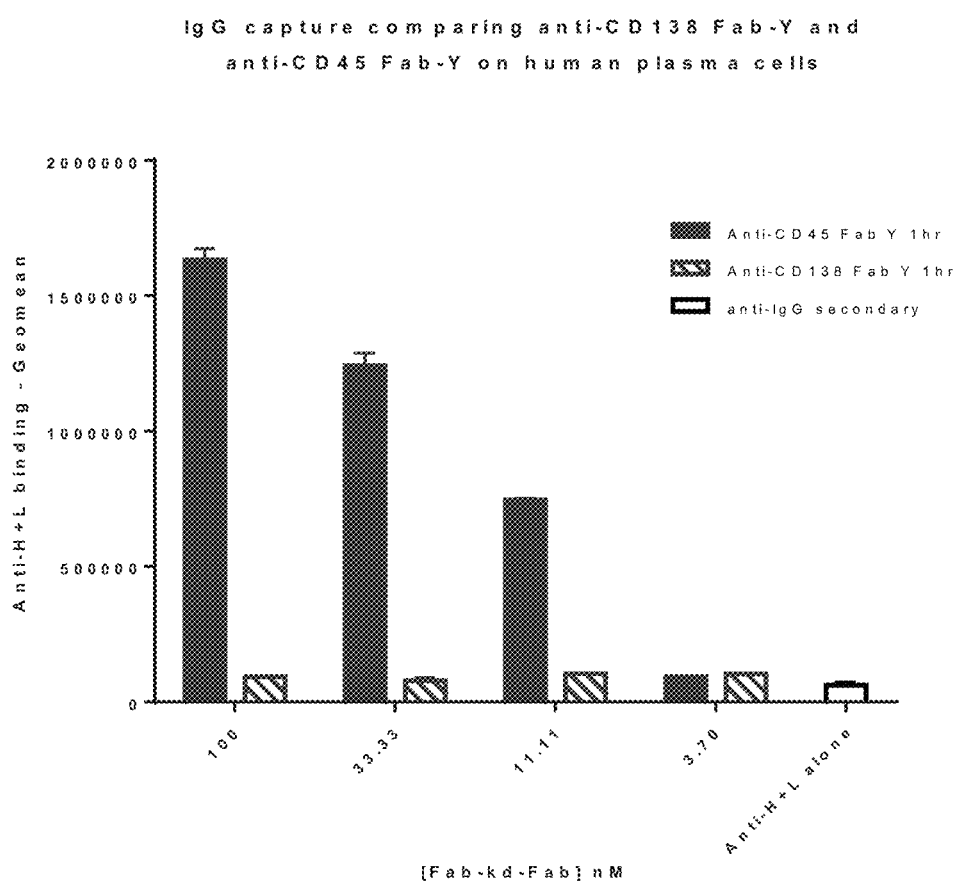
FIG. 20 CD138 Fab-Y is shown as the solid black bars and CD45 Fab-Y is shown as the diagonally striped bars. The secondary antibody alone is shown as the white bars.

Anti-CD138 and anti-CH1 (IgG heavy chain constant region 1 specific) antibodies were expressed in the claimed format which is designed to form bispecific antibodies. To test if anti-CD138 and anti-CH1 could capture secreted IgG, a model system was first used. Human HEK293 cells were co-transfected with the genes for human CD138 and human IgG using a lipid based transfection protocol. As controls, HEK293 cells were transfected with either an empty vector, CD138 alone, IgG alone or co-transfected with CD138 and IgG. A bispecific protein complex was made by mixing anti-CD138 antibody expressed on a Fab-Y format (where Y is the GCN4 peptide or any isoform/derivatives thereof as described herein) with an equimolar mixture of an anti-CH1 antibody expressed on the Fab-X format (where X is 52SR4 as described herein). This was pre-incubated for one hour before being titrated and then incubated with cells for a further hour before being washed off. If CD138 binds the cell surface and captures IgG (through binding CH1) then it can be detected with a polyclonal goat anti-human heavy and light (H+L) chain (IgG) specific antibody conjugated to APC. This binding can then be detected using a flow cytometer. FIG. 19 shows that only cells co-transfected with CD138 and IgG but not CD138 or IgG alone can be detected using the polyclonal anti-IgG H+L chain specific antibody. In a separate experiment commercially available anti-CD138 antibodies were used to determine the level of CD138 expressed on the transfected HEK293 cells (data not shown). In order to determine if this method could be applied to primary human antibody secreting cells human plasma blasts were generated according to a protocol adapted from Jourdan et al (Blood. 114(25). pp 5173). This method yielded antibody secreting cells (as determined by an IgG ELISA) that were also CD138 positive. In addition these cells were determined to have very low levels of surface immunoglobulin which is also another hallmark of plasma cells or plasma blasts. FIG. 20 compares the use of either CD138 or CD45 Fab-Y pre-complexed with anti-CH1 Fab-X before adding to cultured human plasma cells. After 1 hour cells were washed and cell bound IgG could be measured using a polyclonal anti-H+L APC antibody and cell surface capture detected using a flow cytometer. The graph in FIG. 20 indicates that for the particular constructs tested CD45 was more successful than CD138 at capturing IgG on the surface of human plasma cells.

Figure 21:
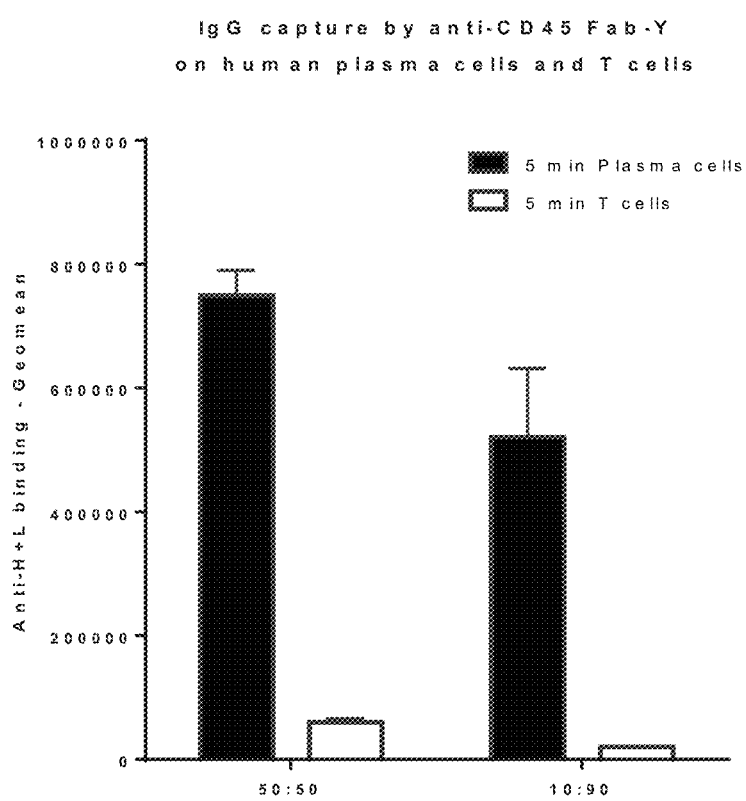
FIG. 21 The T cell IgG capture is shown by the white bars and the plasma cell capture is shown by the solid black bars.

In order to determine if this technique could be useful in mixed cell cultures of plasma cells and T cells (at a ratio of 1:1 or 1:9 plasma cells to T cells) the total cell concentration was fixed to $1 \times 10^4$ cells/ml. The anti-CD45-Y and anti-CH-1-X combination was pre-incubated together for one hour then the pre-formed bispecific complex was then added to cultures which contained a mixture of plasma cells and T cells for 5 minutes before being washed off. Since both cells express roughly equal levels of CD45, it is believed that, both T cells and plasma cells should be capable of capturing IgG (which can only be secreted by the plasma cells). IgG captured at the cell surface can be detected using an anti-H+L APC conjugated antibody and plasma cells can be distinguished from T cells using CD138 and CD3 antibodies, respectively. Cell surface IgG binding was then detected using a flow cytometer. FIG. 21 shows that even at a ratio of 1:1 (plasma cells to T cells) T cells captured very little IgG at their cell surface compared with plasma cells. The relative ratio of binding to plasma cells was at least 10-fold more than to T cells. This data indicates that the claimed technology can selectively capture IgG produced by the cell secreting the IgG and not by a bystander cell.

The invention claimed is:

1. A method of capturing and detecting a soluble molecule of interest produced by a cell of interest, comprising
   i) contacting the cell of interest with a combination of fusion proteins A-X and B-Y in an uncomplexed form or A-X:Y-B in a heterodimerically-tethered bispecific protein complex form, and
   ii) detecting capture of the soluble molecule of interest by component A or B, wherein the soluble molecule of interest is detected with a labeled antigen, a labeled antibody, a labeled binding fragment of an antibody, or a combination thereof,
   wherein:
   X:Y is a heterodimeric-tether;
   : is a binding interaction between X and Y;
   A-X is a fusion protein, wherein A is an antibody or antigen binding fragment thereof that binds a cell surface receptor expressed on cells producing a soluble molecule of interest;
   B-Y is a fusion protein, wherein B is an antibody or antigen binding fragment thereof that binds to the soluble molecule or an antigen,
   X and Y are binding partner, wherein if X is a scFv or a sdAb specific to a peptide GCN4 (SEQ ID NO: 1 or amino acids 1-38 of SEQ ID NO: 1), then Y is the peptide GCN4 (SEQ ID NO: 1 or amino acids 1-38 of SEQ ID NO: 1), or if X is the peptide GCN4 (SEQ ID NO: 1 or amino acids 1-38 of SEQ ID NO: 1), then Y is a scFv or a sdAb specific to the peptide GCN4 (SEQ ID NO: 1 or amino acids 1-38 of SEQ ID NO: 1),
   wherein the secreted soluble molecule is captured to the cell surface by an interaction between X and Y,
   wherein the soluble molecule is selected from the group consisting of a hormone, a cytokine, a chemokine, a chemoattractant, a leukotriene, a prostaglandin, a vasoactive amine, an enzyme, a complement, a lipid, a sphingolipid, a clotting factor, an acute phase protein, a gamma globulin, an albumin, a soluble cell membrane receptor, an immune complex and an intracellular protein from dead or dying cells.

2. The method according to claim 1, wherein the soluble molecule of interest is a cytokine selected from the group comprising: IL-1a, IL-1b, IL-1Ra, IL-2, IL-3, IL-4, IL-5, IL-6, IL-7, IL-9, IL-10, IL-11, IL-12, IL-13, IL-14, IL-15 IL-16, IL-17A, IL-17B, IL-17C, IL-17D, IL-17F, IL-18, IL-19, IL-20, IL-21, IL-22, IL-23, IL-24, IL-25, IL-26, IL-27, IL-28, IL-29, IL-30, IL-31, IL-32, IL-3, IL-34, IL-35, IL-36a, IL-36b, IL-36g, IL-37a, IL-37, IL-38, TNSF1, TNFSF2, TNFSF3, TNFSF4, TNFSF5, TNFSF6, TNFSF7, TNFSF8, TNFSF9, TNFSF10, TNFSF11, TNFSF12, TNFSF13, TNFSF13b, TNFSF14, TNFSF15, TNFSF18, IFNa, IFNb, IFNe, IFNk, IFNw, IFNg, IFN11, IFN12, IFN12, CSF1, CSF2, CSF3, TGFb1, TGFb2, TGFb3, CLC, CNTF, Leptin, OPG, LIF, Neuropoietin, Oncostain M, NGF, BDNF, NT-3, PAI-1, RBP4, Adiponectin, Apelin, Chimerin, Visfatin, Sclerostin and DKK-1GM.

3. The method according to claim 1, wherein the soluble molecule of interest is a chemokine selected from the group consisting of: CCL1, 2, 3, 4, 5, 6, 7, 8, 9, 10, 11, 12, 13, 14, 15, 16, 17, 18, 19, 20, 21, 22, 23, 24, 25, 26, 27, 28, CXCL 1, 2, 3, 4, 5, 6, 7, 8, 9, 10, 11, 12, 13, 14, 15, 16, 17, XCL1, XCL2 and CX3CL1.

4. The method according to claim 1, wherein the soluble molecule of interest is an immunoglobulin.

5. The method according to claim 4, wherein B is an antibody or an antigen binding fragment thereof specific to an Fc of IgG1, IgG2, IgG3, IgG4, IgA1, IgA2, IgE or IgM.

6. The method according to claim 1, wherein the cell surface marker is selected from the group consisting of: CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, and Lin-1 to -3.

7. The method according to claim 1, wherein A is an antibody specific to a cell marker selected from the group consisting of:
   a. CD38, CD138, CD45, isoform thereof, CD27, CD19, and CD20 on B cell or plasma cell, and
   b. B is an antibody selected from the group consisting of anti-CH1, anti-Cκ, anti-Cλ, anti-Fc pan isotype, anti-Fc of IgG1, IgG2, IgG3, IgG4, IgE and IgA.

8. The method according to claim 1, wherein the cell of interest is antigen specific antibody producing cell,
- A is a full-length antibody, a Fab fragment, a Fab' fragment, a sdAb, or scFv and
- B is the antigen.

9. The method according to claim 8, wherein the cell expresses immunoglobulins on its surface specific to said antigen.

10. The method according to claim 1, wherein B:
- a. is independently selected from an antibody, a Fab fragment, a Fab' fragment, a sdAb, and a scFv; or
- b. is the antigen.

11. The method according to claim 1, wherein X is fused to the C-terminal of the protein component A of the heavy chain of an antibody or binding fragment thereof.

12. The method according to claim 1, wherein Y is fused to the C-terminal of the protein component B of the heavy chain of an antibody or binding fragment thereof.

13. The method according to claim 1, wherein X or Y is a scFv.

14. The method according to claim 1, wherein X or Y is a sdAb.

15. The method according to claim 1, wherein the scFv is 52SR4 (SEQ ID NO: 3 or amino acids 1-243 of SEQ ID NO: 3).

16. The method according to claim 15, wherein the binding affinity between X and Y is 5 nM or stronger, 900 pM or stronger.

17. The method according to claim 1, wherein the method is ex vivo or in vitro.

* * * * *

UNITED STATES PATENT AND TRADEMARK OFFICE
CERTIFICATE OF CORRECTION

| | | |
|---|---|---|
| PATENT NO. | : 10,829,566 B2 | Page 1 of 1 |
| APPLICATION NO. | : 15/779426 | |
| DATED | : November 10, 2020 | |
| INVENTOR(S) | : Rapecki | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this
Fourteenth Day of February, 2023

*Katherine Kelly Vidal*
Katherine Kelly Vidal
*Director of the United States Patent and Trademark Office*